US009982059B2

(12) United States Patent
Okano et al.

(10) Patent No.: US 9,982,059 B2

(45) Date of Patent: *May 29, 2018

(54) PHARMACEUTICAL COMPOSITION FOR TREATMENT AND PREVENTION OF CANCERS

(71) Applicant: TORAY INDUSTRIES, INC., Tokyo (JP)

(72) Inventors: Fumiyoshi Okano, Kamakura (JP); Takayoshi Ido, Kamakura (JP); Takanori Saito, Kamakura (JP); Shinichi Kobayashi, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/092,469

(22) Filed: Apr. 6, 2016

(65) Prior Publication Data

US 2016/0208014 A1 Jul. 21, 2016

Related U.S. Application Data

(62) Division of application No. 13/057,709, filed as application No. PCT/JP2009/063882 on Aug. 5, 2009, now Pat. No. 9,416,192.

(30) Foreign Application Priority Data

Aug. 5, 2008 (JP) ................................ 2008-201928
Mar. 31, 2009 (JP) ................................ 2009-087285

(51) Int. Cl.

*C07K 16/30* (2006.01)
*A61K 39/395* (2006.01)
*A61K 39/00* (2006.01)

(52) U.S. Cl.

CPC .... *C07K 16/3015* (2013.01); *A61K 39/39558* (2013.01); *C07K 16/30* (2013.01); *C07K 16/3053* (2013.01); *A61K 2039/505* (2013.01); *C07K 2317/24* (2013.01); *C07K 2317/34* (2013.01); *C07K 2317/565* (2013.01); *C07K 2317/732* (2013.01); *C07K 2317/734* (2013.01)

(58) Field of Classification Search

CPC .................... C07K 16/28; C07K 16/30; C07K 16/3015–16/3069; C07K 16/303; C07K 16/461–16/467; C07K 2317/73–2317/734; A61K 39/395; A61K 39/39558

See application file for complete search history.

(56) References Cited

U.S. PATENT DOCUMENTS

| | | | |
|---|---|---|---|
| 5,698,396 A | 12/1997 | Pfreundschuh | |
| 6,335,170 B1 | 1/2002 | Orntoft | |
| 6,444,425 B1 | 9/2002 | Reed et al. | |
| 7,449,184 B2 | 11/2008 | Allison et al. | |
| 7,485,302 B2 | 2/2009 | Adams et al. | |
| 7,745,391 B2 | 6/2010 | Mintz et al. | |
| 8,008,431 B2 | 8/2011 | Weinschenk et al. | |
| 8,211,634 B2 | 7/2012 | DePinho et al. | |
| 8,709,418 B2 | 4/2014 | Okano et al. | |
| 8,828,398 B2 | 9/2014 | Kobayashi et al. | |
| 8,911,740 B2 * | 12/2014 | Saito | C07K 16/30 424/133.1 |
| 8,937,160 B2 * | 1/2015 | Kobayashi | C07K 16/28 530/387.1 |
| 9,115,200 B2 * | 8/2015 | Okano | C07K 16/3015 |
| 9,175,074 B2 | 11/2015 | Okano et al. | |
| 9,180,187 B2 * | 11/2015 | Ido | A61K 39/39558 |
| 9,180,188 B2 | 11/2015 | Kobayashi et al. | |
| 9,181,334 B2 * | 11/2015 | Kobayashi | C07K 16/30 |
| 9,181,348 B2 * | 11/2015 | Kobayashi | C07K 16/30 |
| 9,260,513 B2 * | 2/2016 | Kobayashi | A61K 39/3955 |
| 9,266,958 B2 * | 2/2016 | Kobayashi | C07K 16/28 |
| 9,273,128 B2 * | 3/2016 | Okano | C07K 16/30 |
| 9,273,130 B2 * | 3/2016 | Kobayashi | C07K 16/30 |
| 9,409,993 B2 * | 8/2016 | Minamida | C07K 14/4738 |
| 9,416,191 B2 * | 8/2016 | Kobayashi | C07K 14/4748 |
| 9,416,193 B2 * | 8/2016 | Saito | C07K 16/28 |
| 9,428,581 B2 * | 8/2016 | Saito | C07K 14/47 |
| 9,573,993 B2 * | 2/2017 | Okano | A61K 39/3955 |
| 9,796,775 B2 * | 10/2017 | Ido | C07K 16/18 |
| 2003/0118599 A1 | 6/2003 | Algate et al. | |
| 2003/0190640 A1 | 10/2003 | Faris et al. | |

(Continued)

FOREIGN PATENT DOCUMENTS

| | | | |
|---|---|---|---|
| CN | 1678338 A | 10/2005 | |
| CN | 1705676 A | 12/2005 | |

(Continued)

OTHER PUBLICATIONS

Akiyoshi, "Cancer Vaccine Therapy Using Peptides Derived from Tumor-rejection Antigens," Jpn. J. Cancer Chemother., vol. 24, No. 5, Mar. 1997, pp. 511-519, with English Abstract (p. 519).
Balmaña et al., "BRCA in breast cancer: ESMO Clinical Recommendations," Annals of Oncology (Supp 4):iv19-iv20, 2009.
Bodey et al., "Failure of Cancer Vaccines: The Significant Limitations of this Approach to Immunotherapy," Anticancer Research, vol. 20, 2000, pp. 2665-2676.
Bodey et al., "MAGE-1, a Cancer/Testis-Antigen, Expression in Childhood Astrocytomas as an Indicator of Tumor Progression," in vivo (2002) vol. 16, pp. 583-588.
Brand et al., "Prospect for Anti-HER2 Receptor Therapy in Breast Cancer." Anticancer Research 26; 463-470 (2006).
Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

(Continued)

*Primary Examiner* — Jessica H Roark

(74) *Attorney, Agent, or Firm* — Birch, Stewart, Kolasch & Birch, LLP

(57) ABSTRACT

The present invention relates to a pharmaceutical composition for treatment and/or prevention of cancer, which comprises, as an active ingredient, an antibody or fragment thereof having an immunological reactivity with a CAPRIN-1 protein or a fragment thereof comprising 7 or more consecutive amino acids.

14 Claims, 10 Drawing Sheets

(56) References Cited

U.S. PATENT DOCUMENTS

| | | | | |
|---|---|---|---|---|
| 2004/0029114 | A1 | 2/2004 | Mack et al. | |
| 2004/0236091 | A1 | 11/2004 | Chicz et al. | |
| 2004/0258678 | A1 | 12/2004 | Bodary et al. | |
| 2005/0003390 | A1 | 1/2005 | Axenovich et al. | |
| 2005/0032113 | A1 | 2/2005 | Tanaka et al. | |
| 2005/0129690 | A1 | 6/2005 | Bowdish et al. | |
| 2005/0244413 | A1 | 11/2005 | Guenther et al. | |
| 2006/0019256 | A1 | 1/2006 | Clarke et al. | |
| 2006/0069054 | A1 | 3/2006 | Houghton et al. | |
| 2006/0275305 | A1 | 12/2006 | Bryant | |
| 2007/0048301 | A1 | 3/2007 | Bodary-Winter et al. | |
| 2007/0083334 | A1 | 4/2007 | Mintz et al. | |
| 2007/0154931 | A1 | 7/2007 | Radich et al. | |
| 2008/0075722 | A1 | 3/2008 | DePinho et al. | |
| 2008/0107668 | A1 | 5/2008 | Philip et al. | |
| 2008/0161293 | A1 | 7/2008 | Yoshinaga et al. | |
| 2008/0306018 | A1 | 12/2008 | Croce et al. | |
| 2010/0029573 | A1 | 2/2010 | Weinschenk et al. | |
| 2010/0068724 | A1 | 3/2010 | Fung et al. | |
| 2011/0123492 | A1 | 5/2011 | Okano et al. | |
| 2011/0136121 | A1 | 6/2011 | Okano et al. | |
| 2011/0189700 | A1 | 8/2011 | Moses et al. | |
| 2011/0256144 | A1 | 10/2011 | Okano et al. | |
| 2012/0171699 | A1 | 7/2012 | Goodman et al. | |
| 2012/0214975 | A1 | 8/2012 | Sandig et al. | |
| 2012/0294860 | A1 | 11/2012 | Ido et al. | |
| 2012/0301471 | A1 | 11/2012 | Kobayashi et al. | |
| 2012/0301476 | A1 | 11/2012 | Okano et al. | |
| 2012/0321641 | A1 | 12/2012 | Okano et al. | |
| 2013/0045210 | A1 | 2/2013 | Kobayashi et al. | |
| 2013/0071398 | A1 | 3/2013 | Saito et al. | |
| 2014/0154261 | A1 | 6/2014 | Okano et al. | |
| 2014/0178373 | A1 | 6/2014 | Kobayashi et al. | |
| 2014/0179558 | A1* | 6/2014 | Ido | C07K 14/4738 506/9 |
| 2014/0186359 | A1 | 7/2014 | Okano et al. | |
| 2014/0193434 | A1 | 7/2014 | Kobayashi et al. | |
| 2014/0199311 | A1 | 7/2014 | Kobayashi et al. | |
| 2014/0308283 | A1 | 10/2014 | Minamida et al. | |
| 2015/0004171 | A1 | 1/2015 | Kobayashi et al. | |
| 2015/0017172 | A1 | 1/2015 | Kobayashi et al. | |
| 2015/0044221 | A1 | 2/2015 | Kobayashi et al. | |
| 2015/0050283 | A1 | 2/2015 | Okano et al. | |
| 2015/0185222 | A1* | 7/2015 | Ido | G01N 33/57492 435/7.93 |
| 2015/0218285 | A1 | 8/2015 | Saito et al. | |
| 2016/0297889 | A1* | 10/2016 | Okano | C07K 16/28 |

FOREIGN PATENT DOCUMENTS

| | | | |
|---|---|---|---|
| CN | 101120252 | A | 2/2008 |
| CN | 101189516 | A | 5/2008 |
| CN | 101836116 | A | 9/2010 |
| CN | 102170907 | A | 8/2011 |
| CN | 102171570 | A | 8/2011 |
| EP | 1557172 | A1 | 7/2005 |
| EP | 2 207 037 | A1 | 7/2010 |
| EP | 2 325 648 | A1 | 5/2011 |
| EP | 2322221 | A1 | 5/2011 |
| EP | 2 532 367 | A1 | 12/2012 |
| EP | 2 532 743 | A1 | 12/2012 |
| EP | 2 740 794 | A1 | 6/2014 |
| EP | 2 832 365 | A1 | 2/2015 |
| EP | 2 832 366 | A1 | 2/2015 |
| JP | 2002-540790 | A | 12/2002 |
| JP | 2003-528587 | A | 9/2003 |
| JP | 2006-316040 | A | 11/2006 |
| JP | 2013-502205 | A | 1/2013 |
| JP | 2013-505028 | A | 2/2013 |
| RU | 2161042 | C2 | 12/2000 |
| RU | 2234942 | C2 | 8/2004 |
| RU | 2244720 | C2 | 1/2005 |
| RU | 2306952 | C2 | 9/2007 |
| RU | 2319709 | C2 | 3/2008 |
| RU | 2006137060 | A | 4/2008 |
| RU | 2391982 | C2 | 6/2010 |
| WO | WO 96/09551 | A1 | 3/1996 |
| WO | WO 00/04149 | A2 | 1/2000 |
| WO | WO 00/05268 | A1 | 2/2000 |
| WO | WO 00/60077 | A2 | 10/2000 |
| WO | WO 01/32910 | A2 | 5/2001 |
| WO | WO 01/72295 | A2 | 10/2001 |
| WO | WO 02/078524 | A2 | 10/2002 |
| WO | WO 02/083070 | A2 | 10/2002 |
| WO | WO 02/092001 | A2 | 11/2002 |
| WO | WO 03/007889 | A2 | 1/2003 |
| WO | WO 2004/076682 | A2 | 9/2004 |
| WO | WO 2004/097051 | A2 | 11/2004 |
| WO | WO 2005/007830 | A2 | 1/2005 |
| WO | WO 2005/100998 | A2 | 10/2005 |
| WO | WO 2005/116051 | A2 | 12/2005 |
| WO | WO 2005/116076 | A2 | 12/2005 |
| WO | WO 2006/002378 | A2 | 1/2006 |
| WO | WO 2007/150077 | A2 | 12/2007 |
| WO | WO 2008/031041 | A2 | 3/2008 |
| WO | WO 2008/059252 | A2 | 5/2008 |
| WO | WO 2008/073162 | A2 | 6/2008 |
| WO | WO 2009/113742 | A1 | 6/2008 |
| WO | WO 2008/088583 | A2 | 7/2008 |
| WO | WO 2009/117277 | A2 | 9/2009 |
| WO | WO 2010/016525 | A1 | 2/2010 |
| WO | WO 2010/016526 | A1 | 2/2010 |
| WO | WO 2010/016527 | A1 | 2/2010 |
| WO | WO 2011/096517 | A1 | 8/2011 |
| WO | WO 2011/096519 | A1 | 8/2011 |
| WO | WO 2011/096528 | A1 | 8/2011 |
| WO | WO 2011/096533 | A1 | 8/2011 |
| WO | WO 2011/096534 | A1 | 8/2011 |
| WO | WO 2011/096535 | A1 | 8/2011 |
| WO | WO 2012/005550 | A2 | 1/2012 |
| WO | WO 2012/013609 | A1 | 2/2012 |
| WO | WO 2013/018885 | A1 | 2/2013 |
| WO | WO 2013/018886 | A1 | 2/2013 |
| WO | WO 2013/018894 | A1 | 2/2013 |
| WO | WO 2013/147169 | A1 | 10/2013 |
| WO | WO 2013/147176 | A1 | 10/2013 |

OTHER PUBLICATIONS

Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.

Chamberlain et al., "Innovations and strategies for the development of anticancer vaccines," Expert Opinion on Pharmacotherapy, vol. 1, No. 4, 2000, pp. 603-614.

Chames et al., "Therapeutic Antibodies for the Treatment of Pancreatic Cancer," The Scientific World Journal (Jan. 1, 2010), vol. 10, pp. 1107-1120.

Comtesse et al., "Probing the human natural autoantibody repertoire using an immunoscreening approach," Clin. Exp. Immunol. (2000), vol. 121, pp. 430-436.

Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. (2002), vol. 169, pp. 3076-3084.

Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.

Ellis, Juliet A. et al., "Identification and Characterization of a Novel Protein (p137) Which Transcytoses Bidirectionally in Caco-2 Cells", The Journal of Biological Chemistry, vol. 270, No. 35, Issue of Sep. 1, pp. 20717-20723, 1995.

Esteva et al., "Chemotheraphy of Metastatic Breast Cancer: What to Expect in 2001 and Beyond," The Oncologist (2001), vol. 6, pp. 133-146.

(56) References Cited

OTHER PUBLICATIONS

European Search Report for European Application No. 11739882.6 dated Aug. 13, 2013.
European Search Report dated Nov. 5, 2013 in European Patent Application 11739876.8.
Evans et al., "Vaccine therapy for cancer—fact or fiction?", Q. J. Med., vol. 92, 1999, pp. 299-307.
Extended European Search Report for European Application No. 13767612.8, dated Sep. 22, 2015.
Extended European Search Report for European Application No. 13769665.4, dated Sep. 22, 2015.
Extended European Search Report dated Feb. 2, 2015, in European Patent Application No. 12819473.5.
Extended European Search Report dated Jan. 29, 2015, in European Patent Application No. 12819899.1.
Extended European Search Report dated Mar. 18, 2015, in European Patent Application No. 12820225.6.
Extended European Search Report dated Mar. 2, 2015, in European Patent Application No. 12819759.7.
Extended European Search Report issued Mar. 23, 2015, in European Patent Application No. 12820596.0.
GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_005898, Feb. 11, 2008.
GenBank Accession No. NM_016739, Feb. 10, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
Gong et al., "Caprin-1 is a novel microRNA-223 target for regulating the proliferation and invasion of human breast cancer cells," Biomedicine & Pharmacotheraphy (2013), vol. 67, pp. 629-636.
Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Güre et al., "SSX: A Multigene Family with Several Members Transcribed in Normal Testis and Human Cancer," Int. J. Cancer, vol. 72, 1997, pp. 965-971.
Harlow et al., Antibodies A Laboratory Manual, Cold Spring Harbor Laboratory, Chapter 3, pp. 23-34, Cold Spring Harbor, New York, 11724, 1988.
Houghton, P. J. and J. A. Houghton, "Evaluation of Single-Agent Therapy in Human Colorectal Tumour Xenografts," Br. J. Cancer (1978), vol. 37, pp. 833-840.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
International Search Report dated Nov. 18, 2014, in PCT International Application No. PCT/JP2014/071094.
International Search Report, issued in PCT/JP2009/063882, dated Oct. 6, 2009.
Itoh et al., "HUB1 is an autoantigen frequently eliciting humoral immune response in patients with adult T cell leukemia," Int. J. Oncol., vol. 14, 1999, pp. 703-708 (Abstract only provided).
Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.
Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Jungbluth et al., "Immunohistochemical Analysis of NY-ESO-1 Antigen Expression in Normal and Malignant Human Tissues," Int. J. Cancer (2001), vol. 92, pp. 856-860.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Kataja and Castiglione, "Primary breast cancer: ESMO Clinical Recommendations for diagnosis, treatment and follow-up" Annals of Oncology 20 (Supp 4); iv10-iv14 2009.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Katsafanas et al., "Vaccinia Virus Intermediate Stage Transcription is Complemented by Ras-GTPase-activating Protein SH3 Domain-binding Protein (G3BP) . . . ," Jour. of Biol. Chem., vol. 279, No. 50, Dec. 10, 2004, pp. 52210-52217.
Kohler et al., "Tumor antigen analysis in neuroblastoma by serological interrogation of bioinformatic data," Cancer Science (Nov. 2010), vol. 101, No. 11, pp. 2316-2324.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Proceedings Abstract No. 4131, Apr. 14-18, 2007 (Presentation conducted an Apr. 17, 2007) (Abstract only provided).
Lu et al., "Targeting serum antibody for cancer diagnosis: a focus on colorectal cancer," Oncologic, Endocrine & Metabolic, Expert Opinion on Therapeutic Targets, vol. 11, No. 2, Feb. 2007, pp. 235-244.
Müller-Pillasch et al., "Identification of a new tumour-associated antigen TM4SF5 and its expression in human cancer," Gene, vol. 208, 1998, pp. 25-30.
Munodzana et al., "Conformational Dependence of Anaplasma Marginale Major Surface Protein 5 Surface-Exposed B-Cell Epitopes", Infection and Immunity, vol. 66, No. 6, Jun. 1998, pp. 2619-2624.
Nakamura et al. "Gene Expression Profile of Metastatic Human Pancratic Cancer Cells Depends on the Organ Microenvironment," Cancer Research (Jan. 1, 2007), vol. 67, No. 1, pp. 139-148.
NCBI Reference Sequence, caprin-1 [Bos taurus], Feb. 23, 2013, Accession No. NP001069530, XP615677, 1 page.
NCBI Reference Sequence, caprin-1 [Gallus gallus], Feb. 22, 2013, Accession No. NP001026536, XP423820, 1 page.
NCBI Reference Sequence, caprin-1 isoform 1 [*Homo sapiens*], Mar. 17, 2013, Accession No. NP005889, 3 pages.
NCBI Reference Sequence, caprin-1 isoform 2 [*Homo sapiens*], Mar. 3, 2013, Accession No. NP976240, 3 pages.
NCBI Reference Sequence, caprin-1 isoform a [Mus musculus], Mar. 23, 2013, Accession No. NP058019, 3 pages.
NCBI Reference Sequence, caprin-1 isoform b [Mus musculus], Mar. 23, 2013, Accession No. NP001104760, 3 pages.
NCBI Reference Sequence, caprin-1 isoform c [Mus musculus], Mar. 23, 2013, Accession No. NP001104761,4 pages.
NCBI Reference Sequence, Predicted: caprin-1 [Equus caballus], Jun. 27, 2011, Accession No. XP001492799, 1 page.
NCBI Reference Sequence, Predicted: caprin-1 isoform 2 [Canis lupus familiaris], Dec. 2, 2011, Accession No. XP858109, 1 page.
Nelson et al., "Screening for Breast Cancer: An Update for the U.S. Preventive Services Task Force," Ann. Intern. Med. 2009;151:727-737.
Non-Final Office Action dated Apr. 14, 2015, in U.S. Appl. No. 14/236,793.

(56) References Cited

OTHER PUBLICATIONS

Non-Final Office Action dated Nov. 6, 2014, in U.S. Appl. No. 13/576,950.
Office Action dated Nov. 15, 2013, in U.S. Appl. No. 13/576,950.
Office Action for U.S. Appl. No. 13/576,969 dated Oct. 15, 2013.
Office Action for U.S. Appl. No. 13/577,212 dated Oct. 21, 2013.
Office Action dated Aug. 14, 2015, in U.S. Appl. No. 14/236,818.
Office Action dated Aug. 20, 2015, in U.S. Appl. No. 14/452,746.
Office Action dated Jan. 28, 2015, in Russian Patent Application No. 2012137502, with partial English translation.
Office Action dated Jul. 3, 2015, in Russian Patent Application No. 2012137503.
Office Action dated Sep. 15, 2015, in U.S. Appl. No. 14/389,266.
Office Action, dated Jan. 16, 2014, for U.S. Appl. No. 13/057,515.
Okano et al., "Identification of a novel target for antibody therapy of breast cancer", Cancer Research, vol. 72, No. 8, Apr. 15, 2012.
Padlan, E. A., "X-Ray Crystallography of Antibodies," Adv. Prot. Chem. (1996), vol. 49, pp. 57-133.
Patent Examination Report No. 1 dated Oct. 14, 2014, in Australian Patent Application No. 2009278387.
Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.
Polyak, et al., "Alanin-170 and proline-172 are critical determinants for extracellular CD20 epitopes; heterogeneity in the fine specificity of CD20 monoclonal antibodies is defined by additional requirements . . . ", Blood, vol. 99, No. 9, pp. 3256-3262, 2002.
Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.
Qui et al., "Targeting a ribonucleoprotein complex containing the caprin-1 protein and the c-Myc mRNA suppresses tumor growth in mice: an identification of a novel oncotarget," Oncotarget (2014), vol. 6, No. 4, pp. 2148-2163.
R&D Systems, Tools for Cell Biology Research, "IHC Products & Protocol Guide" (printed Jan. 9, 2014).
Rauch et al., "SEREX, Proteomex, Amida, and beyond: Serological screening technologies for target identification," Proteomics Clin. Appl., vol. 2, 2008, pp. 355-371.
Riechmann et al., "Reshaping human antibodies for therapy," Nature (Mar. 24, 1988), vol. 332, pp. 323-327.
Russian Notice of Allowance dated Jan. 24, 2014 for Russian Application No. 20110108258.
Sabile et al., "Caprin-1, a novel Cyr61-interacting protein, promotes osteosarcoma tumor growth and lung metastasis in mice," Biochimica et Biophysica Acta (2013), vol. 1832, pp. 1173-1182.
Saffari et al., "Identification of novel p53 target genes by cDNA AFLP in glioblastoma cells", Cancer Letters, 2009, No. 273, pp. 316-322.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," Int. J. Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2•, Entry to Cytoplasmic Stress Granules . . . ," Molecular and Cellular Biology, vol. 27, No. 6, Mar. 2007, pp. 2324-2342.
Strome et al., "A Mechanistic Perspective of Monoclonal Antibodies in Cancer Therapy Beyond Target-Related Effects," The Oncologist 2007;12:1084-1095.
Türeci et al., "The SSX-2 Gene, Which is Involved in the t(X; 18) Translocation of Synovial Sarcomas, Codes for the Human Tumor Antigen HOM-MEL-40," Cancer Research, vol. 56, Oct. 15, 1996, pp. 4766-4772.
U.S. Office Action dated Nov. 15, 2013 in U.S. Appl. No. 13/577,028.
U.S. Office Action for U.S. Appl. No. 14/379,867, dated Jun. 24, 2015.
U.S. Office Action, dated Jul. 1, 2013, for U.S. Appl. No. 13/577,212.
Vajdos et al,. "Comprehensive Functional Maps of the Antigen-bining Site of an Anti-ErbB2 Antibody Obtained with Shotgun Scanning Mutagenesis," J. Mol. Biol. (2002), vol. 320, pp. 415-428.
Van Der Bruggen et al., "A Gene Encoding an Antigen Recognized by Cytolytic T Lymphocytes on a Human Melanoma," Science, vol. 254, No. 5038, Dec. 13, 1991, pp. 1643-1647 (Also published in J. Immunol., vol. 178, 2007, pp. 2617-2621).
Wang, B. et al., "Absence of Caprin-1 Results in Defects in Cellular Proliferation1", The Journal of Immunology, 2005, vol. 175, No. 7, pp. 4274 to 4282.
"*Homo sapiens* cell cycle associated protein 1, mRNA (cDNA clone MGC:1378 Image:3355481), complete cds", Genebank database, NCBI Accession No. BC001731, Sep. 11, 2007.
Bodey et al. (Anticancer Research 20: 2665-2676, 2000).
Carter, Paul J., "Potent antibody therapeutics by design", Nature Reviews Immunology, vol. 6, May 2006, pp. 343-357.
Chamberlain et al. (Expert Opinion on Pharmacotherapy, 1(4): 603-614, 2000).
Extended European Search Report for Appl. No. 13820574.5 dated Jan. 11, 2016.
GeneCards (updated Mar. 29, 2013).
Huang, J. et al, "IgG isotype Conversion of a Novel Human Anti-carcinoembryonic Antigen Antibody to Increase its Biological Activity," Anticancer Research, 2006, vol. 26, No. 2A, pp. 1057-1063.
Karauzum et al., (American Society of Human Genetics, Abstract/Program No. 1190W, Oct. 12, 2011).
Shibaguchi, H. et al, "New Human Antibody IgG Subclass Conversion for Enhancement of Tumor-Cytotoxic Activity," Research, 2006, vol. 11, No. 3, pp. 15-16.
Russian Office Action and Search Report for Russian Application No. 2014143784, dated Jan. 19, 2017, including a partial English translation.
Russian Notice of Allowance for Russian Application No. 2014108049/10, dated May 16, 2016, with an English translation.
U.S. Office Action for U.S. Appl. No. 14/415,090, dated May 19, 2016.
U.S. Office Action for U.S. Appl. No. 14/415,520, dated May 19, 2016.
Russian Decision on Grant for Russian Application No. 2012137504/10, dated Jun. 22, 2016, with an English translation.
Russian Office Action for Russian Application No. 2014138041/10, dated Jul. 5, 2016, with an English translation.
Roitt et al., "NK cells and K cells use several different receptors on the surface, to identify their targets," Immunology, 2000, p. 181 (4 pages), with an English abstract.
Russian Office Action and English translation thereof, dated Apr. 17, 2017, for Russian Application No. 2014143785/10.
Extended European Search Report dated Feb. 27, 2017, in European Patent Application No. 14834828.7.
Indian Examination Report dated Feb. 23, 2017, in Indian Patent Application No. 960/KOLNP/2011.
NCBI Reference Sequence:NP_005889 for human CAPRIN-1, printed Apr. 2017.
Russian Decision on Grant of Patent for Invention dated Mar. 13, 2017, in Russian Patent Application No. 2012137503, with English translation.
Russian Decision on Grant of Patent for Invention dated Mar. 29, 2017, in Russian Patent Application No. 2014108048, with English translation.

(56) References Cited

OTHER PUBLICATIONS

U.S. Non-Final Office Action dated Apr. 26, 2017, in U.S. Appl. No. 13/057,515.

* cited by examiner

PHARMACEUTICAL COMPOSITION FOR TREATMENT AND PREVENTION OF CANCERS

CROSS-REFERENCE TO RELATED APPLICATIONS

This application is a Divisional of copending application Ser. No. 13/057,709, filed on Feb. 4, 2011, which was filed as PCT International Application No. PCT/JP2009/063882 on Aug. 5, 2009, and to Patent Applications No. JP 2009-087285 filed in Japan on Mar. 31, 2009 and No. JP 2008-201928 filed in Japan on Aug. 5, 2008, all of which are hereby expressly incorporated by reference into the present application.

TECHNICAL FIELD

The present invention relates to a novel medical use of antibodies to CAPRIN-1 or fragments thereof as, for example, therapeutic and/or preventive agents for cancer.

BACKGROUND OF INVENTION

Cancer is the leading cause of death. Treatment currently performed for cancer is mainly surgical therapy, which can be combined with radiation therapy or chemotherapy. In spite of development of new surgical methods and discovery of new anti-cancer agents in recent years, treatment results of cancers are not greatly improved at present except for some cancers. Through a recent progress of molecular biology and cancer immunology, antibodies that are specifically reactive with cancers, cancer antigens recognized by cytotoxic T cells, as well as the genes encoding the cancer antigens, have been identified, and expectations for specific immunotherapies targeting cancer antigens have been raised (Tsuyoshi AKIYOSHI, "*Gan To Kagaku-Ryoho* (Cancer and Chemotherapy)," 1997, vol. 24, pp. 551-519 (Jp) (Cancer and Chemotherapy Publishers, Inc., Japan)).

In cancer treatment methods, in order to reduce side effects, it is desirable for peptides, polypeptides, or proteins recognized as cancer antigens to be absent in almost all normal cells but specifically present in cancer cells. In 1991, Boon et al of the Ludwig Institute in Belgium isolated the human melanoma antigen MAGE 1 recognized by CD8-positive T cells by the cDNA-expression cloning method using an autologous cancer cell line and cancer-reactive T cells (Bruggen P. et al., Science, 254:1643-1647 (1991)). Thereafter, the SEREX (serological identification of antigens by recombinant expression cloning) method was reported, wherein tumor antigens recognized by antibodies produced through response to an autologous cancer in the body of a patient with cancer can be identified using the gene-expression cloning technique (Proc. Natl. Acad. Sci. USA, 92:11810-11813 (1995); and U.S. Pat. No. 5,698,396). By the SEREX method, some cancer antigens, which are not substantially expressed in normal cells but are specifically expressed in cancer cells, were isolated (Int. J. Cancer, 72: 965-971 (1997); Cancer Res., 58: 1034-1041 (1998); Int. J. Cancer, 29: 652-658 (1998); Int. J. Oncol., 14: 703-708 (1999); Cancer Res., 56: 4766-4772 (1996); and Hum. Mol. Genet 6: 33-39, 1997). Further, clinical trials of cell therapies using immunocytes that specifically react with cancer antigens, which are some of the isolated cancer antigens, and cancer-specific immunotherapies using vaccines comprising cancer antigens or the like have been conducted.

Meanwhile, in recent years, a variety of antibody medicines for cancer treatment that target antigen proteins on cancer cells have come into existence. Such medicines used as cancer-specific therapeutic agents exhibit drug efficacy to a certain extent, and thus they have been gaining attention. However, most of target antigen proteins are also expressed on normal cells. As a result of antibody administration, not only cancer cells, but also normal cells, on which a target antigen has been expressed can be damaged, thereby causing a side (or adverse) effect, which becomes problematic. Hence, it is expected that, if it becomes possible to identify cancer antigens that are specifically expressed on the surface of a cancer cell and to use antibodies targeting such antigens as medicaments, then treatment with antibody medicines that cause fewer side effects could be realized.

Cytoplasmic- and proliferation-associated protein 1 (CAPRIN-1) is an intracellular protein that is expressed when normal cells in resting phase are activated or undergo cell division. CAPRIN-1 is also known to be involved in the regulation of the transport and translation of mRNAs through formation of ctytoplasmic stress granules with RNA in a cell. CAPRIN-1 has different names, such as GPI-anchored membrane protein 1 and membrane component surface marker 1 protein (M11S1), as if this protein is known to be a membrane protein. These different names are derived from the report (J. Biol. Chem., 270: 20717-20723, 1995) that the gene sequence of CAPRIN-1 originally has a GPI-binding region and CAPRIN-1 is a membrane protein expressed in colon cancer cells. It was later reported that the CAPRIN-1 gene sequence described in said report was not correct; i.e., a frame shift took place by deletion of a single nucleotide from the CAPRIN-1 gene sequence currently registered with GenBank or the like, so that 80 amino acids were deleted from the C-terminus and the resulting artifact (74 amino acids) was the GPI binding portion in the report; and another error was also present on the 5' side of the gene sequence, thereby resulting in deletion of 53 amino acids from the N-terminus (J. Immunol., 172: 2389-2400, 2004). Further, it has been reported that the protein encoded by the CAPRIN-1 gene sequence currently registered with GenBank or the like was not a cell membrane protein (J. Immunol., 172: 2389-2400, 2004).

In addition, based on the report of J. Biol. Chem., 270: 20717-20723, 1995 that CAPRIN-1 is a cell membrane protein, US2008/0075722 and WO2005/100998 disclose that CAPRIN-1 under the name of M11S1 can be used for cancer therapy as a target of antibody medicines for cancer therapy and as one of cell membrane proteins; however, the Examples contain no description of the cancer therapy using an antibody against the protein. However, as reported in J. Immunol., 172: 2389-2400, 2004, it was a common belief, from the time of filing US2008/0075722 up to now, that CAPRIN-1 is not expressed on the surface of a cell, and thus, it is obvious that the contents of US2008/0075722 and WO2005/100998 based only on misinformation that CAPRIN-1 is a cell membrane protein should not be understood as common technical knowledge of persons skilled in the art.

SUMMARY OF THE INVENTION

Problem to be Solved by the Invention

An object of the present invention is to identify cancer antigen proteins specifically expressed on the surface of cancer cells and to provide a use of antibodies targeting such proteins as therapeutic and/or preventive (or prophylactic) agents for cancer.

Means for Solving Problem

As a result of intensive studies, the present inventors have now obtained cDNA encoding a protein that binds to an antibody present in the serum from a tumor-bearing organism by the SEREX method using testis tissue-derived cDNA libraries and sera from dogs with breast cancer. With the use of the obtained canine genes and genes homologous thereto from human, bovine, horse, mouse, and chicken, CAPRIN-1 proteins having amino acid sequences shown in the even numbers of SEQ ID NOS: 2 to 30 (i.e., even-numbered SEQ ID NOS: 2 to 30) and antibodies against the CAPRIN-1 proteins have now been prepared. In addition, the present inventors have now found that CAPRIN-1 is specifically expressed in the cells of breast cancer, brain tumor, leukemia, lymphoma, lung cancer, esophageal cancer, colon cancer, gastric cancer, and kidney cancer, and that portions of the CAPRIN-1 proteins are specifically expressed on the surface of such cancer cells. Further, the present inventors have now found that antibodies against the CAPRIN-1 portions expressed on cancer cell surfaces can damage (or impair) cancer cells expressing CAPRIN-1. These findings have led to the completion of the present invention.

Therefore, the present invention has characteristics as described below.

The present invention provides a pharmaceutical composition for treatment and/or prevention of a cancer, which comprises, as an active ingredient, an antibody or a fragment thereof having an immunological reactivity with a CAPRIN-1 protein having an amino acid sequence shown in any one of the even numbered SEQ ID NOS: 2 to 30 or an amino acid sequence having 80% or more, preferably 85% or more, more preferably 90% or more, and further preferably 95% or more sequence identity with the amino acid sequence of any of the even-numbered SEQ ID NOS: 2 to 30, or with a fragment of the CAPRIN-1 protein comprising 7 or more consecutive amino acids.

In one embodiment of the present invention, the cancer is breast cancer, brain tumor, leukemia, lymphoma, lung cancer, esophageal cancer, colon cancer, gastric (or stomach) cancer, or kidney cancer.

In another embodiment of the present invention, the antibody is a monoclonal or polyclonal antibody.

In another embodiment of the present invention, the antibody is a human antibody, a humanized antibody, a chimeric antibody, a single-chain antibody, or a bispecific antibody.

In another embodiment of the present invention, the antibody is an antibody having an immunological reactivity with a polypeptide having the amino acid sequence shown in SEQ ID NO: 37 or SEQ ID NO: 136 or an amino acid sequence having 80% or more, preferably 85% or more, more preferably 90% or more, and further preferably 95% or more sequence identify with the amino acid sequence, or with a fragment of the polypeptide.

In another embodiment of the present invention, in the pharmaceutical composition for treatment and/or prevention of a cancer comprising the antibody as an active ingredient, the above antibody is any one of the antibodies (a) to (k) described below and has an immunological reactivity with a CAPRIN-1 protein.

(a) An antibody comprising a heavy-chain variable region comprising the sequences shown in SEQ ID NOS: 40, 41, and 42 and a light-chain variable region comprising the sequences shown in SEQ ID NOS: 44, 45, and 46.

(b) An antibody comprising a heavy-chain variable region comprising the sequences shown in SEQ ID NOS: 40, 41, and 42 and a light-chain variable region comprising the sequences shown in SEQ ID NOS: 50, 51, and 52.

(c) An antibody comprising a heavy-chain variable region comprising the sequences shown in SEQ ID NOS: 40, 41, and 42 and a light-chain variable region comprising the sequences shown in SEQ ID NOS: 55, 56, and 57.

(d) An antibody comprising a heavy-chain variable region comprising the sequences shown in SEQ ID NOS: 40, 41, and 42 and a light-chain variable region comprising the sequences shown in SEQ ID NOS: 60, 61, and 62.

(e) An antibody comprising a heavy-chain variable region comprising the sequences shown in SEQ ID NOS: 40, 41, and 42 and a light-chain variable region comprising the sequences shown in SEQ ID NOS: 65, 66, and 67.

(f) An antibody comprising a heavy-chain variable region comprising the sequences shown in SEQ ID NOS: 70, 71, and 72 and a light-chain variable region comprising the sequences shown in SEQ ID NOS: 74, 75, and 76.

(g) An antibody comprising a heavy-chain variable region comprising the sequences shown in SEQ ID NOS: 80, 81, and 82 and a light-chain variable region comprising the sequences shown in SEQ ID NOS: 84, 85, and 86.

(h) An antibody comprising a heavy-chain variable region comprising the sequences shown in SEQ ID NOS: 90, 91, and 92 and a light-chain variable region comprising the sequences shown in SEQ ID NOS: 94, 95, and 96.

(i) An antibody comprising a heavy-chain variable region comprising the sequences shown in SEQ ID NOS: 100, 101, and 102 and a light-chain variable region comprising the sequences shown in SEQ ID NOS: 104, 105, and 106.

(j) An antibody comprising a heavy-chain variable region comprising the sequences shown in SEQ ID NOS: 110, 111, and 112 and a light-chain variable region comprising the sequences shown in SEQ ID NOS: 114, 115, and 116.

(k) An antibody comprising a heavy-chain variable region comprising the sequences shown in SEQ ID NOS: 120, 121, and 122 and a light-chain variable region comprising the sequences shown in SEQ ID NOS: 124, 125, and 126.

Effects of the Invention

Antibodies against CAPRIN-1 used in the present invention damage (or impair) cancer cells. Therefore, such antibodies against CAPRIN-1 are useful for treatment or prevention of cancers.

MODE FOR CARRYING OUT THE INVENTION

Figure 1:
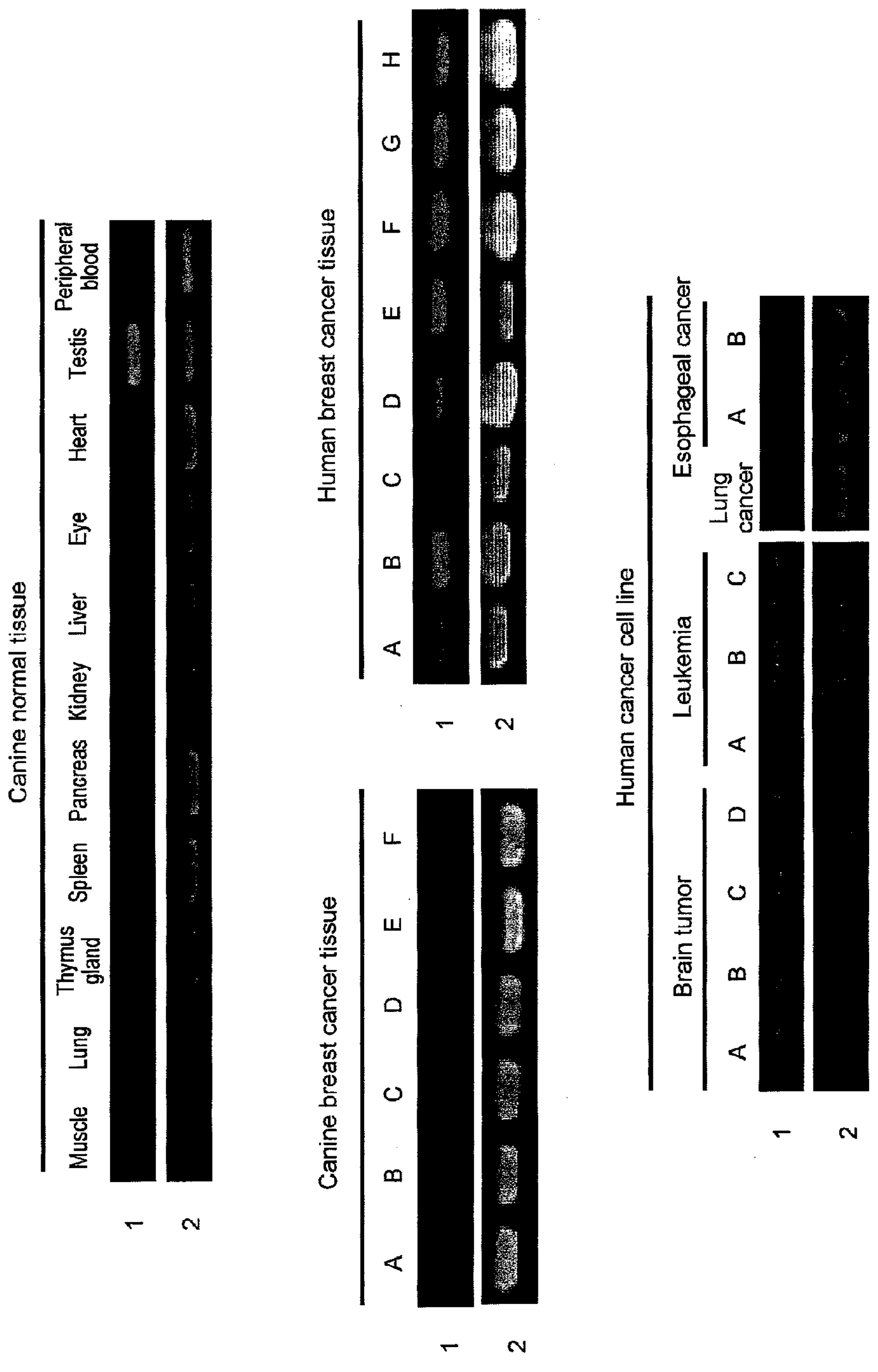
FIG. 1 shows expression patterns of genes encoding CAPRIN-1 proteins in normal tissues and tumor cell lines. In this Fig., reference no. 1 shows the expression pattern of each CAPRIN-1 coding gene, and reference no. 2 shows the expression pattern of GAPDH gene.

As described below, the antitumor activity of antibodies to the polypeptide shown in any one of the even-numbered SEQ ID NOS: 2 to 30 used in the present invention can be evaluated by examining in vivo the inhibition of tumor growth in a tumor-bearing animal, or by examining in vitro whether or not immunocyte- or complement-mediated cytotoxic activity against tumor cells expressing the polypeptide is exhibited.

In addition, the nucleotide sequences of polynucleotides encoding the proteins consisting of the amino acid sequences shown in the even-numbered SEQ ID NOS: 2 to 30 (i.e., SEQ ID NOS: 2, 4, 6 . . . 28, and 30) are shown in the odd-numbered SEQ ID NOS: 1 to 29 (i.e., SEQ ID NOS: 1, 3, 5 . . . 27, and 29), respectively.

The amino acid sequences shown in SEQ ID NOS: 6, 8, 10, 12 and 14 in the Sequence Listing disclosed according to the present invention are the amino acid sequences of the CAPRIN-1 proteins, which were isolated, by the SEREX method using canine testis tissue-derived cDNA libraries and sera from dogs with breast cancer, as polypeptides capable of binding to antibodies specifically existing in the sera from tumor-bearing dogs; the amino acid sequences shown in SEQ ID NOS: 2 and 4 are the amino acid sequences of the CAPRIN-1 proteins isolated as human homologs of said dog polypeptides; the amino acid sequence shown in SEQ ID NO: 16 is the amino acid sequence of the CAPRIN-1 protein isolated as a bovine homolog of said dog polypeptide; the amino acid sequence shown in SEQ ID NO: 18 is the amino acid sequence of the CAPRIN-1 protein isolated as an equine homolog of said dog polypeptide; the amino acid sequences shown in (even-numbered) SEQ ID NOS: 20 to 28 are the amino acid sequences of the CAPRIN-1 proteins isolated as murine homologs of said dog polypeptides; and the amino acid sequence shown in SEQ ID NO: 30 is the amino acid sequence of the CAPRIN-1 protein isolated as a chicken homolog of said dog polypeptide (see Example 1 described below). CAPRIN-1 is known to be expressed when activation or cell division of normal cells in resting phase takes place.

It was known that CAPRIN-1 was not expressed on the surface of cells. However, as a result of examination in connection with the present invention, it has been now revealed that certain portions of CAPRIN-1 protein are expressed on the surfaces of various cancer cells. According to the present invention, an antibody that binds to a portion within CAPRIN-1 protein expressed on cancer cell surfaces is preferably used. Examples of the partial peptides within CAPRIN-1 protein expressed on cancer cell surfaces include polypeptides consisting of a sequence of 7 or more consecutive amino acids in the region of the amino acid residue Nos. (or the amino acids (aa)) 50-98 or the amino acid residue Nos. (aa) 233-305 in an amino acid sequence shown in any one of the even-numbered SEQ ID NOS: 2 to 30, excluding SEQ ID NOS: 6 and 18, in the Sequence Listing. Specific examples thereof include the amino acid sequence shown in SEQ ID NO: 37 or 136 (preferably, the region of the amino acid sequence shown in SEQ ID NO: 137 or 138 in the amino acid sequence shown in SEQ ID NO: 136), or an amino acid sequence having 80% or more, preferably 85% or more, more preferably 90% or more, and further preferably 95% or more sequence identity with said amino acid sequences. Antibodies of the present invention include all antibodies capable of binding to the above peptides and having antitumor activity.

The antibodies to CAPRIN-1 usable in the present invention as described above may be any types thereof, as long as they can exhibit antitumor activity. Examples thereof include monoclonal antibodies, polyclonal antibodies, synthetic antibodies, multispecific antibodies, human antibodies, humanized antibodies, chimeric antibodies, single-chain antibodies (scFV), and fragments thereof such as Fab and $F(ab')_2$. These antibodies and fragments thereof can be prepared by methods known to persons skilled in the art. In the present invention, antibodies capable of specifically binding to a CAPRIN-1 protein are desirable. Such antibodies are preferably monoclonal antibodies; however, as long as homogenous antibodies can be stably produced, polyclonal antibodies may also be used. In addition, if the subject is a human, a human antibody or a humanized antibody is desirable in order to avoid or inhibit the immunorejection.

The word "specifically binding to a CAPRIN-1 protein" as used herein means that an antibody of interest specifically binds to the CAPRIN-1 protein and does not substantially bind to other proteins.

As described below, the antitumor activity of an antibody used in the present invention can be evaluated by examining in vivo the inhibition of tumor growth in a tumor-bearing animal, or examining in vitro whether or not the immunocyte- or complement-mediated cytotoxic activity against tumor cells expressing the polypeptide is exhibited.

Moreover, the subjects in need of treatment and/or prevention of cancer according to the present invention are mammals such as human, pet animals, livestock animals, or sport animals. The preferred subject is a human.

Production of antigens, production of antibodies, and pharmaceutical compositions, related to the present invention, will be explained below.

<Production of Antigens Used for Antibody Production>

Proteins or fragments thereof used as sensitizing antigens for obtaining antibodies to CAPRIN-1 used in the present invention are not limited in terms of their origins such as animals including, for example, humans, canines, bovines, horses, mice, rats, and chickens. However, such proteins or fragments thereof are preferably selected in view of compatibility with parent cells used for cell fusion. Mammal-derived proteins are generally preferable and human-derived proteins are particularly preferable. For instance, if the CAPRIN-1 is human CAPRIN-1, a human CAPRIN-1 protein, a partial peptide thereof, or cells capable of expressing human CAPRIN-1 can be used.

Nucleotide sequences and amino acid sequences of human CAPRIN-1 and homologs thereof can be obtained by, for example, accessing GenBank (NCBI, USA) and using the BLAST or FASTA algorithm (Karlin and Altschul, Proc. Natl. Acad. Sci. USA, 90:5873-5877, 1993; Altschul et al., Nucleic Acids Res. 25:3389-3402, 1997).

According to the present invention, when the nucleotide sequence (SEQ ID NO: 1 or 3) or the amino acid sequence (SEQ ID NO: 2 or 4) of human CAPRIN-1 is used as a base sequence, targets are nucleic acids or proteins each consisting of a sequence having 70% to 100%, preferably 80% to 100%, more preferably 90% to 100%, and further preferably 95% to 100% (e.g., 97% to 100%, 98% to 100%, 99% to 100%, or 99.5% to 100%) sequence identity with the nucleotide sequence or amino acid sequence of the ORF or mature portion of the base nucleotide sequence or amino acid sequence. The term "% sequence identity" as used herein means a percentage (%) of the number of identical amino acids (or nucleotides) to the total number of amino acids (or nucleotides) in the case that two sequences are aligned such that maximum similarity can be achieved with or without introduction of gaps.

Fragments of a CAPRIN-1 protein have lengths ranging from the amino acid length of an epitope (or an antigenic determinant), which is the smallest unit of an antigen recognized by an antibody, to less than the full-length of the protein. The epitope refers to a polypeptide fragment having antigenicity or immunogenicity in mammals and preferably in humans. The smallest unit of polypeptide fragment consists of approximately 7 to 12 amino acids, and for example, 8 to 11 amino acids. A specific example thereof is the amino acid sequence shown in SEQ ID NO: 37, SEQ ID NO: 137, or SEQ ID NO: 138, or an amino acid sequence having 80% or more, preferably 85% or more, more preferably 90% or more, and further preferably 95% or more sequence identity with said amino acid sequence.

Polypeptides comprising the aforementioned human CAPRIN-1 protein and partial peptides thereof can be synthesized according to chemical synthesis methods such as the Fmoc method (fluorenylmethyloxycarbonyl method) or the tBoc method (t-butyloxycarbonyl method) (the Japanese Biochemical Society (ed.), "Biochemical Experimentation Course (*Seikagaku Jikken Koza*) 1," Protein Chemistry IV, Chemical Modification and Peptide Synthesis, Kagaku-dojin Publishing Company, Inc. (Japan), 1981). Also, they can be synthesized by general methods using a variety of commercially available peptide synthesizers. In addition, polypeptides of interest can be obtained by preparing polynucleotides encoding the above polypeptides using known gene engineering methods (Sambrook et al., Molecular Cloning, 2nd edition, Current Protocols in Molecular Biology (1989), Cold Spring Harbor Laboratory Press; Ausubel et al., Short Protocols in Molecular Biology, 3rd edition, A Compendium of Methods from Current Protocols in Molecular Biology (1995), John Wiley & Sons, etc.), incorporating each of the polynucleotides into an expression vector and introducing the vector into a host cell, thereby allowing the host cell to produce the polypeptide. By such a way, the desired polypeptides can be obtained.

Polynucleotides encoding the aforementioned polypeptides can be readily prepared by known gene engineering techniques or general methods using commercially available nucleic acid synthesizers. For example, DNA comprising the nucleotide sequence shown in SEQ ID NO: 1 can be prepared by PCR using a human chromosome DNA or cDNA library as a template and a pair of primers designed to enable the amplification of the nucleotide sequence shown in SEQ ID NO: 1. PCR conditions can be appropriately determined. For example, such conditions may comprise conducting 30 cycles of the reaction steps (as one cycle) consisting of: 94° C., 30 seconds (denaturation); 55° C., 30 seconds to 1 minute (annealing); and 72° C., r 2 minutes (elongation) using a thermostable DNA polymerase (e.g., Taq polymerase) and a $Mg^{2+}$-containing PCR buffer, followed by reaction at 72° C. for 7 minutes after completion of the 30 cycles. However, the present invention is not limited to the above-exemplified PCR conditions. PCR techniques and conditions are described in, for example, Ausubel et al., Short Protocols in Molecular Biology, 3rd edition, A Compendium of Methods from Current Protocols in Molecular Biology (1995), John Wiley & Sons (Chapter 15, in particular).

In addition, desired DNA can be isolated by preparing appropriate probes and primers based on information about the nucleotide and amino acid sequences shown in SEQ ID NOS: 1 to 30 in the Sequence Listing described herein, and screening a human cDNA library or the like with the use of such probes and primers. Preferably, such cDNA library is produced from a cell, organ, or tissue in which the protein with any one of the even-numbered SEQ ID NOS: 2 to 30 is expressed. Examples of the cell or tissue include cells or tissues from testis and cancers or tumors, such as leukemia, breast cancer, lymphoma, brain tumor, lung cancer, and colon cancer. Operations such as preparation of probes or primers, construction of cDNA libraries, screening of cDNA libraries, and cloning of genes of interest, as described above, are known to persons skilled in the art, and they can be carried out according to, for example, the methods described in Sambrook et al., Molecular Cloning, the 2nd edition, Current Protocols in Molecular Biology (1989) and Ausbel et al. (ibid.). DNAs encoding human CAPRIN-1 protein and partial peptides thereof can be obtained from the thus obtained DNAs.

The above-described host cells may be any cells, as long as they can express the above-described polypeptides. An example of prokaryotic host cell includes, but is not limited to, *Escherichia coli*. Examples of eukaryotic host cells include, but are not limited to, mammalian cells such as monkey kidney cell (COS1), Chinese hamster ovary cell (CHO), human embryonic kidney cell line (HEK293), and mouse embryonic skin cell line (NIH3T3), yeast cells such as budding yeast and dividing yeast cells, silkworm cells, and *Xenopus* egg cells.

When prokaryotic cells are used as host cells, an expression vector having an origin replicable in prokaryotic cells, a promoter, a ribosome-binding site, a multicloning site, a terminator, a drug resistance gene, an auxotrophic complementary gene, or the like can be used. As expression vectors for *Escherichia coli*, pUC vectors, pBluescriptII, pET expression systems, pGEX expression systems, and the like can be exemplified. A DNA encoding the above polypeptide is incorporated into such an expression vector, a prokaryotic host cell is transformed with the vector, and then the thus obtained transformed cell is cultured, so that the polypeptide encoded by the DNA can be expressed in the prokaryotic host cell. At this time, the polypeptide can also be expressed as a fusion protein with another protein.

When eukaryotic cells are used as host cells, expression vectors for eukaryotic cells having a promoter, a splicing region, a poly(A) addition site, or the like can be used. Examples of such expression vectors include pKA1, pCDM8, pSVK3, pMSG, pSVL, pBK-CMV, pBK-RSV, EBV vector, pRS, pcDNA3, and pYES2. By similar procedures to those mentioned above, a DNA encoding the aforementioned polypeptide is incorporated into such an expression vector, an eukaryotic host cell is transformed with the vector, and then the thus obtained transformed cell is cultured, so that the polypeptide encoded by the above DNA can be expressed in the eukaryotic host cell. When pIND/V5-His, pFLAG-CMV-2, pEGFP-N1, pEGFP-C1, or the like is used as an expression vector, the above polypeptide may be expressed as a fusion protein with a tag, such as His tag (e.g., $(His)_6$ to $(His)_{10}$), FLAG tag, myc tag, HA tag, or GFP.

For introduction of an expression vector into a host cell, well known methods can be employed, such as electroporation, a calcium phosphate method, a liposome method, a DEAE dextran method, microinjection, viral infection, lipofection, and binding with a cell-membrane-permeable peptide.

Isolation and purification of a polypeptide of interest from host cells can be performed using known isolation techniques in combination. Examples of such known techniques include, but are not limited to, treatment using a denaturing agent such as urea or a surfactant, ultrasonication, enzymatic digestion, salting-out, solvent fractionation and precipitation, dialysis, centrifugation, ultrafiltration, gel filtration, SDS-PAGE, isoelectric focusing electrophoresis, ion exchange chromatography, hydrophobic chromatography, affinity chromatography, and reverse phase chromatography.

<Structure of Antibody>

In general, antibodies are heteromultimeric glycoproteins each comprising at least two heavy chains and two light chains. Meanwhile, antibodies except for IgM are heterotetrameric glycoproteins (approximately 150 kDa) each comprising two identical light (L) chains and two identical heavy (H) chains. Typically, each light chain is connected to a heavy chain via a single covalent disulfide bond. However, the number of disulfide bonds between heavy chains varies among different immunoglobulin isotypes. Each of heavy chain and light chain also has an intrachain disulfide bond(s). Each heavy chain has a variable domain (VH region) at one end thereof, to which some constant regions are bound in series. Each light chain has a variable domain (VL region) at one end thereof and has a single constant region at the opposite end thereof. The constant region of a light chain is aligned with the first constant region of a heavy chain and the light-chain variable domain is aligned with the heavy-chain variable domain. A specific region of an antibody variable domain, which is called "complementarity determining region (CDR)," exhibits specific variability so as to impart binding specificity to an antibody. A relatively conserved portion in a variable region is called a "framework region (FR)." A complete heavy-chain or light-chain variable domain comprises 4 FRs connected to each other via 3 CDRs. Such CDRs are called "CDRH1," "CDRH2," and "CDRH3," respectively, in such order from the N-terminus in a heavy chain. Similarly, for a light chain, they are called "CDRL1," "CDRL2," and "CDRL3," respectively. CDRH3 plays the most important role in terms of antibody-antigen binding specificity. In addition, CDRs in each chain are retained by FR regions in the state that they are close to each other, and they contribute to the formation of antibody-antigen binding sites with CDRs in a corresponding chain. Constant regions do not directly contribute to antibody-antigen binding. However, they exhibit various effector functions such as association with antibody-dependent cell-mediated cytotoxicity (ADCC), phagocytosis through binding to an Fcγ receptor, half-life/clearance rate via an neonatal Fc receptor (FcRn), and complement-dependent cytotoxicity (CDC) via a C1q component in the complement cascade.

<Antibody Production>

The term "anti-CAPRIN-1 antibody" used in the present invention refers to an antibody having an immunological reactivity with a full-length CAPRIN-1 protein or a fragment thereof.

The term "immunological reactivity" used herein indicates the characteristics of an antibody binding in vivo to a CAPRIN-1 antigen. The tumor-damaging function (e.g., death, inhibition, or regression) can be expressed as a result of such binding. Specifically, any type of antibody may be used in the present invention as long as the antibody can bind to a CAPRIN-1 protein to damage a tumor or a cancer such as leukemia, lymphoma, breast cancer, brain tumor, lung cancer, esophageal cancer, gastric cancer, kidney cancer, or colon cancer.

Examples of such antibodies include monoclonal antibodies, polyclonal antibodies, synthetic antibodies, multispecific antibodies, human antibodies, humanized antibodies, chimeric antibodies, single-chain antibodies, and antibody fragments (e.g., Fab and $F(ab')_2$). In addition, examples of arbitrary immunoglobulin classes of such antibodies include IgG, IgE, IgM, IgA, IgD, and IgY, and examples of arbitrary immunoglobulin subclasses include IgG1, IgG2, IgG3, IgG4, IgA1, and IgA2.

Antibodies may be further modified via acetylation, formylation, amidation, phosphorylation, or pegylation (PEG), in addition to glycosylation.

Production examples for a variety of antibodies are described below.

In a case in which an antibody of interest is a monoclonal antibody, a breast cancer SK-BR-3 cell line expressing CAPRIN-1 or the like is administered to mice for immunization, followed by extraction of spleens from the mice. Cells are separated from each spleen and then are fused with mouse myeloma cells. Clones capable of producing an antibody having cancer cell growth inhibition action are selected from the obtained fusion cells (hybridomas). A monoclonal antibody-producing hybridoma having cancer cell growth inhibition action is isolated and cultured. An antibody of interest can be prepared via purification from the culture supernatant by a general affinity purification method.

Also, a monoclonal antibody-producing hybridoma can be produced in a manner described below, for example. First, an animal is immunized with a sensitizing antigen by a known method. In a general method, immunization is carried out by intraperitoneally or subcutaneously injecting a sensitizing antigen into a mammal. Specifically, a sensitizing antigen is diluted with or suspended in PBS (Phosphate-Buffered Saline), physiological saline, or the like to an appropriate resultant amount. If desired, an appropriate amount of a conventional adjuvant (e.g., Freund's complete adjuvant) is mixed therewith. After emulsification takes place, the resultant is administered to a mammal several times every 4 to 21 days. In addition, an adequate carrier can be used for immunization with a sensitizing antigen.

As described above, after immunization of a mammal and confirmation of an increase to a desired antibody level in serum, immunocytes are collected from the mammal and subjected to cell fusion. Particularly preferable examples of immunocytes are splenocytes.

Mammalian myeloma cells are used as relevant parent cells subjected to fusion with the above immunocytes. For such myeloma cells, the following various examples of known cell lines are preferably used: P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976). 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S. J. Exp. Med. (1978) 148, 313-323), and 8210 (Galfre, G. et al., Nature (1979) 277, 131-133).

Basically, cell fusion of immunocytes and myeloma cells described above can be carried out according to a known method such as the method of Kohler and Milstein et al. (Kohler, G. and Milstein, C. Methods Enzymol. (1981) 73, 3-46).

More specifically, cell fusion described above is carried out in the presence of a cell fusion promoter in a conventional nutrients-containing culture solution, for example. Examples of a fusion promoter to be used include polyethylene glycol (PEG) and Sendai virus (HVJ: hemagglutinating virus of Japan). If desired, an adjuvant such as dimethylsulfoxide may be further added for improvement of fusion efficiency.

The proportion of immunocytes used to that of myeloma cells used can be arbitrarily determined. For example, the ratio of immunocytes to myeloma cells is preferably 1:1 to 10:1. Examples of a culture solution that can be used for cell fusion described above include an RPMI1640 culture solution and an MEM culture solution adequate for growth of the above myeloma cell lines as well as other conventional culture solutions used for this kind of cell culture. Further, a serum replacement such as fetal calf serum (FCS) can be used in combination therewith.

For cell fusion, the above immunocytes and myeloma cells are sufficiently mixed at predetermined amounts in the culture solution. A PEG solution (e.g., average molecular weight: approximately 1000 to 6000) that has been previously heated to approximately 37° C. is added thereto at a concentration of generally 30% to 60% (w/v), followed by mixing. This results in formation of hybridomas of interest. Subsequently, operational steps of sequential addition of an appropriate culture solution and removal of the supernatant via centrifugation are repeatedly carried out to remove cell fusion agent(s) and the like that are not preferable for the growth of hybridomas.

The thus obtained hybridomas are cultured in a conventional selection culture solution such as an HAT culture solution (a culture solution comprising hypoxanthine, aminopterin, and thymidine) for selection. Culture in such an HAT culture solution is continuously carried out for a sufficient time period (generally several days to several weeks) for death of cells (non-fused cells) other than hybridomas of interest. Next, a conventional limiting dilution method is employed to screen for hybridomas producing antibodies of interest and to carry out single cloning.

Further, it is also possible to obtain human antibody-producing hybridomas having desired activity (e.g., cell growth inhibition activity) in the following manner, as well as to obtain the above hybridomas via immunization of non-human animals with antigens. Human lymphocytes (e.g., human lymphocytes infected with EB virus) are sensitized in vitro with a protein, protein-expressing cells, or a lysate thereof and sensitized lymphocytes are fused with human-derived myeloma cells having the ability to permanently divide (e.g., U266) (registration no. TIB 196).

Monoclonal antibody-producing hybridomas produced as above can be subcultured in a conventional culture solution. In addition, they can be preserved in liquid nitrogen for a long period of time.

Specifically, immunization is carried out using a desired antigen or cells expressing a desired antigen as sensitizing antigen(s) according to a conventional immunization method. The obtained immunocytes are fused with known parent cells by a conventional cell fusion method. Then, monoclonal antibody-producing cells (hybridomas) are screened for by a conventional screening method. Thus, antibody production can be carried out.

Other examples of antibodies that can be used in the present invention include polyclonal antibodies. For example, polyclonal antibodies can be used in a manner described below.

Serum is obtained by immunizing small animals such as mice, human antibody-producing mice, or rabbits with a naturally occurring CAPRIN-1 protein, a recombinant CAPRIN-1 protein that has been expressed as a protein fused with GST or the like in a microorganism such as *Escherichia coli*, or a partial peptide thereof. The serum is purified via ammonium sulfate precipitation, protein A/protein G column chromatography, DEAE ion-exchange chromatography, affinity column chromatography with a column to which a CAPRIN-1 protein or a synthetic peptide is coupled, or a similar technique for preparation of polyclonal antibodies. In the Examples described below, a rabbit polyclonal antibody was produced, and antitumor effects thereof were confirmed, such antibody being against a partial peptide (with the sequence shown in SEQ ID NO: 37) of a domain in a CAPRIN-1 protein amino acid sequence that is expressed on cancer cell surfaces.

A known human antibody-producing mouse used herein is, for example, a KM Mouse (Kirin Pharma/Medarex) or a XenoMouse (Amgen) (e.g., WO02/43478 and WO02/092812). When such mice are immunized with CAPRIN-1 proteins or fragments thereof, complete human polyclonal antibodies can be obtained from blood. In addition, human monoclonal antibodies can be produced by a method of fusing splenocytes collected from immunized mice with myeloma cells.

Antigen preparation can be carried out in accordance with a method such as a method using animal cells (JP Patent Publication (Kohyo) No. 2007-530068) or a method using a baculovirus (e.g., WO98/46777). If the immunogenicity of an antigen is low, an antigen is bound to a macromolecule having immunogenicity, such as albumin. Then, the antigen can be used for immunization.

Further, it is possible to use a gene recombinant antibody produced by cloning an antibody gene from a hybridoma, incorporating the clone into an adequate vector, introducing the vector into a host, and using a gene recombinant technique. (See, for example, Carl, A. K. Borrebaeck, James, W. Larrick, THERAPEUTIC MONOCLONAL ANTIBODIES, Published in the United Kingdom by MACMILLAN PUBLISHERS LTD, 1990.) Specifically, cDNA of a variable region (V region) of an antibody is synthesized from mRNA of a hybridoma with the use of a reverse transcriptase. After DNA encoding a V region of an antibody of interest is obtained, such DNA is ligated to desired DNA encoding an antibody constant region (C region). The resultant is incorporated into an expression vector. Alternatively, DNA encoding an antibody V region may be incorporated into an expression vector comprising DNA of an antibody C region. Such DNA is incorporated into an expression vector in a manner such that it is expressed under control of an expression control region such as an enhancer or a promoter. Next, host cells are transformed with such expression vector, thereby allowing the antibody to be expressed.

Anti-CAPRIN-1 antibodies of the present invention are preferably monoclonal antibodies. However, they may be polyclonal antibodies, gene-modified antibodies (such as chimeric antibodies and humanized antibodies), and the like.

Monoclonal antibodies include human monoclonal antibodies and non-human animal monoclonal antibodies (e.g., mouse monoclonal antibodies, rat monoclonal antibodies, rabbit monoclonal antibodies, and chicken monoclonal antibodies). Monoclonal antibodies can be produced by culturing hybridomas obtained via fusion of myeloma cells and splenocytes from non-human mammals (e.g., mice or human antibody-producing mice) immunized with CAPRIN-1 proteins. In the Examples described below, mouse monoclonal antibodies were produced and antitumor effects thereof were confirmed. Such a monoclonal antibody comprises a heavy-chain variable (VH) region having the amino acid sequence shown in SEQ ID NO: 43, SEQ ID NO: 73, SEQ ID NO: 83, SEQ ID NO: 93, SEQ ID NO: 103, SEQ ID NO: 113, or SEQ ID NO: 123 and a light-chain variable (VL) region having the amino acid sequence shown in SEQ ID NO: 47, SEQ ID NO: 53, SEQ ID NO: 58, SEQ ID NO: 63, SEQ ID NO: 68, SEQ ID NO: 77, SEQ ID NO: 87, SEQ ID NO: 97, SEQ ID NO: 107, SEQ ID NO: 117, or SEQ ID NO: 127. Here, the VH region comprises: CDR1 represented by the amino acid sequence of SEQ ID NO: 40, SEQ ID NO: 70, SEQ ID NO: 80, SEQ ID NO: 90, SEQ ID NO: 100, SEQ ID NO: 110, or SEQ ID NO: 120; CDR2 represented by the amino acid sequence of SEQ ID NO: 41, SEQ ID NO: 71, SEQ ID NO: 81, SEQ ID NO: 91, SEQ ID NO: 101, SEQ ID NO: 111, or SEQ ID NO: 121; and CDR3 represented by the amino acid sequence of SEQ ID NO: 42, SEQ ID NO: 72, SEQ ID NO: 82, SEQ ID NO: 92, SEQ ID NO: 102, SEQ ID NO: 112, or SEQ ID NO: 122. The VL region comprises: CDR1 represented by the amino acid sequence of SEQ ID NO: 44, SEQ ID NO: 50, SEQ ID NO: 55, SEQ ID NO: 60, SEQ ID NO: 65, SEQ ID NO: 74, SEQ ID NO: 84, SEQ ID NO: 94, SEQ ID NO: 104, SEQ ID NO: 114, or SEQ ID NO: 124; CDR2 represented by the amino acid sequence of SEQ ID NO: 45, SEQ ID NO: 51, SEQ ID NO: 56, SEQ ID NO: 61, SEQ ID NO: 66, SEQ ID NO: 75, SEQ ID NO: 85, SEQ ID NO: 95, SEQ ID NO: 105, SEQ ID NO: 115, or SEQ ID NO: 125; and CDR3 represented by the amino acid sequence of SEQ ID NO: 46, SEQ ID NO: 52, SEQ ID NO: 57, SEQ ID NO: 62, SEQ ID NO: 67, SEQ ID NO: 76, SEQ ID NO: 86, SEQ ID NO: 96, SEQ ID NO: 106, SEQ ID NO: 116, or SEQ ID NO: 126.

A chimeric antibody is an antibody produced by combining sequences from different animals. An example thereof is an antibody consisting of mouse antibody heavy-chain and light-chain variable regions and human antibody heavy-chain and light-chain constant regions. Such a chimeric antibody can be produced by a known method. For example, it can be obtained by ligating DNA encoding an antibody V region to DNA encoding a human antibody C region, incorporating the resultant into an expression vector, and introducing the vector into a host for antibody production.

Polyclonal antibodies include antibodies obtained by immunizing human antibody-producing animals (e.g., mice) with CAPRIN-1 proteins.

A humanized antibody is a modified antibody, and it is sometimes referred to as a "reshaped human antibody." It is known that a humanized antibody is constructed by transplanting CDRs of an immunized animal-derived antibody into complementarity determining regions of a human antibody. Also, a general gene recombinant technique therefor is known.

Specifically, a DNA sequence designed in a manner that allows mouse antibody CDRs to be ligated to human antibody framework regions (FRs) is synthesized by the PCR method using several oligonucleotides prepared in such a manner that the oligonucleotides have portions overlapping each other at one end of each thereof. A humanized antibody can be obtained by ligating the above obtained DNA to DNA encoding a human antibody constant region, incorporating the resultant into an expression vector, and introducing the vector into a host for antibody production (see EP-A-239400 and WO96/02576). Human antibody FRs ligated to each other via CDRs are selected on the assumption that complementarity determining regions can form a good antigen binding site. If necessary, amino acids in framework regions of an antibody variable region may be substituted in such a manner that complementarity determining regions in a reshaped human antibody form an appropriate antigen binding site (Sato K. et al., Cancer Research 1993, 53: 851-856). In addition, the framework regions may be substituted with framework regions from a different human antibody (see WO99/51743).

Human antibody framework regions ligated to each other via CDRs are selected on the assumption that complementarity determining regions can form good antigen binding sites. If necessary, amino acids in framework regions of an antibody variable region may be substituted in such a manner that complementarity determining regions in reshaped human antibody form an appropriate antigen binding sites (Sato K. et al., Cancer Research 1993, 53: 851-856).

After a chimeric antibody or a humanized antibody is produced, amino acids in a variable region (e.g., FR) or a constant region may be substituted, for example, with different amino acids.

Here, the amino acid substitution is a substitution of for example, less than 15, less than 10, not more than 8, not more than 7, not more than 6, not more than 5, not more than 4, not more than 3, or not more than 2 amino acids, preferably 1 to 5 amino acids, and more preferably 1 or 2 amino acids. A substituted antibody should be functionally equivalent to an unsubstituted antibody. The substitution is preferably a conservative amino acid substitution, which is a substitution between amino acids having similar characteristics in terms of charge, side chains, polarity, aromaticity, and the like. For example, characteristically similar amino acids can be classified into the following types: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched-chain amino acids (threonine, valine, isoleucine); and aromatic amino acids (phenylalanine, tyrosine, tryptophan, and histidine).

An example of an antibody modifier is an antibody bound to a molecule such as polyethylene glycol (PEG). Regarding antibody modifiers of the present invention, substances that bind to an antibody are not limited. Such an antibody modifier can be obtained by chemically modifying an obtained antibody. A method of such modification has been already established in the field related to the present invention.

The expression "functionally equivalent" used herein indicates a situation in which an antibody of interest has biological or biochemical activity similar to that of an antibody of the present invention. Specifically, such antibody has a function of damaging tumors and causes essentially no rejection reaction when applied to humans. An example of such activity is cell growth inhibition activity or binding activity.

A known method for preparing a polypeptide functionally equivalent to a given polypeptide that is well known to persons skilled in the art is a method comprising introducing a mutation into a polypeptide. For instance, a person skilled in the art can adequately introduce a mutation into an antibody of the present invention using a site-specific mutagenesis method (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. USA. 82, 488-492; or Kunkel (1988) Methods Enzymol. 85, 2763-2766) or a similar method. Thus, an antibody functionally equivalent to the antibody of the present invention can be prepared.

An aforementioned antibody capable of recognizing an epitope of a CAPRIN-1 protein recognized by an anti-CAPRIN-1 antibody can be obtained by a method known to persons skilled in the art. For example, it can be obtained by: a method comprising determining an epitope of a CAPRIN-1 protein recognized by an anti-CAPRIN-1 antibody by a general method (e.g., epitope mapping) and producing an antibody using a polypeptide having an amino acid sequence contained in the epitope as an immunogen; or a method comprising determining an epitope of an antibody produced by a general method and selecting an antibody having an epitope identical to an epitope of an anti-CAPRIN-1 antibody. Here, the term "epitope" refers to a polypeptide fragment having antigenicity or immunogenicity in mammals and preferably in humans. The smallest unit thereof consists of approximately 7 to 12 amino acids and preferably 8 to 11 amino acids.

The affinity constant Ka ($k_{on}/k_{off}$) of an antibody of the present invention is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

An antibody of the present invention can be conjugated with an antitumor agent. Binding between an antibody and an antitumor agent can be carried out via a spacer having a group reactive to an amino group, a carboxyl group, a hydroxy group, a thiol group, or the like (e.g., an imidyl succinate group, a formyl group, a 2-pyridyldithio group, a maleimidyl group, an alkoxycarbonyl group, or a hydroxy group).

Examples of antitumor agents include the following antitumor agents known in references or the like: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, ADRIAMYCIN, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, capecitabine, and pharmacologically acceptable salts or derivatives thereof.

Alternatively, it is also possible to bind a radioactive isotope such as $^{211}At$, $^{131}I$, $^{125}I$, $^{90}Y$, $^{186}Re$, $^{188}Re$, $^{153}Sm$, $^{212}Bi$, $^{32}P$, $^{175}Lu$, or $^{176}Lu$ known in references and the like to an antibody of the present invention. It is desirable for such radioactive isotopes to be effective for tumor treatment or diagnosis.

An antibody of the present invention is an antibody having an immunological reactivity with CAPRIN-1 or an antibody capable of specifically recognizing CAPRIN-1. Such an antibody should be an antibody having a structure that allows a subject animal to which the antibody is administered to completely or almost completely avoid a rejection reaction. If the subject animal is a human, examples of the above antibody include human antibodies, humanized antibodies, chimeric antibodies (e.g., human-mouse chimeric antibodies), single-chain antibodies, and bispecific antibodies. Such an antibody is a recombinant antibody having human antibody-derived heavy-chain and light-chain variable regions, a recombinant antibody having heavy-chain and light-chain variable regions each consisting of non-human animal antibody-derived complementarity determining regions (CDR1, CDR2, and CDR3) and human antibody-derived framework regions, or a recombinant antibody having non-human animal antibody-derived heavy-chain and light-chain variable regions and human antibody-derived heavy-chain and light-chain constant regions. The first two antibodies are preferable.

The above recombinant antibody can be produced in the manner described below. DNA encoding a monoclonal antibody against human CAPRIN-1 (e.g., a human monoclonal antibody, a mouse monoclonal antibody, a rat monoclonal antibody, a rabbit monoclonal antibody, or a chicken monoclonal antibody) is cloned from an antibody-producing cell such as a hybridoma. DNAs encoding a light-chain variable region and a heavy-chain variable region of the antibody are produced by an RT-PCR method or the like using the obtained clone as a template. Then, the sequences of a light-chain variable region and a heavy-chain variable region or the sequences of CDR1, CDR2, and CDR3 are determined by the Kabat EU numbering system (Kabat et al., Sequences of Proteins of Immunological Interest, 5th Ed. Public Health Service, National Institute of Health, Bethesda, Md. (1991)).

Further, such DNAs encoding variable regions or DNAs encoding CDRs are produced by a gene recombinant technique (Sambrook et al., Molecular Cloning A Laboratory Manual, Cold Spring Harbor Laboratory Press (1989)) or a DNA synthesizer. Here, the above human monoclonal antibody-producing hybridoma can be produced by immunizing a human antibody-producing animal (e.g., a mouse) with human CAPRIN-1 and fusing splenocytes from the spleen removed from the animal with myeloma cells. In addition to the above, if necessary, DNAs encoding human antibody-derived light-chain or heavy-chain variable regions and constant regions are produced by a gene recombinant technique or a DNA synthesizer.

In the case of a humanized antibody, DNA in which the CDR coding sequences in a DNA encoding a human antibody-derived light-chain or heavy-chain variable region have been substituted with corresponding CDR coding sequences of an antibody from a non-human animal (e.g., a mouse, a rat, or a chicken) is produced. The DNA obtained as above is ligated to the DNA encoding a constant region of a human antibody-derived light chain or heavy chain. Thus, DNA encoding a humanized antibody can be produced.

In the case of a chimeric antibody, DNA encoding an antibody light-chain or heavy-chain variable region from a non-human animal (e.g., a mouse, a rat, or a chicken) is ligated to the DNA encoding a human antibody-derived light-chain or heavy-chain constant region. Thus, DNA encoding a chimeric antibody can be produced.

A single-chain antibody is an antibody in which a heavy-chain variable region and a light-chain variable region are linearly ligated to each other via a linker. DNA encoding a single-chain antibody can be produced by binding DNA encoding a heavy-chain variable region, DNA encoding a linker, and a DNA encoding a light-chain variable region. Here, a heavy-chain variable region and a light-chain variable region are those from a human antibody or those from a human antibody in which CDRs alone have been substituted with CDRs of an antibody from a non-human animal (e.g., a mouse, a rat, or a chicken). In addition, the linker consists of 12 to 19 amino acids. An example thereof is $(G_4S)_3$ consisting of 15 amino acids (G. B. Kim et al., Protein Engineering Design and Selection 2007, 20 (9): 425-432).

A bispecific antibody (diabody) is an antibody capable of specifically binding to two different epitopes in which, for example, DNA encoding a heavy-chain variable region A, DNA encoding a light-chain variable region B, DNA encoding a heavy-chain variable region B, and DNA encoding a light-chain variable region A are bound to each other in such order (provided that DNA encoding a light-chain variable region B and DNA encoding a heavy-chain variable region B are bound to each other via DNA encoding a linker described above). Thus, DNA encoding a bispecific antibody can be produced. Here, both a heavy-chain variable region and a light-chain variable region are those from a human antibody or those from a human antibody in which CDRs alone have been substituted with CDRs of an antibody from a non-human animal (e.g., a mouse, a rat, or a chicken).

Recombinant DNA produced as above is incorporated into one or a plurality of appropriate vector(s). Each such vector is introduced into a host cell (e.g., a mammal cell, a yeast cell, or an insect cell) for (co)expression. Thus, a recombinant antibody can be produced (P. J. Delves, ANTIBODY PRODUCTION ESSENTIAL TECHNIQUES, 1997 WILEY, P. Shepherd and C. Dean, Monoclonal Antibodies, 2000 OXFORD UNIVERSITY PRESS; J. W. Goding, Monoclonal Antibodies: Principles and Practice, 1993 ACADEMIC PRESS).

Examples of an antibody of the present invention produced by the above method include the following antibodies (a) to (k).

(a) An antibody comprising a heavy-chain variable region comprising the sequences shown in SEQ ID NOS: 40, 41, and 42 and a light-chain variable region comprising the sequences shown in SEQ ID NOS: 44, 45, and 46 (and preferably an antibody composed of a heavy-chain variable region of SEQ ID NO: 43 and a light-chain variable region of SEQ ID NO: 47).

(b) An antibody comprising a heavy-chain variable region comprising the sequences shown in SEQ ID NOS: 40, 41, and 42 and a light-chain variable region comprising the sequences shown in SEQ ID NOS: 50, 51, and 52 (and preferably an antibody composed of a heavy-chain variable region of SEQ ID NO: 43 and a light-chain variable region of SEQ ID NO: 53).

(c) An antibody comprising a heavy-chain variable region comprising the sequences shown in SEQ ID NOS: 40, 41, and 42 and a light-chain variable region comprising the sequences shown in SEQ ID NOS: 55, 56, and 57 (and preferably an antibody composed of a heavy-chain variable region of SEQ ID NO: 43 and a light-chain variable region of SEQ ID NO: 58).

(d) An antibody comprising a heavy-chain variable region comprising the sequences shown in SEQ ID NOS: 40, 41, and 42 and a light-chain variable region comprising the sequences shown in SEQ ID NOS: 60, 61, and 62 (and preferably an antibody composed of a heavy-chain variable region of SEQ ID NO: 43 and a light-chain variable region of SEQ ID NO: 63).

(e) An antibody comprising a heavy-chain variable region comprising the sequences shown in SEQ ID NOS: 40, 41, and 42 and a light-chain variable region comprising the sequences shown in SEQ ID NOS: 65, 66, and 67 (and preferably an antibody composed of a heavy-chain variable region of SEQ ID NO: 43 and a light-chain variable region of SEQ ID NO: 68).

(f) An antibody comprising a heavy-chain variable region comprising the sequences shown in SEQ ID NOS: 70, 71, and 72 and a light-chain variable region comprising the sequences shown in SEQ ID NOS: 74, 75, and 76 (and preferably an antibody composed of a heavy-chain variable region of SEQ ID NO: 73 and a light-chain variable region of SEQ ID NO: 77).

(g) An antibody comprising a heavy-chain variable region comprising the sequences shown in SEQ ID NOS: 80, 81, and 82 and a light-chain variable region comprising the sequences shown in SEQ ID NOS: 84, 85, and 86 (and preferably an antibody composed of a heavy-chain variable region of SEQ ID NO: 83 and a light-chain variable region of SEQ ID NO: 87).

(h) An antibody comprising a heavy-chain variable region comprising the sequences shown in SEQ ID NOS: 90, 91, and 92 and a light-chain variable region comprising the sequences shown in SEQ ID NOS: 94, 95, and 96 (and preferably an antibody composed of a heavy-chain variable region of SEQ ID NO: 93 and a light-chain variable region of SEQ ID NO: 97).

(i) An antibody comprising a heavy-chain variable region comprising the sequences shown in SEQ ID NOS: 100, 101, and 102 and a light-chain variable region comprising the sequences shown in SEQ ID NOS: 104, 105, and 106 (and preferably an antibody composed of a heavy-chain variable region of SEQ ID NO: 103 and a light-chain variable region of SEQ ID NO: 107).

(j) An antibody comprising a heavy-chain variable region comprising the sequences shown in SEQ ID NOS: 110, 111, and 112 and a light-chain variable region comprising the sequences shown in SEQ ID NOS: 114, 115, and 116 (and preferably an antibody composed of a heavy-chain variable region of SEQ ID NO: 113 and a light-chain variable region of SEQ ID NO: 117).

(k) An antibody comprising a heavy-chain variable region comprising the sequences shown in SEQ ID NOS: 120, 121, and 122 and a light-chain variable region comprising the sequences shown in SEQ ID NOS: 124, 125, and 126 (and preferably an antibody composed of a heavy-chain variable region of SEQ ID NO: 123 and a light-chain variable region of SEQ ID NO: 127).

Here, amino acid sequences shown in SEQ ID NOS: 40, 41, and 42, amino acid sequences shown in SEQ ID NOS: 70, 71, and 72, amino acid sequences shown in SEQ ID NOS: 80, 81, and 82, amino acid sequences shown in SEQ ID NOS: 90, 91, and 92, amino acid sequences shown in SEQ ID NOS: 100, 101, and 102, amino acid sequences shown in SEQ ID NOS: 110, 111, and 112, or amino acid sequences shown in SEQ ID NOS: 120, 121, and 122 correspond to CDR1, CDR2, and CDR3 of mouse antibody heavy-chain variable regions, respectively. In addition, amino acid sequences shown in SEQ ID NOS: 44, 45, and 46, amino acid sequences shown in SEQ ID NOS: 50, 51, and 52, amino acid sequences shown in SEQ ID NOS: 55, 56, and 57, amino acid sequences shown in SEQ ID NOS: 60, 61, and 62, amino acid sequences shown in SEQ ID NOS: 65, 66, and 67, amino acid sequences shown in SEQ ID NOS: 74, 75, and 76, amino acid sequences shown in SEQ ID NOS: 84, 85, and 86, amino acid sequences shown in SEQ ID NOS: 94, 95, and 96, amino acid sequences shown in SEQ ID NOS: 104, 105, and 106, amino acid sequences shown in SEQ ID NOS: 114, 115, and 116, or amino acid sequences shown in SEQ ID NOS: 124, 125, and 126 correspond to CDR1, CDR2, and CDR3 of mouse antibody light-chain variable regions, respectively.

In addition, a humanized antibody, a chimeric antibody, a single-chain antibody, or a bispecific antibody of the present invention is, for example, the following antibody (i) or (ii) (an example of antibody (a) is described below).

(i) An antibody comprising: a heavy-chain variable region comprising the amino acid sequences of SEQ ID NOS: 40, 41, and 42 and an amino acid sequence of a human antibody-derived framework region; and a light-chain variable region comprising the amino acid sequences of SEQ ID NOS: 44, 45, and 46 and amino acid sequences of human antibody-derived framework regions (and preferably an antibody comprising the amino acid sequence of SEQ ID NO: 43 in a heavy-chain variable region and the amino acid sequence of SEQ ID NO: 47 in a light-chain variable region).

(ii) An antibody comprising: a heavy-chain variable region comprising the amino acid sequences of SEQ ID NOS: 40, 41, and 42 and amino acid sequences of human antibody-derived framework regions; a heavy-chain constant region comprising a human antibody-derived amino acid sequence; a light-chain variable region comprising the amino acid sequences of SEQ ID NOS: 44, 45, and 46 and amino acid sequences of human antibody-derived framework regions; and a light-chain constant region comprising a human antibody-derived amino acid sequence (and preferably an antibody comprising: a heavy-chain variable region comprising the amino acid sequence of SEQ ID NO: 43; a heavy-chain constant region comprising a human antibody-derived amino acid sequence; a light-chain variable region comprising the amino acid sequence of SEQ ID NO: 47; and a light-chain constant region comprising a human antibody-derived amino acid sequence).

In addition, sequences of human antibody heavy-chain and light-chain constant and variable regions can be obtained from, for example, NCBI (U.S.A: GenBank, UniGene, etc.). For example, the following sequences can be used as reference sequences for the corresponding regions: the sequence with registration no. J00228 for a human IgG1 heavy-chain constant region; the sequence with registration no. J00230 for a human IgG2 heavy-chain constant region; the sequence with registration no. X03604 for a human IgG3 heavy-chain constant region; the sequence with registration no. K01316 for a human IgG4 heavy-chain constant region; the sequence with registration no. V00557, X64135, or X64133 for a human light-chain κ constant region; and the sequence with registration no. X64132 or X64134 for a human light-chain λ constant region.

The above antibodies preferably have cytotoxic activity, thereby exhibiting antitumor effects.

In addition, the above specific sequences of heavy-chain and light-chain variable regions and CDRs in an antibody are merely described for exemplification. It is obvious that the present invention is not limited to particular sequences. A hybridoma capable of producing a different human antibody or a non-human animal antibody (e.g., a mouse antibody) against human CAPRIN-1 is produced. A monoclonal antibody produced by the hybridoma is collected. Then, it is determined whether or not the obtained antibody is an antibody of interest using, as indicators, immunological binding activity and cytotoxic activity with respect to human CAPRIN-1. Thus, a monoclonal antibody-producing hybridoma of interest is identified. Thereafter, as described above, DNAs encoding heavy-chain and light-chain variable regions of an antibody of interest are produced from the hybridoma for sequence determination. The DNAs are used for production of different antibodies.

Further, the above antibody of the present invention may be any one of antibodies (i) to (iv) above having a substitution, deletion, or addition of one or several (and preferably, 1 or 2) amino acid(s), particularly in a framework region sequence and/or a constant region sequence, as long as it has the specific property of specifically recognizing CAPRIN-1. Here, the term "several amino acids" indicates 2 to 5 and preferably 2 or 3 amino acids.

Furthermore, according to the present invention, DNA encoding the above antibody of the present invention, DNA encoding a heavy chain or light chain of the antibody, or DNA encoding a heavy-chain or light-chain variable region of the antibody is also provided. For instance, in the case of antibody (a), examples of such DNA include: DNA encoding a heavy-chain variable region comprising nucleotide sequences encoding the amino acid sequences of SEQ ID NOS: 40, 41, and, 42; and DNA encoding a light-chain variable region comprising nucleotide sequences encoding the amino acid sequences of SEQ ID NOS: 44, 45, and 46.

Complementarity determining regions (CDRs) encoded by DNAs of the above sequences are regions that determine antibody specificity. Therefore, sequences encoding the other regions (i.e., constant regions and framework regions) in an antibody may be sequences from a different antibody. Here, different antibodies include antibodies from non-human organisms. However, in view of reduction of side effects, human-derived antibodies are preferable. That is to say, in the above case, DNA regions encoding framework regions and constant regions of heavy and light chains preferably comprise nucleotide sequences encoding the relevant amino acid sequences from a human antibody.

Further, different examples of DNA encoding an antibody of the present invention, such as antibody (a), include DNA encoding a heavy-chain variable region comprising a nucleotide sequence encoding the amino acid sequence of SEQ ID NO: 43 and DNA in which a region encoding a light-chain variable region comprises a nucleotide sequence encoding the amino acid sequence of SEQ ID NO: 47. Here, an example of a nucleotide sequence encoding the amino acid sequence of SEQ ID NO: 43 is the nucleotide sequence of SEQ ID NO: 48. In addition, an example of a nucleotide sequence encoding the amino acid sequence of SEQ ID NO: 47 is the nucleotide sequence of SEQ ID NO: 49. Also, the above DNAs encoding heavy-chain and light-chain constant regions preferably comprise nucleotide sequences encoding the corresponding human antibody-derived amino acid sequences.

DNA of the present invention can be obtained by, for example, the aforementioned methods or the following methods. First, total RNA is prepared from a hybridoma for an antibody of the present invention using a commercially available RNA extraction kit. Then, cDNA is synthesized with a reverse transcriptase using random primers and the like. Next, cDNA encoding an antibody is amplified by a PCR method using, as primers, oligonucleotides having sequences conserved in variable regions of known mouse antibody heavy-chain and light-chain genes. Sequences encoding constant regions can be obtained by amplifying known sequences by a PCR method. The nucleotide sequence of the DNA can be determined by a general method involving, for example, incorporation into a plasmid or phage for sequence determination.

It is thought that antitumor effects of an anti-CAPRIN-1 antibody used in the present invention upon CAPRIN-1-expressing cancer cells are exhibited through mechanisms of cytotoxicities described below.

The cytotoxicities are effector cell-mediated antibody-dependent cellular cytotoxicity (ADCC) against CAPRIN-1-expressing cells and complement-dependent cytotoxicity (CDC) against CAPRIN-1-expressing cells.

Accordingly, the activity of an anti-CAPRIN-1 antibody used in the present invention can be evaluated via ex vivo determination of ADCC activity or CDC activity to CAPRIN-1-expressing cancer cells as specifically described in the Examples mentioned below.

An anti-CAPRIN-1 antibody used in the present invention binds to a CAPRIN-1-protein on a cancer cell and exhibits antitumor effects based on the above activity. Therefore, such antibody is believed to be useful for cancer treatment or prevention. Specifically, according to the present invention, the pharmaceutical composition for treatment and/or prevention of cancer that comprises, as an active ingredient, an anti-CAPRIN-1 antibody, is provided. When an anti-CAPRIN-1 antibody is used for the purpose of administering an antibody to humans (antibody treatment), it is preferably used in the form of a human antibody or a humanized antibody in order to reduce immunogenicity.

In addition, as the binding affinity between an anti-CAPRIN-1 antibody and a CAPRIN-1 protein on a cancer cell surface becomes higher, stronger antitumor activity can be exhibited by an anti-CAPRIN-1 antibody. Therefore, if an anti-CAPRIN-1 antibody having high binding affinity to a CAPRIN-1 protein can be obtained, even stronger antitumor effects can be expected to be exhibited. Accordingly, it becomes possible to use such antibody as a pharmaceutical composition for cancer treatment and/or prevention. As described above, for high binding affinity, the affinity constant Ka ($k_{on}/k_{off}$) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

<Binding to Antigen Expression Cells>

The capacity of an antibody to bind to CAPRIN-1 can be specified via binding assay using, for example, ELISA, a Western blot method, immunofluorescence, or flowcytometry analysis as described in the Examples.

<Immunohistochemical Staining>

An antibody that recognizes CAPRIN-1 can be tested in terms of reactivity with CAPRIN-1 by an immunohistochemical method known to persons skilled in the art using a frozen tissue section fixed with paraformaldehyde or acetone or a paraffin-embedded tissue section fixed with paraformaldehyde. Such section is prepared from a tissue obtained from a patient during surgery or an animal carrying xenograft tissue that has been innoculated with a natural cell or transfected cell line that expresses CAPRIN-1.

For immunohistochemical staining, an antibody reactive to CAPRIN-1 can be stained by a variety of methods. For example, it can be visualized by reacting with a horseradish peroxidase-conjugated goat anti-mouse antibody or goat anti-rabbit antibody.

<Pharmaceutical Composition>

A target of the pharmaceutical composition for treatment and/or prevention of cancer of the present invention is not particularly limited as long as the target is a cancer (cell) expressing the CAPRIN-1 gene.

Both the terms "tumor" and "cancer" used herein refer to malignant neoplasm, and thus they are used in an exchangeable manner.

A cancer that can be a target in the present invention is a cancer expressing a gene encoding a polypeptide comprising an amino acid sequence of any one of the even-numbered SEQ ID NOS: 2 to 30 or a particle sequence consisting of 7 or more consecutive amino acids of said amino acid sequence. Preferable examples thereof include breast cancer, brain tumor, leukemia, lung cancer, lymphoma, mastocytoma, esophageal cancer, and colon cancer.

Examples of these specific cancers include, but are not limited to, breast adenocarcinoma, composite type breast adenocarcinoma, malignant mammary mixed tumor, intraductal papillary adenocarcinoma, lung adenocarcinoma, squamous cell cancer, small cell cancer, large cell cancer, glioma that is a tumor of neuroepithelial tissue, ependymoma, neuronal tumor, embryonal neuroectodermal tumor, schwannoma, neurofibroma, meningioma, chronic lymphocytic leukemia, lymphoma, gastrointestinal lymphoma, digestive lymphoma, small-cell-to-medium-cell lymphoma, cecal cancer, ascending colon cancer, descending colon cancer, transverse colon cancer, sigmoid colon cancer, and rectal cancer.

In addition, the subject animal of the present invention is a mammal. Examples thereof include mammals such as primates, pet animals, livestock animals, and sport animals. Humans, dogs, and cats are particularly preferable.

When an antibody used in the present invention is used as a pharmaceutical composition, it can be formulated by a method known to persons skilled in the art. For instance, it can be parenterally used in the form of a parenteral injection of: an aseptic solution comprising water or a pharmacologically acceptable non-water solution; or a suspension liquid. For example, in one possible case, it can be formulated with the combined use of a pharmacologically acceptable carrier or medium and specifically sterilized water, physiological saline, plant oil, an emulsifier, a suspension, a surfactant, a stabilizer, a flavoring agent, an excipient, a vehicle, a preservative, or a binder in an appropriate manner by mixing in a unit dosage form required for a generally acceptable pharmaceutical formulation. The amount of an active ingredient in a formulation is determined such that an appropriate dosage within the indicated range can be achieved.

An aseptic composition for injection purposes can be formulated in accordance with general formulation practice using a vehicle such as distilled water for injection purposes.

Examples of an aqueous solution for injection purposes include physiological saline and isotonic solutions comprising glucose and other adjuvants such as D-sorbitol, D-mannose, D-mannitol, and sodium chloride. Such solution may be used with an appropriate dissolution aid. Examples of such dissolution aid include alcohols such as ethanol and polyalcohol, propylene glycol, polyethylene glycol, and nonion surfactants such as polysorbate 80™ and HCO-60.

Examples of oily liquid include sesame oil and soybean oil. Such oily liquid may be used in combination with a dissolution aid such as benzyl benzoate or benzyl alcohol. In addition, it may be mixed with a buffering agent such as a phosphate buffer solution, a sodium acetate buffer solution, a soothing agent such as procaine hydrochloride, a stabilizer such as benzyl alcohol, phenol, or an antioxidant. In general, a formulated injection solution is introduced into an adequate ample.

The above pharmaceutical composition is orally or parenterally administered. Preferably, it is parenterally administered. Specific examples of dosage forms include injectable agents, intranasally-administered agents, transpulmonarily-administered agents, and percutaneously-administered agents. For example, injectable agents can be systemically or locally administered via intravenous injection, intramuscular injection, intraperitoneal injection, or subcutaneous injection.

In addition, the administration method can be appropriately determined depending on patient age, weight, gender, and symptoms. A single dose of a pharmaceutical composition comprising an antibody or a polynucleotide encoding an antibody can be selected within a range of, for example, 0.0001 mg to 1000 mg per kg of body weight. Alternatively, the dose can be selected within a range of, for example, 0.001 to 100000 mg per patient's body; however, it is not necessarily limited thereto. The dose and the administration method are changed depending on patient age, weight, gender, and symptoms. However, persons skilled in the art can appropriately select the dose and the method.

<Polypeptide and DNA>

According to the present invention, the following polypeptides and DNAs for antibodies (a) to (k) described above are further provided.

(i) A polypeptide comprising the amino acid sequences of SEQ ID NO: 43, SEQ ID NO: 73, SEQ ID NO: 83, SEQ ID NO: 93, SEQ ID NO: 103, SEQ ID NO: 113, and SEQ ID NO: 123, and DNA encoding the polypeptide.

(ii) A polypeptide comprising the amino acid sequences of SEQ ID NO: 47, SEQ ID NO: 53, SEQ ID NO: 58, SEQ ID NO: 63, SEQ ID NO: 68, SEQ ID NO: 77, SEQ ID NO: 87, SEQ ID NO: 97, SEQ ID NO: 107, SEQ ID NO: 117, and SEQ ID NO: 127, and DNA encoding the polypeptide.

(iii) DNA comprising the nucleotide sequences of SEQ ID NO: 48, SEQ ID NO: 78, SEQ ID NO: 88, SEQ ID NO: 98, SEQ ID NO: 108, SEQ ID NO: 118, and SEQ ID NO: 128.

(iv) DNA comprising the nucleotide sequences of SEQ ID NO: 49, SEQ ID NO: 54, SEQ ID NO: 59, SEQ ID NO: 64, SEQ ID NO: 69, SEQ ID NO: 79, SEQ ID NO: 89, SEQ ID NO: 99, SEQ ID NO: 109, SEQ ID NO: 119, and SEQ ID NO: 129.

(v) A heavy-chain CDR polypeptide comprising amino acid sequences selected from the group consisting of amino acid sequences of SEQ ID NOS: 40, 41, and 42, amino acid sequences of SEQ ID NOS: 70, 71, and 72, amino acid sequences of SEQ ID NOS: 80, 81, and 82, amino acid sequences of SEQ ID NOS: 90, 91, and 92, amino acid sequences of SEQ ID NOS: 100, 101, and 102, amino acid sequences of SEQ ID NOS: 110, 111, and 112, and amino acid sequences of SEQ ID NOS: 120, 121, and 122, and DNA encoding the polypeptide.

(vi) A light-chain CDR polypeptide comprising amino acid sequences selected from the group consisting of amino acid sequences of SEQ ID NOS: 44, 45, and 46, amino acid sequences of SEQ ID NOS: 50, 51, and 52, amino acid sequences of SEQ ID NOS: 55, 56, and 57, amino acid sequences of SEQ ID NOS: 60, 61, and 62, amino acid sequences of SEQ ID NOS: 65, 66, and 67, amino acid sequences of SEQ ID NOS: 74, 75, and 76, amino acid sequences of SEQ ID NOS: 84, 85, and 86, amino acid sequences of SEQ ID NOS: 94, 95, and 96, amino acid sequences of SEQ ID NOS: 104, 105, and 106, amino acid sequences of SEQ ID NOS: 114, 115, and 116, and amino acid sequences of SEQ ID NOS: 124, 125, and 126, and DNA encoding the polypeptide.

These polypeptides and DNAs can be produced by a gene recombinant technique as described above.

EXAMPLES

The present invention is hereafter described in greater detail with reference to the following examples, although the scope of the present invention is not limited thereto.

Example 1: Identification of New Cancer Antigen Protein by SEREX Method (1) Construction of cDNA Library Total RNA was extracted from a testis tissue of a healthy dog by an Acid guanidium-Phenol-Chloroform method and then a polyA RNA was purified according to protocols included with an Oligotex-dT30 mRNA purification Kit (Takara Shuzo Co., Ltd.).

A canine testis cDNA phage library was synthesized using the thus obtained mRNA (5 μg). The cDNA phage library was constructed using a cDNA Synthesis Kit, a ZAP-cDNA Synthesis Kit, and a ZAP-cDNA GigapackIII Gold Cloning Kit (STRATAGENE) according to protocols included with the kits. The size of the thus constructed cDNA phage library was $7.73\times10^5$ pfu/ml.

(2) Screening of cDNA Library Using Serum

Immunoscreening was performed using the above constructed canine testis cDNA phage library. Specifically, host *Escherichia coli* (XL1-Blue MRF') was infected with the phage on an NZY agarose plate (Φ90×15 mm) so as to obtain 2210 clones. *E. coli* cells were cultured at 42° C. for 3 to 4 hours to form plaques. The plate was covered with a nitrocellulose membrane (Hybond C Extra: GE Healthcare Bio-Science) impregnated with IPTG (isopropyl-β-D-thiogalactoside) at 37° C. for 4 hours, so that the protein was induced, expressed, and then transferred to the membrane. Subsequently, the membrane was collected and then immersed in TBS (10 mM Tris-HCl, 150 mM NaCl, and pH 7.5) containing 0.5% powdered skim milk, followed by overnight shaking at 4° C., thereby suppressing nonspecific reaction. The filter was reacted with a 500-fold diluted serum of a canine patient at room temperature for 2 to 3 hours.

As the above serum of a canine patient, a serum collected from a canine patient with breast cancer was used. These sera were stored at −80° C. and then subjected to pretreatment immediately before use. A method for pretreatment of serum is as follows. Specifically, host *Escherichia coli* (XL1-Blue MRF') was infected with a λ ZAP Express phage in which no foreign gene had been inserted and then cultured overnight on a NZY plate medium at 37° C. Subsequently, buffer (0.2 M $NaHCO_3$ and pH 8.3) containing 0.5 M NaCl was added to the plate, the plate was left to stand at 4° C. for 15 hours, and then a supernatant was collected as an *Escherichia coli*/phage extract. Next, the thus collected *Escherichia coli*/phage extract was applied to an NHS-column (GE Healthcare Bio-Science), so that an *Escherichia* coliphage-derived protein was immobilized. The serum of a canine patient was applied to the protein-immobilized column for reaction and then *Escherichia coli* and an antibody adsorbed to the phage were removed from the serum. The serum fraction that had passed through the column was diluted 500-fold with TBS containing 0.5% powdered skim milk. The resultant was used as an immunoscreening material.

A membrane onto which the treated serum and the above fusion protein had been blotted was washed 4 times with TBS-T (0.05% Tween20/TBS) and then caused to react with goat anti-dog IgG (Goat anti-Dog IgG-h+I HRP conjugated (BETHYL Laboratories)) diluted 5000-fold with TBS containing 0.5% powdered skim milk as a secondary antibody for 1 hour at room temperature. Detection was performed via an enzyme coloring reaction using an NBT/BCIP reaction solution (Roche). Colonies that matched sites positive for a coloring reaction were collected from the NZY agarose plate (Φ90×15 mm) and then lysed in 500 μl of an SM buffer (100 mM NaCl, 10 mM $MgClSO_4$, 50 mM Tris-HCl, 0.01% gelatin, and pH 7.5). Until colonies positive for coloring reaction were unified, secondary screening and tertiary screening were repeated so that 30,940 phage clones reacting with serum IgG were screened for by a method similar to the above. Thus, 5 positive clones were isolated.

(3) Homology Search for Isolated Antigen Gene

For nucleotide sequence analysis of the 5 positive clones isolated by the above method, a procedure for conversion from phage vectors to plasmid vectors was performed. Specifically, 200 μl of a solution was prepared to contain host *Escherichia coli* (XL1-Blue MRF') so that absorbance $OD_{600}$ was 1.0. The solution was mixed with 250 μl of a purified phage solution and then with 1 μl of an ExAssist helper phage (STRATAGENE), followed by 15 minutes of reaction at 37° C. Three (3) ml of LB medium was added and then culture was performed at 37° C. for 2.5 to 3 hours. Immediately after culture, the temperature of the solution was kept at 70° C. by water bath for 20 minutes, centrifugation was performed at 4° C. and 1000×g for 15 minutes, and then the supernatant was collected as a phagemid solution. Subsequently, 200 μl of a solution was prepared to contain phagemid host *Escherichia coli* (SOLR) so that absorbance $OD_{600}$ was 1.0. The solution was mixed with 10 μl of a purified phage solution, followed by 15 minutes of reaction at 37° C. The solution (50 μl) was seeded on LB agar medium containing ampicillin (final concentration of 50 μg/ml) and then cultured overnight at 37° C. Transformed SOLR single colony was collected and then cultured in LB medium containing ampicillin (final concentration: 50 μg/ml) at 37° C. A plasmid DNA containing the insert of interest was purified using a QIAGEN plasmid Miniprep Kit (QIAGEN).

The purified plasmid was subjected to analysis of the full-length insert sequence by a primer walking method using the T3 primer of SEQ ID NO: 31 and the T7 primer of SEQ ID NO: 32. As a result of sequence analysis, the gene sequences of SEQ ID NOS: 5, 7, 9, 11, and were obtained. A homology search program, BLAST search (www.ncbi.nlm.nih.gov/BLAST/), was performed using the nucleotide sequences of the genes and the corresponding amino acid sequences (SEQ ID NOS: 6, 8, 10, 12, and 14). As a result of this homology search with known genes, it was revealed that all of the 5 obtained genes encoded CAPRIN-1. Regarding regions to be translated to proteins, the sequence identity among the 5 genes was 100% in terms of nucleotide sequence and 99% in terms of amino acid sequence. Also, regarding regions to be translated to proteins, the sequence identity between the genes and genes encoding human factors homologous thereto (human homologs) was 94% in terms of nucleotide sequence and 98% in terms of amino acid sequence. The nucleotide sequences of the human homologues are shown in SEQ ID NOS: 1 and 3 and the amino acid sequences of the same are shown in SEQ ID NOS: 2 and 4. Also, regarding regions to be translated to proteins, the sequence identity between the thus obtained canine genes and a gene encoding a cattle homologue was 94% in terms of nucleotide sequence and 97% in terms of amino acid sequence. The nucleotide sequence of the cattle homologue is shown in SEQ ID NO: 15 and the amino acid sequence of the same is shown in SEQ ID NO: 16. In addition, regarding regions to be translated to proteins, the sequence identity between the genes encoding the human homologues and the gene encoding the cattle homologue was 94% in terms of nucleotide sequence and ranged from 93% to 97% in terms of amino acid sequence. Also, regarding regions to be translated to proteins, the sequence identity between the obtained canine genes and a gene encoding an equine homologue was 93% in terms of nucleotide sequence and 97% in terms of amino acid sequence. The nucleotide sequence of the equine homologue is shown in SEQ ID NO: 17 and the amino acid sequence of the same is shown in SEQ ID NO: 18. In addition, regarding regions to be translated to proteins, the sequence identity between the genes encoding the human homologues and the gene encoding the equine homologue was 93% in terms of nucleotide sequence and 96% in terms of amino acid sequence. Also, regarding regions to be translated to proteins, the sequence identity between the obtained canine genes and genes encoding mouse homologues ranged from 87% to 89% in terms of nucleotide sequence and ranged from 95% to 97% in terms of amino acid sequence. The nucleotide sequences of the mouse homologues are shown in SEQ ID NOS: 19, 21, 23, 25, and 27 and the amino acid sequences of the same are shown in SEQ ID NOS: 20, 22, 24, 26, and 28. In addition, regarding regions to be translated to proteins, the sequence identity between the genes encoding the human homologues and the genes encoding the mouse homologues ranged from 89% to 91% in terms of nucleotide sequence and ranged from 95% to 96% in terms of amino acid sequence. Also, regarding regions to be translated to proteins, the sequence identity between the obtained canine genes and a gene encoding a chicken homologue was 82% in terms of nucleotide sequence and 87% in terms of amino acid sequence. The nucleotide sequence of the chicken homologue is shown in SEQ ID NO: 29 and the amino acid sequence of the same is shown in SEQ ID NO: 30. In addition, regarding regions to be translated to proteins, the sequence identity between the genes encoding the human homologues and the gene encoding the chicken homologue ranged from 81% to 82% in terms of nucleotide sequence and was 86% in terms of amino acid sequence.

(4) Gene Expression Analysis in Each Tissue

Expression of the genes obtained by the above method in canine and human normal tissues and various cell lines was examined by an RT-PCR method. A reverse transcription reaction was performed as follows. Specifically, total RNA was extracted from each tissue (50 mg to 100 mg) and each cell line (5 to $10\times10^6$ cells) using a TRIZOL reagent (Invitrogen) according to protocols included therewith. cDNA was synthesized using the total RNA and Superscript First-Strand Synthesis System for RT-PCR (Invitrogen) according to protocols included therewith. PCR was performed as follows using primers specific to the obtained genes (SEQ ID NOS: 33 and 34). Specifically, PCR was performed by repeating 30 times a cycle of 94° C./30 seconds, 60° C./30 seconds, and 72° C./30 seconds using a Thermal Cycler (BIO RAD) and a reaction solution adjusted to a total amount of 25 μl through addition of each reagent and an attached buffer (0.25 μl of a sample prepared by reverse transcription reaction, the above primers (2 μM each), dNTP (0.2 mM each), and 0.65 U of ExTaq polymerase (Takara Shuzo)). In addition, the gene-specific primers mentioned above were used to amplify the region between nucleotide number 206 and nucleotide number 632 in the nucleotide sequence (canine CAPRIN-1 gene) of SEQ ID NO: 5 and the region between nucleotide number 698 and nucleotide number 1124 in the nucleotide sequence (human CAPRIN-1 gene) of SEQ ID NO: 1. For comparison control, GAPDH-specific primers (SEQ ID NOS: 35 and 36) were used at the same time. As a result, as shown in FIG. 1, strong expression was observed in testis in the case of healthy canine tissues, while expression was observed in canine breast cancer and adenocarcinoma tissues. Furthermore, expression of the human homologs homologous to the obtained genes was also confirmed. As a result, similarly to the case of canine CAPRIN-1 genes, expression could be confirmed only in the testis in the case of normal tissues. However, in the case of cancer cells, expression was detected in many types of cancer cell lines, such as cell lines of breast cancer, brain tumor, leukemia, lung cancer, and esophageal cancer. Expression was confirmed in a particularly large number of breast cancer cell lines. Based on the results, it was confirmed that CAPRIN-1 expression was not observed in normal tissues other than those of the testis while CAPRIN-1 was expressed in many cancer cells and particularly in breast cancer cell lines.

In addition, in FIG. 1, Reference No. 1 along the longitudinal axis indicates the expression pattern of each of the above-identified genes and Reference No. 2 along the same indicates the expression pattern of the GAPDH gene for comparison control.

(5) Preparation of Polyclonal Antibody Against CAPRIN-1-Derived Peptide

To obtain an antibody binding to CAPRIN-1, CAPRIN-1-derived peptide (Arg-Asn-Leu-Glu-Lys-Lys-Lys-Gly-Lys-Leu-Asp-Asp-Tyr-Gln (SEQ ID NO: 37)) was synthesized. The peptide (1 mg) as an antigen was mixed with an incomplete Freund's adjuvant (IFA) solution in an amount equivalent to the peptide. The mixture was subcutaneously administered to a rabbit 4 times every 2 weeks. Subsequently, blood was collected, so that an antiserum containing a polyclonal antibody was obtained. Furthermore, the antiserum was purified using a protein G support (GE Healthcare Bio-Sciences) and then a polyclonal antibody against the CAPRIN-1-derived peptide was obtained. In addition, an antibody obtained by purifying serum of rabbits to which no antigen had been administered with the use of a protein G support in the manner described above was designated as a control antibody.

(6) Analysis of Antigen Protein Expression on Cancer Cells

Next, it was examined whether or not the CAPRIN-1 protein was expressed on cell surfaces of 7 types of breast cancer cell lines (MDA-MB-157, T47D, MRK-nu-1, MDA-MB-231V, BT20, SK-BR-3, and MDA-MB-231T) in which CAPRIN-1 gene expression had been strongly confirmed. Each human breast cancer cell line in which gene expression had been confirmed ($10^6$ cells) as described above was centrifuged in a 1.5-ml microcentrifugal tube. The polyclonal antibody against the CAPRIN-1-derived peptide (2 μg)(5 μl) prepared in (5) above was added thereto. The resultant was further suspended in PBS containing 0.1% fetal bovine serum (95 μl) and then left to stand on ice for 1 hour. After washing with PBS, the resultant was suspended in PBS containing an FITC-labeled goat anti-rabbit IgG antibody (Santa Cruz Biotechnology, Inc.)(5 μl) and 0.1% fetal bovine serum (FBS)(95 μl) and then left to stand on ice for 1 hour. After washing with PBS, fluorescence intensity was measured using FACSCalibur (Becton, Dickinson and Company). Meanwhile, a procedure similar to the above was performed using the control antibody prepared in (5) above instead of the polyclonal antibody against a CAPRIN-1-derived peptide, so that a control was prepared. As a result, fluorescence intensity was found to be at least 30% stronger in all cells to which the anti-human CAPRIN-1 antibody had been added than that in control cells. Specifically, the following increases in fluorescence intensity were confirmed: MDA-MB-157: 184%; T47D: 221%; MRK-nu-1: 115%; MDA-MB-231V: 82%; BT20: 32%; SK-BR-3: 279%; and MDA-MB-231T: 80%. Based on the above, it was confirmed that the CAPRIN-1 protein was expressed on the cell surfaces of the above human cancer cell lines. In addition, the rate of increase in fluorescence intensity is represented by the rate of increase in mean fluorescence intensity (MFI value) in cells. It was calculated by the following equation.

Rate of increase in mean fluorescence intensity(rate of increase in fluorescence intensity) (%)=((MFI value of cells reacted with an anti-human CAPRIN-1 antibody)−(control MFI value))/(control MFI value)×100

(7) Immunohistochemical Staining (7)-1 CAPRIN-1 Expression in Normal Mouse and Canine Tissues Mice (Balb/c, female) and dogs (beagle dogs, female) were exsanguinated under ether anesthesia and ketamine/isoflurane anesthesia. After laparotomy, organs (stomach, liver, eyeball, thymus gland, muscle, bone marrow, uterus, small intestine, esophagus, heart, kidney, salivary gland, large intestine (colon), mammary gland, brain, lung, skin, adrenal gland, ovary, pancreas, spleen, and bladder) were each transferred to a 10-cm dish containing PBS. Each organ was cut open in PBS and then subjected to perfusion fixation overnight with 0.1 M phosphate buffer (pH 7.4) containing 4% paraformaldehyde (PFA). The perfusate was discarded, the tissue surface of each organ was rinsed with PBS, and then a PBS solution containing 10% sucrose was added to a 50-ml centrifugal tube. Each tissue was then placed in each tube and then shaken using a rotor at 4° C. for 2 hours. Each solution was substituted with a PBS solution containing 20% sucrose and then left to stand at 4° C. until tissues precipitated. Each solution was substituted with a PBS solution containing 30% sucrose and then left to stand at 4° C. until tissues precipitated. Each tissue was removed and a necessary portion was excised with a surgical scalpel. Next, an OCT compound (Tissue Tek) was applied and spread over each tissue surface, and then the tissues were placed on Cryomold. Cryomold was placed on dry ice for rapid freezing. Tissues were sliced into sections of 10 to 20 μm thickness using a cryostat (LEICA) and then the sliced tissue sections were air-dried on glass slides for 30 minutes using a hair dryer, so that glass slides on which sliced tissue sections had been placed were prepared. Next, each glass slide was placed in a staining bottle filled with PBS-T (saline containing 0.05% Tween20), so that a procedure involving exchange with PBS-T every 5 minutes was performed 3 times. Excess water around each specimen was removed using Kimwipes and then each section was encircled using DAKOPEN (DAKO). As blocking solutions, a MOM mouse Ig blocking reagent (VECTASTAIN) was applied onto mouse tissue and a PBS-T solution containing 10% FBS was applied onto canine tissue. The resultants were left to stand in a moist chamber at room temperature for 1 hour. Next, a solution was prepared to contain a monoclonal antibody (monoclonal antibody #6) against CAPRIN-1 having the heavy-chain variable region of SEQ ID NO: 73 and the light-chain variable region of SEQ ID NO: 77 and reacting with the cancer cell surfaces prepared in Example 4, which antibody was adjusted at a concentration of 10 μg/ml in the blocking solution. The solution was applied onto each slide glass and then left to stand within a moist chamber at 4° C. overnight. After 3 times wash, each 10 minutes, with PBS-T, a MOM biotin-labeled anti-IgG antibody (VECTASTAIN) diluted 250-fold with the blocking solution was applied onto each glass slide and then left to stand within a moist chamber at room temperature for 1 hour. After 3 times wash, each 10 minutes, with PBS-T, an avidin-biotin ABC reagent (VECTASTAIN) was applied and then left to stand within a moist chamber at room temperature for 5 minutes. After 3 times wash, each 10 minutes, with PBS-T, a DAB staining solution (DAB 10 mg+30% $H_2O_2$10 μl/0.05 M Tris-HCl (pH 7.6) 50 ml) was applied and then the glass slides were left to stand within a moist chamber at room temperature for 30 minutes. Glass slides were rinsed with distilled water and then a hematoxylin reagent (DAKO) was applied. After being left to stand at room temperature for 1 minute, the glass slides were rinsed with distilled water. The glass slides were immersed in 70%, 80%, 90%, 95%, and 100% ethanol solutions in such order for 1 minute each and then left to stand in xylene overnight. The glass slides were removed, coverslipped with Glycergel Mounting Medium (DAKO), and then observed. As a result, CAPRIN-1 expression was observed to a slight degree within cells in all salivary gland, kidney, colon, and stomach tissues, but CAPRIN-1 expression was never observed on cell surfaces. Also, absolutely no CAPRIN-1 expression was observed in tissues from other organs. In addition, similar results were obtained when the monoclonal antibody against CAPRIN-1 having the heavy-chain variable region of SEQ ID NO: 103 and the light-chain variable region of SEQ ID NO: 107 (monoclonal antibody #9) was used.

(7)-2 CAPRIN-1 Expression in Canine Breast Cancer Tissue

With the use of 108 frozen canine breast cancer tissue specimens from dogs diagnosed by pathological diagnosis as having malignant breast cancer, frozen section slides were prepared by a method similar to the above and immunohistochemical staining was performed using the monoclonal antibody #6 prepared in Example 4. As a result, CAPRIN-1 expression was confirmed in 100 out of the 108 specimens (92.5%). CAPRIN-1 was particularly strongly expressed on the surfaces of highly atypical cancer cells. In addition, similar results were obtained when the monoclonal antibody #9 produced in Example 4 was used.

(7)-3 CAPRIN-1 Expression in Human Breast Cancer Tissue

Immunohistochemical staining was performed using 188 breast cancer tissue specimens of a paraffin-embedded human breast cancer tissue array (BIOMAX). After 3 hours of treatment at 60° C., the human breast cancer tissue array was added to a staining bottle filled with xylene and then xylene replacement every 5 minutes was performed 3 times. Next, a similar procedure was performed using ethanol and PBS-T instead of xylene. The human breast cancer tissue array was added to a staining bottle filled with 10 mM citrate buffer (pH 6.0) containing 0.05% Tween20, treated for 5 minutes at 125° C., and then left to stand at room temperature for 40 minutes or more. Excess water around each specimen was removed using Kimwipes, each section was encircled using DAKOPEN, and then an appropriate amount of Peroxidase Block (DAKO) was added dropwise. The resultant was left to stand at room temperature for 5 minutes and then added to a staining bottle filled with PBS-T. PBS-T replacement every 5 minutes was performed 3 times. As a blocking solution, a PBS-T solution containing 10% FBS was applied and then left to stand within a moist chamber at room temperature for 1 hour. Next, a solution was prepared to contain the monoclonal antibody #6 reacting with the cancer cell surfaces prepared in Example 4 at a concentration of 10 μg/ml adjusted using a PBS-T solution containing 5% FBS. The solution was applied and then left to stand overnight within a moist chamber at 4° C. After 3 times wash, each 10 minutes, with PBS-T, an appropriate amount of Peroxidase Labeled Polymer Conjugated (DAKO) was added dropwise, and then the glass slides were left to stand at room temperature for 30 minutes within a moist chamber. After 3 times wash, each 10 minutes, with PBS-T, a DAB staining solution (DAKO) was applied and then left to stand at room temperature for 10 minutes. The DAB staining solution was discarded and then 10 minutes of wash was performed with PBS-T for 3 times. The glass slides were rinsed with distilled water and then immersed in 70%, 80%, 90%, 95%, and 100% ethanol solutions in such order for 1 minute each and then left to stand in xylene overnight. The glass slides were removed, coverslipped with Glycergel Mounting Medium (DAKO), and then observed. As a result, strong CAPRIN-1 expression was observed for 138 (73%) out of the total 188 breast cancer tissue specimens. In addition, similar results were obtained when the monoclonal antibody #9 prepared in Example 4 was used.

(7)-4 CAPRIN-1 Expression in Human Malignant Brain Tumor

With the use of 247 malignant brain tumor tissue specimens of paraffin-embedded human malignant brain tumor tissue arrays (BIOMAX), immunohistochemical staining was performed by a method similar to that in (7)-3 above using the monoclonal antibody #6 prepared in Example 4. As a result, strong CAPRIN-1 expression was observed in 227 (92%) out of the total 247 malignant brain tumor tissue specimens. In addition, similar results were obtained when the monoclonal antibody #9 prepared in Example 4 was used.

(7)-5 CAPRIN-1 Expression in Human Breast Cancer Metastatic Lymph Node

With the use of 150 tissue specimens of human breast cancer metastatic lymph nodes of paraffin-embedded human breast cancer metastatic lymph node tissue arrays (BIOMAX), immunohistochemical staining was performed by a method similar to that in (7)-3 above using the monoclonal antibody #6 prepared in Example 4. As a result, strong CAPRIN-1 expression was observed in 136 (90%) out of the total 150 tissue specimens of human breast cancer metastatic lymph nodes. Specifically, it was revealed that CAPRIN-1 is also strongly expressed in a cancer tissue that has metastasized from breast cancer. In addition, similar results were obtained when the monoclonal antibody #9 prepared in Example 4 was used.

Figure 2:
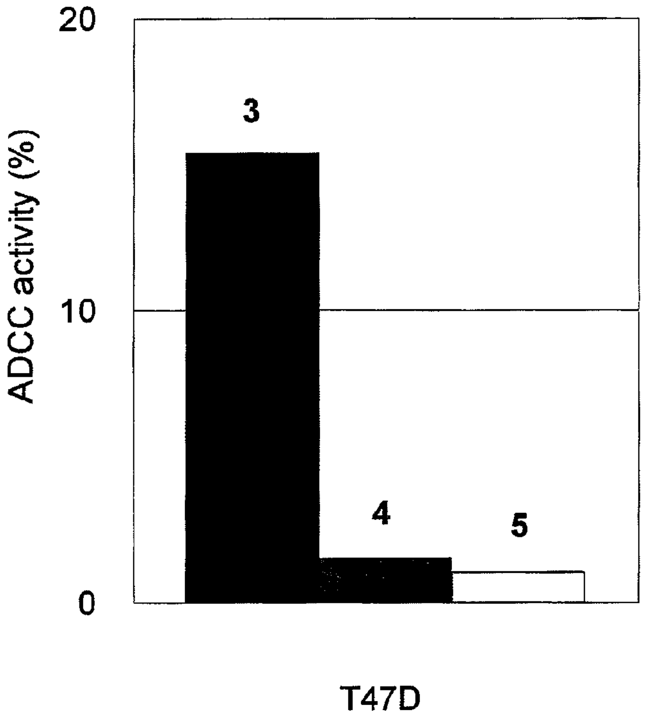
FIG. 2 shows the cytotoxic activity of an antibody to CAPRIN-1 (or anti-CAPRIN-1 antibody) against the breast cancer cell line expressing CAPRIN-1 gene (T47D). In this Fig., reference no. 3 shows the activity after addition of the anti-CAPRIN-1 antibody, reference no. 4 shows the activity after addition of control antibody, and reference no. 5 shows the activity in the absence of any antibody.
Figure 3:
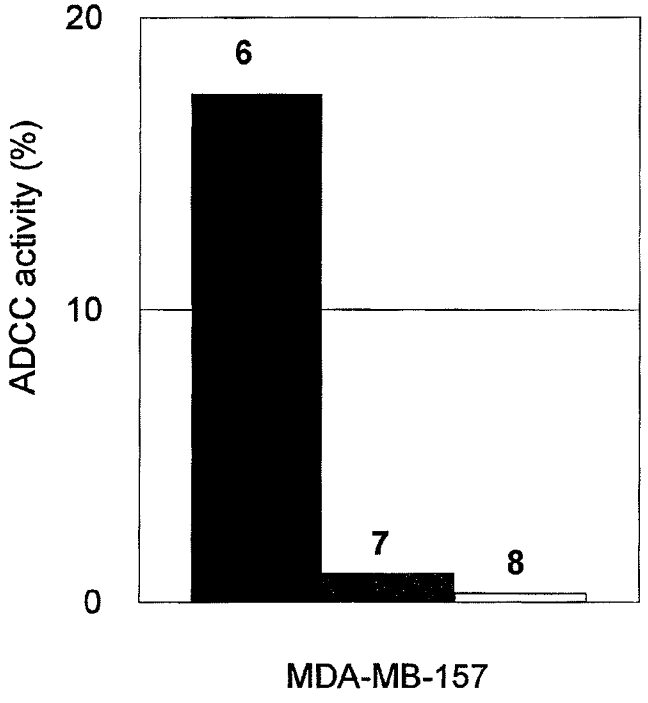
FIG. 3 shows the cytotoxic activity of an antibody to CAPRIN-1 (or anti-CAPRIN-1 antibody) against the breast cancer cell line expressing CAPRIN-1 gene (MDA-MB- 157). In this Fig., reference no. 6 show the activity after addition of the anti-CAPRIN-1 antibody, reference no. 7 shows the activity after addition of control antibody and reference no. 8 shows the activity in the absence of any antibody.

Example 2: Antitumor Effects (ADCC Activity) of Antibody Against CAPRIN-1 Upon Cancer Cells Next, it was examined whether or not an antibody against CAPRIN-1 would be able to damage CAPRIN-1-expressing tumor cells. Evaluation was carried out using the polyclonal antibody against a human CAPRIN-1-derived peptide prepared in Example 1. Two types of human breast cancer cell lines (T47D and MDA-MB-157) ($10^6$ cells each), in which CAPRIN-1 expression had been confirmed, were separately collected into a 50-ml centrifugal tube. Chromium 51 (100 μCi) was added thereto, followed by incubation at 37° C. for 2 hours. Thereafter, cells were washed 3 times with an RPMI1640 medium containing 10% fetal calf serum and added to wells ($10^3$ cells per well) in 96-well V-bottom plates. The above polyclonal antibody against a human CAPRIN-1-derived peptide was added thereto (1 μg per well). Further, lymphocytes separated from rabbit peripheral blood were added thereto ($2\times10^5$ cells per well), followed by culture under conditions of 37° C. and 5% $CO_2$ for 4 hours. After culture, the level of chromium (Cr) 51 released from damaged tumor cells in each culture supernatant was determined. Then, the ADCC activity of the polyclonal antibody against a human CAPRIN-1-derived peptide to cancer cells was calculated. As a result, ADCC activities against T47D (15.4%) and MDA-MB-157 (17.3%) were confirmed (see FIGS. 2 and 3). Meanwhile, substantially no activity was observed in a case in which a procedure similar to the above was performed using the control antibody prepared from peripheral blood of a rabbit that had not been immunized with an antigen (Example 1 (5)) or in a case in which no antibody was added (see FIGS. 2 and 3). Accordingly, it was revealed that CAPRIN-1-expressing tumor cells can be damaged by inducing ADCC activity with the use of an antibody against CAPRIN-1.

In addition, for cytotoxic activity, an antibody against CAPRIN-1 used in the present invention, mouse lymphocytes, and $10^3$ cells incorporating chromium 51 from a leukemia cell line were mixed together and cultured for 4 hours. Thereafter, the level of chromium 51 released into the medium was determined. Then, the cytotoxic activity to the leukemia cell line was calculated by the following equation*.

Cytotoxic activity (%)=[(the level of chromium 51 released from *T47D* or *MDA-MB*-157 to which an antibody against CAPRIN-1 and mouse lymphocytes were added)/(the level of chromium 51 released from target cells to which 1 N hydrochloric acid was added)]×100 *Equation:

Example 3: Preparation of New Human Cancer Antigen Proteins (1) Preparation of Recombinant Protein A recombinant protein of a human homolog gene was prepared by the following method based on the gene of SEQ ID NO: 1 obtained in Example 1. PCR was performed by repeating 30 times a cycle of 98° C./10 seconds and 68° C./2.5 minutes using a Thermal Cycler (BIO RAD) and a reaction solution adjusted to a total amount of 50 μl through addition of each reagent and an attached buffer (1 d of cDNA (which was from a variety of tissue/cell-derived cDNAs prepared in Example 1 and observed for their expression by RT-PCR), 2 types of primers (0.4 μM each; SEQ ID NOS: 38 and 39) containing SacI and XhoI restriction enzyme cleavage sequences, 0.2 mM dNTP, 1.25 U PrimeSTAR HS polymerase (Takara Shuzo)). The above 2 types of primers were used to amplify the region encoding the full-length amino acid sequence of SEQ ID NO: 2. After PCR, the thus amplified DNA was subjected to 1% agarose gel electrophoresis and then a DNA fragment of about 2.1 kbp was purified using a QIAquick Gel Extraction Kit (QIAGEN).

The purified DNA fragment was ligated to a pCR-Blunt cloning vector (Invitrogen). The vector was transformed into *Escherichia coli* and then the plasmid was collected. It was confirmed based on the sequence that the amplified gene fragment matched the target sequence. The plasmid that matched the sequence of interest was treated with SacI and XhoI restriction enzymes and then the resultant was purified using a QIAquick Gel Extraction Kit. Then, the gene sequence of interest was inserted into a pET30a expression vector (Novagen) for *Escherichia coli* treated with SacI and XhoI restriction enzymes. A His tag-fused recombinant protein can be produced using the vector. The plasmid was transformed into *Escherichia coli* BL21 (DE3) for expression and then expression induction was performed using 1 mM IPTG, so that the target protein was expressed within *Escherichia coli.*

(2) Purification of Recombinant Protein

Each above-obtained recombinant *Escherichia coli* expressing SEQ ID NO: 1 was cultured at 37° C. in LB medium containing 30 μg/ml kanamycin until the absorbance at 600 nm reached around 0.7. Then isopropyl-β-D-1-thiogalactopyranoside was added to a final concentration of 1 mM, followed by 4 hours of culture at 37° C. Subsequently, cells were collected by 10 minutes of centrifugation at 4800 rpm. The cell pellet was suspended in phosphate buffered saline and then centrifuged at 4800 rpm for 10 minutes for washing cells.

The cells were suspended in phosphate buffered saline and then subjected to ultrasonication on ice. The thus ultrasonicated *Escherichia coli* lysate was centrifuged at 6000 rpm for 20 minutes. The thus obtained supernatant was used as a soluble fraction and the thus obtained precipitate was used as an insoluble fraction.

The soluble fraction was added to a nickel chelate column (carrier: Chelating Sepharose (TradeMark) Fast Flow (GE Healthcare), column capacity: 5 mL, 50 mM hydrochloric acid buffer (pH 8.0) as equilibrated buffer)) prepared according to a conventional method. The unabsorbed fraction was washed with 50 mM hydrochloric acid buffer (pH 8.0) in an amount 10 times the capacity of the column and 20 mM phosphate buffer (pH 8.0) containing 20 mM imidazole. Immediately after washing, 6 beds were eluted with 20 mM phosphate buffer (pH 8.0) containing 100 mM imidazole. An elution fraction of 20 mM phosphate buffer (pH 8.0) containing 100 mM imidazole (for which the elution of the protein of interest had been confirmed by Coomassie staining) was added to a strong anion exchange column (carrier: Q Sepharose (TradeMark) Fast Flow (GE Healthcare), column capacity: 5 mL, and 20 mM phosphate buffer (pH 8.0) as equilibrated buffer). The unabsorbed fraction was washed with 20 mM phosphate buffer (pH 7.0) in an amount 10 times the column capacity and 20 mM phosphate buffer (pH 7.0) containing 200 mM sodium chloride. Immediately after washing, 5 beds were eluted using 20 mM phosphate buffer (pH 7.0) containing 400 mM sodium chloride. Thus, purified fractions of proteins each having the amino acid sequence shown in SEQ ID NO: 2 were obtained.

200 μl of each purified preparation obtained by the above method was dispensed into 1 ml of reaction buffer (20 mM Tris-HCl, 50 mM NaCl, 2 mM $CaCl_2$ pH 7.4) and then 2 μl of enterokinase (Novagen) was added. The preparation was left to stand at room temperature overnight for reaction, His tag was cleaved, and then purification was performed according to the attached protocols using an Enterokinase Cleavage Capture Kit (Novagen). Next, 1.2 ml of each purified preparation obtained by the above method was substituted with physiological phosphate buffer (Nissui Pharmaceutical Co., Ltd.) using ultrafiltration NANOSEP 10K OMEGA (PALL). Sterilized filtration was performed using 0.22-μm HT Tuffryn Acrodisc (PALL) and then the resultants were used for the following experiments.

Example 4: Preparation of Monoclonal Antibody Against CAPRIN-1

The antigen protein (human CAPRIN-1) (100 μg) shown in SEQ ID NO: 2 prepared in Example 3 was mixed with a MPL+TDM adjuvant (Sigma) in an amount equivalent to that of the antigen protein. The mixture was used as an antigen solution per mouse. The antigen solution was administered intraperitoneally to 6-week-old Balb/c mice (Japan SLC Inc.) and then further administered 3 times or 24 times every week for completion of immunization. Spleen was removed on day 3 after the final immunization and then ground in between two sterilized glass slides. Each resultant was washed with PBS (−) (Nissui) and then centrifuged at 1500 rpm for 10 minutes, so that a procedure to remove supernatants was repeated 3 times. Thus, spleen cells were obtained. The thus obtained spleen cells were mixed with the mouse myeloma cell SP2/0 (purchased from ATCC) at a ratio of 10:1. The PEG solution prepared by mixing 200 μl of RPMI1640 medium containing 10% FBS heated at 37° C. and 800 μl of PEG1500 (Boehringer) was added to the cells. The solution was left to stand for 5 minutes for cell fusion. Centrifugation was performed at 1700 rpm for 5 minutes to remove supernatants. Cells were suspended in 150 ml of RPMI1640 medium (HAT selective medium) containing 15% FBS, to which 2% equivalent of HAT solution (Gibco) had been added and then seeded onto fifteen 96-well plates (Nunc) at 100 μl per well. Cells were cultured for 7 days under conditions of 37° C. and 5% $CO_2$, so that hybridomas resulting from fusion of spleen cells to myeloma cells were obtained.

Hybridomas were selected using as an indicator the binding affinity of the antibody produced by the thus prepared hybridomas for the CAPRIN-1 protein. The CAPRIN-1 protein solution (1 μg/ml) prepared in Example 3 was added at 100 μl per well of 96-well plates and then left to stand at 4° C. for 18 hours. Each well was washed 3 times with PBS-T, 0.5% Bovine Serum Albumin (BSA) solution (Sigma) was added at 400 μl per well, and then the plates were left to stand at room temperature for 3 hours. The solution was removed and then each well was washed 3 times with 400 μl of PBS-T. Each culture supernatant of the hybridomas obtained above was added at 100 μl per well and then left to stand at room temperature for 2 hours. Each well was washed 3 times with PBS-T, an HRP-labeled anti-mouse IgG (H+L) antibody (Invitrogen) diluted 5000-fold with PBS was added at 100 μl per well and then left to stand at room temperature for 1 hour. Each well was washed 3 times with PBS-T, a TMB substrate solution (Thermo) was added at 100 μl per well and then left to stand for 15-30 minutes, so that a color reaction was performed. After color development, 1N sulfuric acid was added at 100 μl per well to stop the reaction. Absorbance at 450 nm and absorbance at 595 nm were measured using an absorption spectrometer. As a result, a plurality of hybridomas producing antibodies with high absorbances were selected.

The thus selected hybridomas were added at 0.5 hybridomas per well of 96-well plates and then cultured. After 1 week, hybridomas forming single colonies in wells were observed. Cells in these wells were further cultured. Hybridomas were selected using as an indicator the binding affinity (of the antibody produced by cloned hybridomas) for the CAPRIN-1 protein. The CAPRIN-1 protein solution (1 μg/ml) prepared in Example 3 was added at 100 μl per well of 96-well plates and then left to stand at 4° C. for 18 hours. Each well was washed 3 times with PBS-T, a 0.5% BSA solution was added at 400 μl per well, and then left to stand at room temperature for 3 hours. The solution was removed and then each well was washed 3 times with 400 μl of PBS-T. Each culture supernatant of the hybridomas obtained above was added at 100 μl per well and then left to stand at room temperature for 2 hours. Each well was washed 3 times with PBS-T, an HRP-labeled anti-mouse IgG (H+L) antibody (Invitrogen) diluted 5000-fold with PBS was added at 100 μl per well and then left to stand at room temperature for 1 hour. Each well was washed 3 times with PBS-T, a TMB substrate solution (Thermo) was added at 100 μl per well and then left to stand for 15-30 minutes, so that a color reaction was performed. After color development, 1N sulfuric acid was added at 100 μl per well to stop the reaction. Absorbance at 450 nm and absorbance at 595 nm were measured using an absorption spectrometer. As a result, 150 hybridoma cell lines producing monoclonal antibodies exerting reactivity with the CAPRIN-1 protein were obtained.

Next, from among these monoclonal antibodies, monoclonal antibodies exerting reactivity with the surfaces of breast cancer cells expressing CAPRIN-1 were selected. Specifically, $10^6$ cells of the MDA-MB-231V human breast cancer cell line were subjected to centrifugation with a 1.5-ml microcentrifugal tube. The supernatant (100 μl) of each hybridoma above was added and then left to stand on ice for 1 hour. After washing with PBS, an FITC-labeled goat anti-mouse IgG antibody (Invitrogen) diluted 500-fold with PBS containing 0.1% FBS was added and then left to stand on ice for 1 hour. After washing with PBS, fluorescence intensity was measured using FACSCalibur (Becton, Dickinson and Company). Meanwhile, a procedure similar to the above was performed using untreated serum of 6-week-old Balb/c mice diluted 500-fold with a hybridoma culture medium instead of the antibody so that a control was prepared. As a result, 11 monoclonal antibodies (#1 to #11) having fluorescence intensity stronger than that of the control; that is, reacting with the surfaces of breast cancer cells were selected.

Example 5: Characterization of Selected Antibodies (1) Cloning of an Anti-CAPRIN-1 Monoclonal Antibody Variable Region Gene mRNAs were extracted from hybridoma cell lines producing the 11 monoclonal antibodies selected in Example 4. The heavy-chain variable (VH) region gene and the light-chain variable (VL) region gene for every anti-CAPRIN-1 monoclonal antibody were obtained by RT-PCR using primers specific to a mouse FR1-derived sequence and a mouse FR4-derived sequence. For sequencing, the genes were separately cloned into pCR2.1 vectors (Invitrogen).

(1)-1 RT-PCR mRNA was prepared from each hybridoma cell line ($10^6$ cells) using an mRNA micro purification kit (GE Healthcare). Each obtained mRNA was subjected to reverse transcription using a SuperScriptII 1st strand synthesis kit (Invitrogen) for cDNA synthesis. The above procedures were carried out according to the protocols attached to the kits.

Each obtained cDNA was used for antibody gene amplification by PCR.

In order to obtain the VH region gene, a primer specific to a mouse heavy-chain FR1 sequence (SEQ ID NO: 130) and a primer specific to a mouse heavy-chain FR4 sequence (SEQ ID NO: 131) were used. In addition, in order to obtain the VL region gene, a primer specific to a mouse light-chain FR1 sequence (SEQ ID NO: 132) and a primer specific to a mouse light-chain FR4 sequence (SEQ ID NO: 133) were used. These primers were designed with reference to Jones, S. T. and Bending, M. M. Bio/Technology 9, 88-89 (1991). For PCR, Ex-taq (Takara Bio Inc.) was used. Each cDNA sample was mixed with a 10×EX Taq Buffer (5 μl), dNTPs Mixture (2.5 mM)(4 μl), primers (1.0 μM)(2 μl each), and Ex Taq (5 U/μl)(0.25 μl). The total volume was adjusted to 50 μl with sterilized water. PCR was carried out under conditions comprising, after treatment at 94° C. for 2 minutes, 30 cycles of a combination of denaturation at 94° C. for 1 minute, annealing at 58° C. for 30 seconds, and elongation reaction at 72° C. for 1 minute.

(1)-2 Cloning

Each PCR product obtained above was subjected to agalose gel electrophoresis, followed by excision of DNA bands of the VH region and the VL region. DNA was purified using a QIAquick Gel purification kit (QIAGEN) according to the protocols attached to the kit. Each purified DNA was cloned into a pCR2.1 vector using a TA cloning kit (Invitrogen). Each DNA-ligated vector was transformed into DH5a competent cells (TOYOBO) according to a conventional method. Each transformant (10 clones) was cultured overnight in a medium (100 μg/ml ampicillin) at 37° C. The obtained plasmid DNA was purified using a Qiaspin Miniprep kit (QIAGEN).

(1)-3 Sequencing

Gene sequence analysis of the VH region and the VL region in each plasmid obtained above was carried out using an M13 forward primer (SEQ ID NO: 134) and an M13 reverse primer (SEQ ID NO: 135) with a fluorescent sequencer (ABI; DNA sequencer 3130XL) and a BigDye terminater Ver. 3.1 cycle sequencing kit (ABI) in accordance with the protocols attached to the kit. As a result, each gene sequence (identical in 10 clones) was determined.

The obtained amino acid sequences of monoclonal antibody heavy-chain variable regions are shown in SEQ ID NO: 43, SEQ ID NO: 73, SEQ ID NO: 83, SEQ ID NO: 93, SEQ ID NO: 103, SEQ ID NO: 113, and SEQ ID NO: 123. The obtained amino acid sequences of light-chain variable regions are shown in SEQ ID NO: 47, SEQ ID NO: 53, SEQ ID NO: 58, SEQ ID NO: 63, SEQ ID NO: 68, SEQ ID NO: 77, SEQ ID NO: 87, SEQ ID NO: 97, SEQ ID NO: 107, SEQ ID NO: 117, and SEQ ID NO: 127.

Specifically, a monoclonal antibody #1 comprises the heavy-chain variable region of SEQ ID NO: 43 and the light-chain variable region of SEQ ID NO: 47. A monoclonal antibody #2 comprises the heavy-chain variable region of SEQ ID NO: 43 and the light-chain variable region of SEQ ID NO: 53. A monoclonal antibody #3 comprises the heavy-chain variable region of SEQ ID NO: 43 and the light-chain variable region of SEQ ID NO: 58. A monoclonal antibody #4 comprises the heavy-chain variable region of SEQ ID NO: 43 and the light-chain variable region of SEQ ID NO: 63. A monoclonal antibody #5 comprises the heavy-chain variable region of SEQ ID NO: 43 and the light-chain variable region of SEQ ID NO: 68. A monoclonal antibody #6 comprises the heavy-chain variable region of SEQ ID NO: 73 and the light-chain variable region of SEQ ID NO: 77. A monoclonal antibody #7 comprises the heavy-chain variable region of SEQ ID NO: 83 and the light-chain variable region of SEQ ID NO: 87. A monoclonal antibody #8 comprises the heavy-chain variable region of SEQ ID NO: 93 and the light-chain variable region of SEQ ID NO: 97. A monoclonal antibody #9 comprises the heavy-chain variable region of SEQ ID NO: 103 and the light-chain variable region of SEQ ID NO: 107. A monoclonal antibody #10 comprises the heavy-chain variable region of SEQ ID NO: 113 and the light-chain variable region of SEQ ID NO: 117. A monoclonal antibody #11 comprises the heavy-chain variable region of SEQ ID NO: 123 and the light-chain variable region of SEQ ID NO: 127.

(2) Expression of CAPRIN-1 on the Cell Surfaces of Different Cells Caused with the Use of the Obtained Monoclonal Antibodies Next, it was examined whether or not the CAPRIN-1 protein was expressed on cell surfaces of 7 types of breast cancer cell lines (MDA-MB-157, T47D, MRK-nu-1, MDA-MB-231V, BT20, SK-BR-3, and DA-MB-231T) in which CAPRIN-1 gene expression had been confirmed, 3 types of other breast cancer cell lines (MDA-MB-231C, MCF-7, and ZR75-1), 6 types of glioma cell lines (T98G, SNB19, U251, and U87G), 3 types of kidney cancer cell lines (Caki-1, Caki2, and A498), 1 type of a gastric cancer cell line (MKN45), 1 type of a colon cancer cell line (Caco2), 3 types of lung cancer cell lines (A549, QG56, and PC8), and 3 types of leukemia cell lines (Namalwa, BDCM, and RPI1788). Each cell line ($10^6$ cells) was centrifuged in a 1.5-ml microcentrifugal tube. The hybridoma supernatants (100 μl each) containing monoclonal antibodies #1 to #10 against CAPRIN-1 prepared in Example 4 reacting to cancer cell surfaces were separately added thereto and then left to stand on ice for 1 hour. After washing with PBS, each resultant was suspended in an FITC-labeled goat anti-mouse IgG antibody (Invitrogen Corporation) diluted 500-fold with PBS containing 0.1% FBS and then left to stand on ice for 1 hour. After washing with PBS, fluorescence intensity was measured using FACSCalibur (Becton, Dickinson and Company). Meanwhile, a procedure similar to the above was performed using, as a control, the control antibody prepared in (5) above instead of the hybridoma supernatants containing monoclonal antibodies #1 to #11 against CAPRIN-1, so that a control was prepared. As a result, fluorescence intensity was found to be at least 30% stronger in all cells to which the monoclonal antibodies #1 to #11 had been added than that in control cells. Specifically, the following increases in fluorescence intensity were confirmed when, for example, the monoclonal antibody #9 was used: MDA-MB-157: 211%; T47D: 145%; MRK-nu-1: 123%; MDA-MB-231V: 251%; BT20: 168%; and MDA-MB-231T: 94%. Based on the above, it was confirmed that the CAPRIN-1 protein was expressed on the cell surfaces of the above human cancer cell lines. In addition, the rate of increase in fluorescence intensity is represented by the rate of increase in mean fluorescence intensity (MFI value) in cells. It was calculated by the following equation.

Rate of increase in mean fluorescence intensity(rate of increase in fluorescence intensity) (%)=((MFI value of cells reacted with an anti-human CAPRIN-1 antibody)−(control MFI value))/(control MFI value)×100

Figure 4:
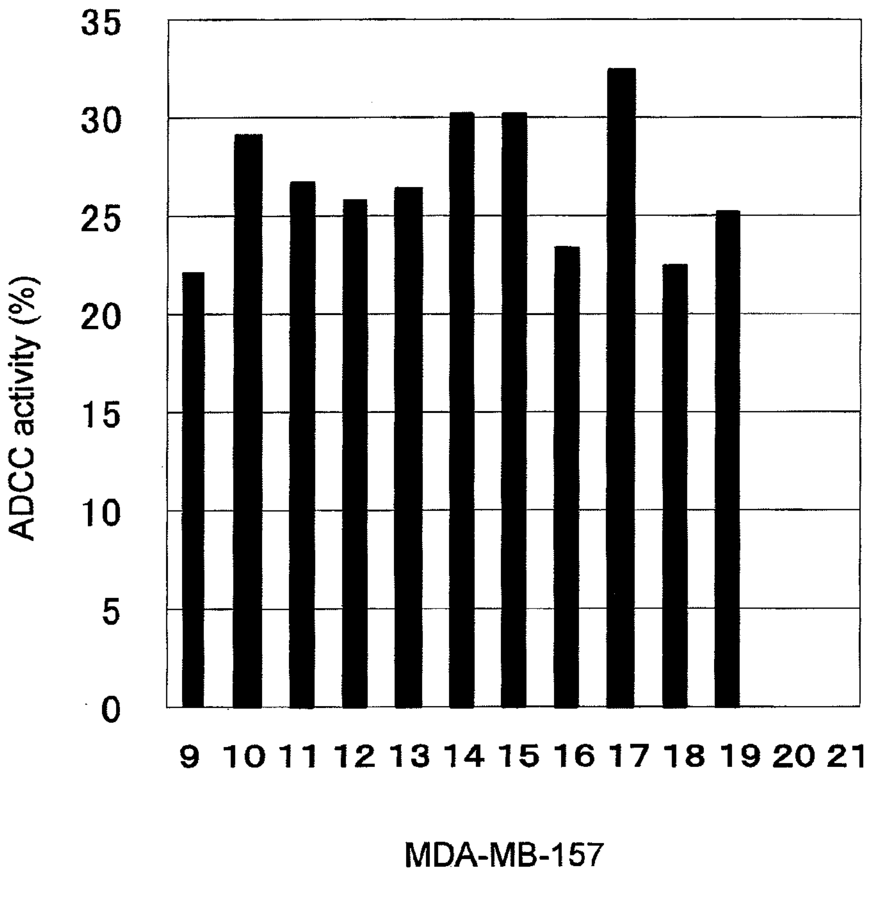
FIG. 4 shows the cytotoxicity against the breast cancer MDA-MB-157 cell line expressing CAPRIN-1, wherein the cytotoxicity is exhibited by the monoclonal antibodies to CAPRIN-1 (i.e., the monoclonal antibodies #1 to #11), which are reactive with the surface of the cancer cell. Specifically, this Fig. shows the activity levels after addition of the #1 monoclonal antibody to CAPRIN-1 (reference no. 9), the #2 monoclonal antibody to CAPRIN-1 (reference no. 10), the #3 monoclonal antibody to CAPRIN-1 (reference no. 11), the #4 monoclonal antibody to CAPRIN-1 (reference no. 12), the #5 monoclonal antibody to CAPRIN-1 (reference no. 13), the #6 monoclonal antibody to CAPRIN-1 (reference no. 14), the #7 monoclonal antibody to CAPRIN-1 (reference no. 15), the #8 monoclonal antibody to CAPRIN-1 (reference no. 16), the #9 monoclonal antibody to CAPRIN-1 (reference no. 17), the #10 monoclonal antibody to CAPRIN-1 (reference no. 18), and the #11 monoclonal antibody to CAPRIN-1 (reference no. 19), the activity level after addition of a monoclonal antibody reactive with the CAPRIN-1 protein itself but not with the surface of the cancer cell (reference no. 20), and the activity level after addition of PBS instead of each antibody (reference no. 21).

(3) Antitumor Effects (ADCC Activity) of Antibodies Against CAPRIN-1 Upon Cancer Cells The above selected monoclonal antibodies #1 to #11 against CAPRIN-1 were evaluated in terms of cytotoxic activity (ADCC activity) to cancer cells. The hybridomas producing monoclonal antibodies #1 to #11 were cultured using a hybridoma SFM medium (Invitrogen). Each obtained supernatant was purified using Hitrap ProteinA Sepharose FF (GE Healthcare), followed by substitution with PBS (−) and purification with a 0.22-μm filter (Millipore). Each resultant was used as an antibody for activity determination. The human breast cancer MDA-MB-157 cell line ($10^6$ cells) was collected into a 50-ml centrifugal tube. Chromium 51 (100 μCi) was added thereto, followed by incubation at 37° C. for 2 hours. Thereafter, cells were washed 3 times with an RPMI1640 medium containing 10% FBS. The cells were added to wells ($10^3$ cells per well) in 96-well V-bottom plates. Thus, target cells were prepared. The above purified antibodies were added thereto (1 μg per well). Further, mouse lymphocytes separated from mouse spleen ($2\times10^5$ cells) were added thereto, followed by culture under conditions of 37° C. and 5% $CO_2$ for 4 hours. After culture, the level of chromium (Cr) 51 released from damaged tumor cells in each culture supernatant was determined. Then, ADCC activity of each polyclonal antibody against a human CAPRIN-1-derived peptide to cancer cells was calculated. As a result, all monoclonal antibodies #1 to #11 exhibited ADCC activity against MDA-MB-157 (20% or more). Specifically, Specifically, for example, the following cytotoxic activity results were obtained: #1: 22.1%; #2: 29.1%; #6: 30.2%; and #9: 32.4% (see FIG. 4). Meanwhile, no cytotoxic activity was confirmed in a case in which a procedure similar to the above was performed using the monoclonal antibody reactive to a CAPRIN-1 protein itself but not to cancer cell surfaces prepared in Example 4 (see FIG. 4). The above results showed that the obtained anti-CAPRIN-1 monoclonal antibodies (#1 to #11) damaged CAPRIN-1-expressing cancer cells by exhibiting ADCC activity.

(4) Antitumor Effects (CDC Activity) of Antibodies Against CAPRIN-1 Upon Cancer Cells The above selected monoclonal antibodies #1 to #11 against CAPRIN-1 were evaluated in terms of cytotoxic activity (CDC activity) to cancer cells. Blood collected from rabbits by blood sampling was added to an Eppendorf tube and then left to stand at room temperature for 60 minutes, followed by centrifugation at 3000 rpm for 5 minutes. Thus, serum for CDC activity determination was prepared. The human breast cancer MDA-MB-231V cell line ($10^5$ cells) was collected into a 50-ml centrifugal tube. Chromium 51 (100 μCi) was added thereto, followed by incubation at 37° C. for 2 hours. Thereafter, cells were washed 3 times with an RPMI medium containing 10% FBS and then suspended in an RPMI containing 50% rabbit serum prepared above. The cells were added to wells ($10^3$ cells per well) in 96-well V-bottom plates. The antibodies #1 to #11 obtained in (3) above were separately added to wells (1 μg per well), followed by culture under conditions of 37° C. and 5% $CO_2$ for 4 hours. After culture, the level of chromium (Cr) 51 released from damaged tumor cells in each culture supernatant was determined. The CDC activity against MDA-MB-231V exhibited by the anti-CAPRIN-1 monoclonal antibody in each hybridoma supernatant was calculated. As a result, all monoclonal antibodies #1 to #11 exhibited CDC activity (30% or more). Meanwhile, no cytotoxic activity was confirmed in a case in which a procedure similar to the above was performed using the monoclonal antibody reactive to a CAPRIN-1 protein itself but not to cancer cell surfaces prepared in Example 4 (see FIG. 4). Accordingly, it has been revealed that the monoclonal antibodies against CAPRIN-1 (#1 to #11) can damage CAPRIN-1-expressing tumor cells also by exhibiting CDC activity.

Example 6: In Vivo Antitumor Effects of Anti-CAPRIN-1 Monoclonal Antibodies Upon Mice Next, in vivo antitumor effects of the obtained monoclonal antibodies #1 to #11 against CAPRIN-1 upon tumor-bearing mice were evaluated. Antibodies used in this Example were obtained by subjecting the supernatant of each hybridoma to column purification in the manner described above.

Figure 5A:
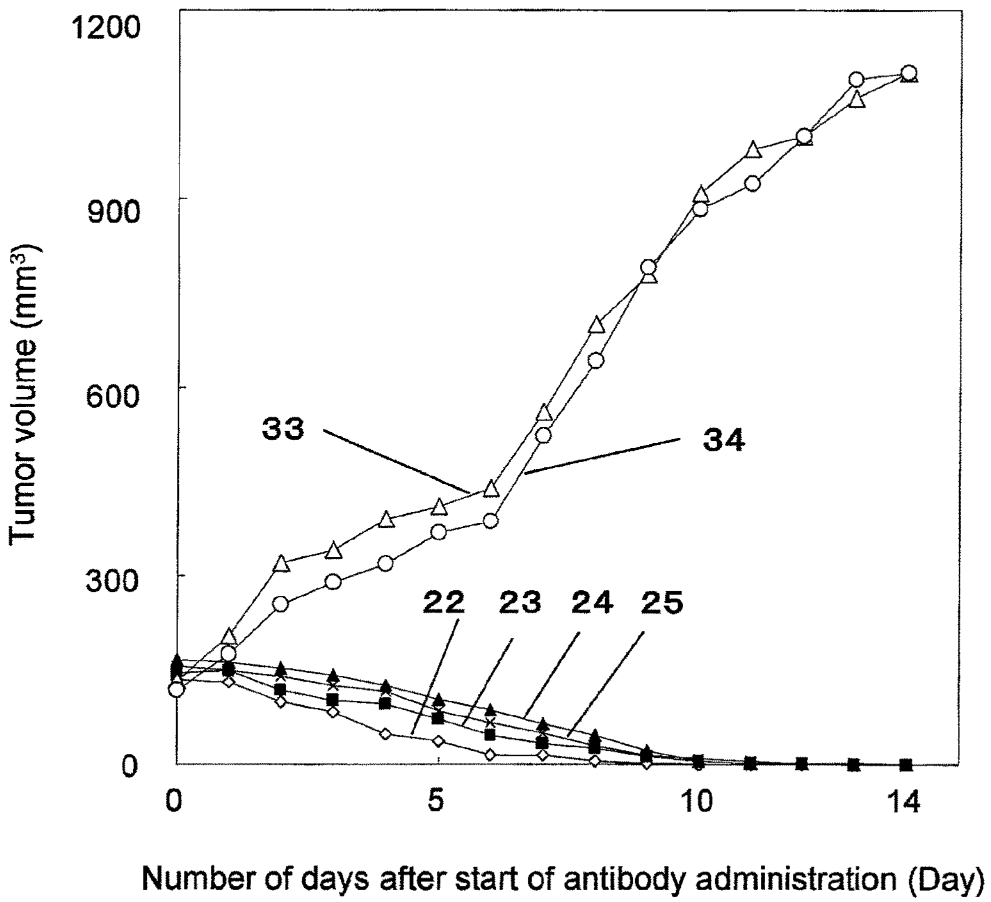
FIGS. 5*a* to 5*c* show the antitumor effect of the monoclonal antibodies to CAPRIN-1 (i.e., the monoclonal antibodies #1 to #11) reactive with the surface of a cancer cell, on Balb/c mice into which the mouse carcinoma CT26 cell line expressing CAPRIN-1 was transplanted. These Figs. show the mouse tumor sizes after administration of the #1 monoclonal antibody to CAPRIN-1 (reference no. 22), the #2 monoclonal antibody to CAPRIN-1 (reference no. 23), the #3 monoclonal antibody to CAPRIN-1 (reference no. 24), the #4 monoclonal antibody to CAPRIN-1 (reference no. 25), the #5 monoclonal antibody to CAPRIN-1 (reference no. 26), the #6 monoclonal antibody to CAPRIN-1 (reference no. 27), the #7 monoclonal antibody to CAPRIN-1 (reference no. 28), the #8 monoclonal antibody to CAPRIN-1 (reference no. 29), the #9 monoclonal antibody to CAPRIN-1 (reference no. 30), the #10 monoclonal antibody to CAPRIN-1 (reference no. 31), and the #11 monoclonal antibody to CAPRIN-1 (reference no. 32), the mouse tumor size after administration of a monoclonal antibody reactive with a CAPRIN-1 protein itself but not with the surface of the cancer cell (reference no. 33), and the mouse tumor size after administration of PBS instead of each antibody (reference no. 34).
Figure 5B:
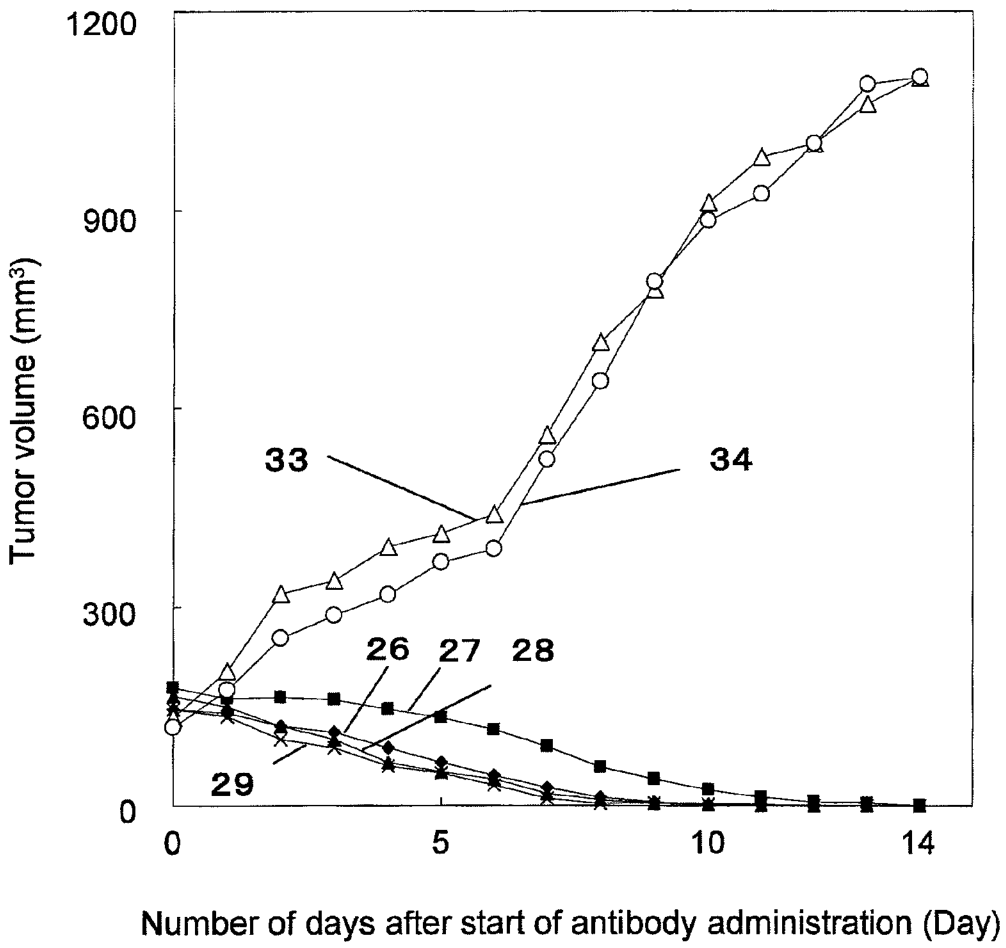
Figure 5C:
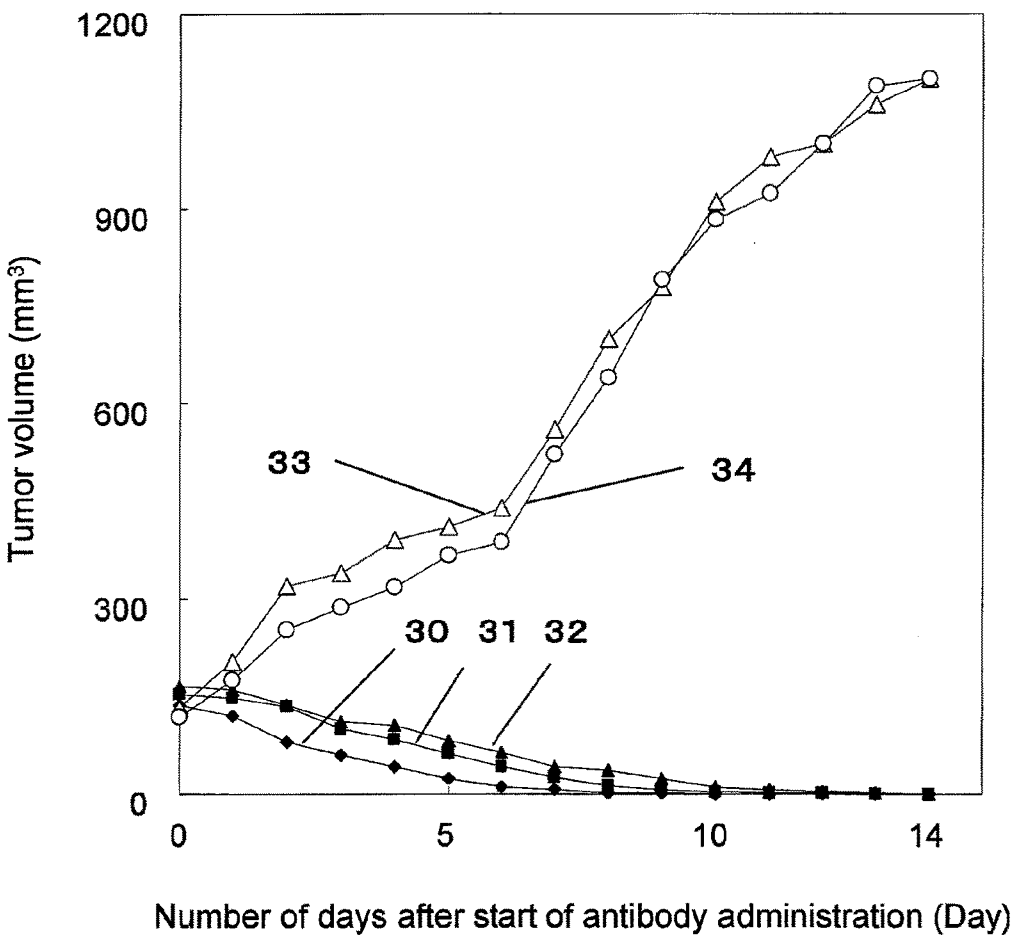

Antitumor effects of the monoclonal antibodies #1 to #11 against CAPRIN-1 were examined using tumor-bearing mice into which a mouse-derived cancer cell line expressing CAPRIN-1 had been transplanted. CT26 cells (purchased from ATCC) were subcutaneously transplanted into the dorsal portions of 70 Balb/c mice (Japan SLC, Inc.)($10^6$ cells per mouse). Each tumor was allowed to grow until the diameter thereof became approximately 7 mm. The tumor-bearing mice (60 out of 70) were subjected to intraperitoneal administration of monoclonal antibodies #1 to #11 against CAPRIN-1 and one type of the monoclonal antibody (reactive to the CAPRIN-1 protein itself but not to cancer cell surfaces) prepared in Example 4 (5 mice per antibody) at a dose of 300 μg (300 μl) per mouse. Thereafter, each antibody was intraperitoneally administered in the same dose to the relevant tumor-bearing mice 3 times in total during 2 days. The tumor size was measured every day for observation of antitumor effects. The 10 remaining tumor-bearing mice were subjected to administration of PBS (−) instead of an antibody. The group of these mice was designated as a control group. As a result of observation of antitumor effects, in the case of the test group to which monoclonal antibodies #1 to #11 against CAPRIN-1 had been administered, tumor regression occurred to such an extent that the tumor volume at the start of antibody administration (100%) decreased to 50% by Day 4, approximately 10% by Day 6, and several percents by Day 8. Substantially complete tumor regression took place from Days 11 to 14 (see FIG. 5). On the other hand, in the control group, the tumor volume increased to approximately 260%, 350%, 550%, and 800% of the original volume by Days 4, 6, 8, and 11, respectively (see FIG. 5). In addition, in the group of mice to which the monoclonal antibody (reactive to the CAPRIN-1 protein itself but not to cancer cell surfaces) had been administered, antitumor effects could not be exhibited and tumor growth occurred as in the control group. The results indicate that the obtained monoclonal antibodies #1 to #11 against CAPRIN-1 exhibit strong in vivo antitumor effects upon cancer cells expressing CAPRIN-1. In addition, the tumor size was obtained by calculating the tumor volume by the following formula: long diameter×short diameter×short diameter×0.5.

Figure 6A:
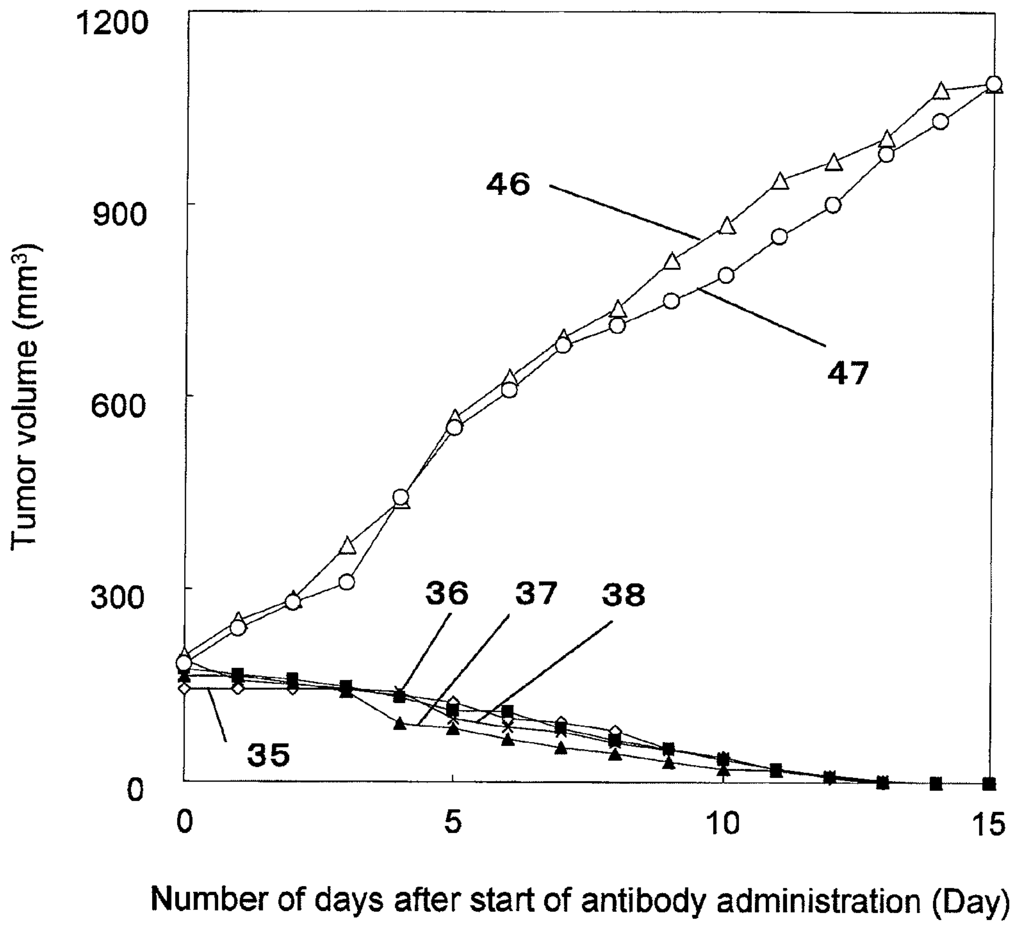
FIGS. 6*a* to 6*c* show the antitumor effect of monoclonal antibodies to CAPRIN-1 (i.e., the monoclonal antibodies #1 to #11) reactive with the surface of a cancer cell, on Balb/c mice into which the mouse carcinoma N1E cell line expressing CAPRIN-1 was transplanted. These Figs. show the mouse tumor sizes after administration of the #1 monoclonal antibody to CAPRIN-1 (reference no. 35), the #2 monoclonal antibody to CAPRIN-1 (reference no. 36), the #3 monoclonal antibody to CAPRIN-1 (reference no. 37), the #4 monoclonal antibody to CAPRIN-1 (reference no. 38), the #5 monoclonal antibody to CAPRIN-1 (reference no. 39), the #6 monoclonal antibody to CAPRIN-1 (reference no. 40), the #7 monoclonal antibody against CAPRIN-1 (reference no. 41), the #8 monoclonal antibody against CAPRIN-1 (reference no. 42), the #9 monoclonal antibody against CAPRIN-1 (reference no. 43), the #10 monoclonal antibody to CAPRIN-1 (reference no. 44), and the #11 monoclonal antibody against CAPRIN-1 (reference no. 45), the mouse tumor size after administration of a monoclonal antibody reactive with a CAPRIN-1 protein itself but not with the surface of the cancer cell (reference no. 46), and the mouse tumor size after administration of PBS instead of each antibody (reference no. 47).
Figure 6B:
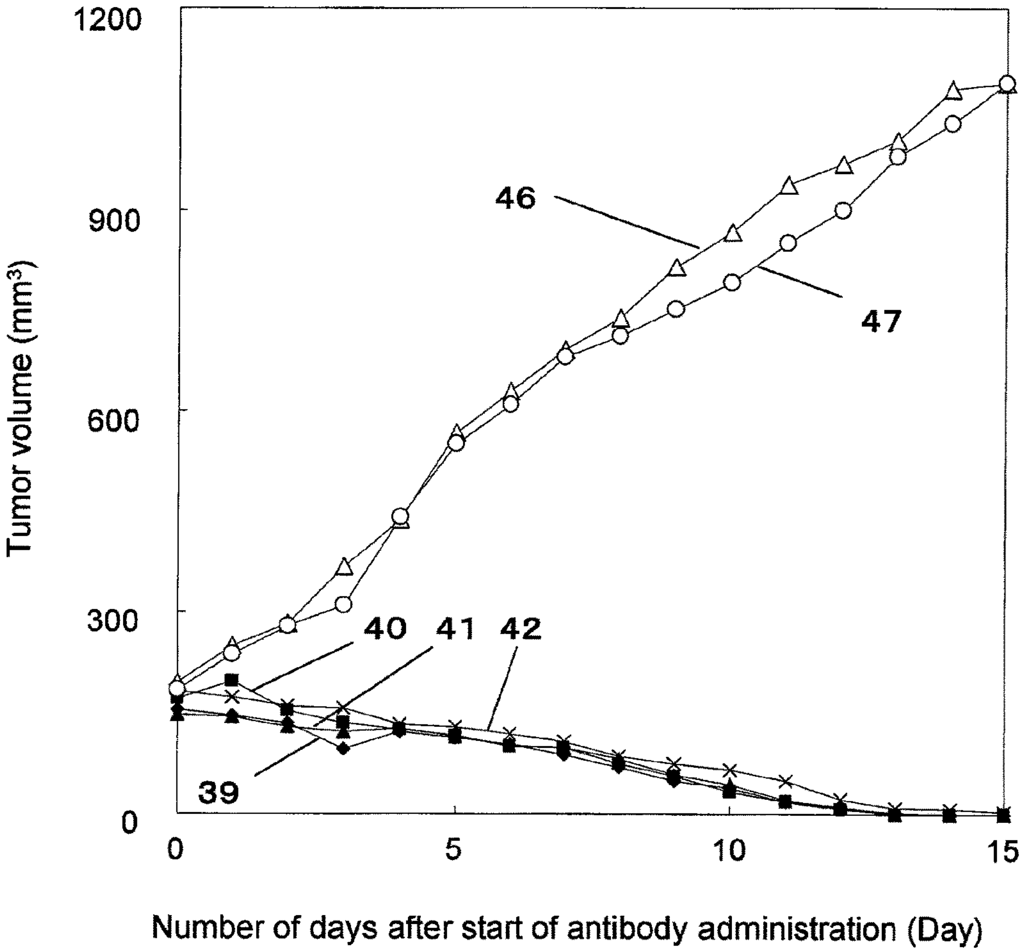
Figure 6C:
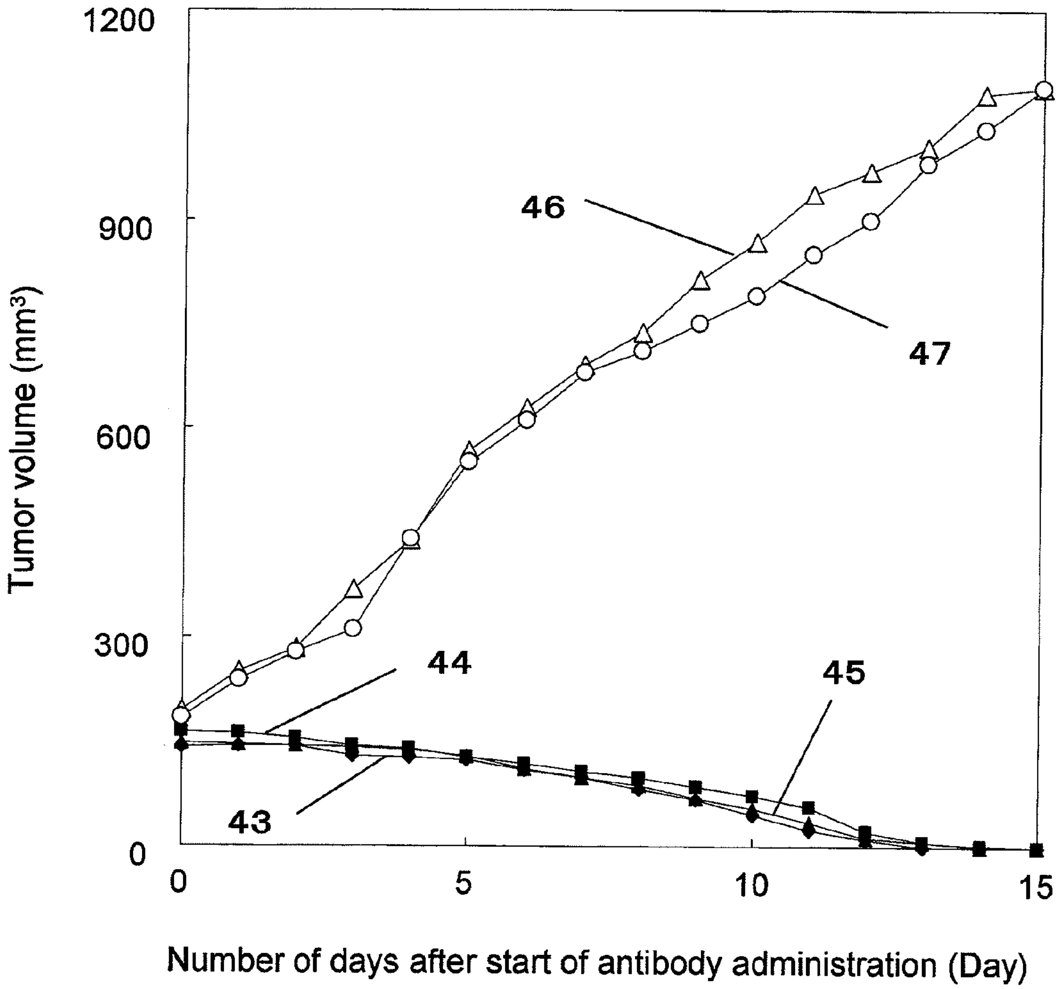

Further, monoclonal antibodies #1 to #11 against CAPRIN-1 were administered in the manner described above to tumor-bearing mice (Balb/c) into which mouse N1E cancer cells (purchased from ATCC) had been transplanted. This resulted in complete tumor regression by Day 15 after antibody administration. On the other hand, in the control group, the tumor volume increased to as high as approximately 950% of the original volume (see FIG. 6).

Example 7: Identification of a Peptide in CAPRIN-1 Protein, to which an Antibody Against CAPRIN-1 Reacting to Cancer Cell Surface Binds With the use of monoclonal antibodies #1 to #11 against CAPRIN-1, reacting with the surfaces of cancer cells (obtained above), partial sequences in the CAPRIN-1 protein to be recognized by these monoclonal antibodies were identified.

First, DTT (Fluka) was added to 100 μl of a solution prepared by dissolving a recombinant CAPRIN-1 protein at a concentration of 1 μg/μl with PBS to a final concentration of 10 mM, followed by 5 minutes of reaction at 95° C., so that reduction of disulfide bonds within the CAPRIN-1 protein was performed. Next, iodoacetamide (Wako Pure Chemical Industries, Ltd.) with a final concentration of 20 mM was added and then an alkylation reaction was performed for thiol groups at 37° C. for 30 minutes under shading conditions. Fifty (50) μg each of monoclonal antibodies #1 to #11 against CAPRIN-1 was added to 40 μg of the thus obtained reduced-alkylated CAPRIN-1 protein, the volume of the mixture was adjusted to 1 mL of 20 mM phosphate buffer (pH 7.0), and then the mixture was left to react overnight at 4° C. while stirring and mixing each mixture.

Next, trypsin (Promega) was added to a final concentration of 0.2 μg. After 1 hour, 2 hours, 4 hours, and then 12 hours of reaction at 37° C., the resultants were mixed with protein A-glass beads (GE), which were subjected in advance to blocking with PBS containing 1% BSA (Sigma) and then to washing with PBS, in 1 mM calcium carbonate and NP-40 buffer (20 mM phosphate buffer (pH 7.4), 5 mM EDTA, 150 mM NaCl, and 1% NP-40), followed by 30 minutes of reaction.

The reaction mixtures were each washed with 25 mM ammonium carbonate buffer (pH 8.0) and then antigen-antibody complexes were eluted using 100 μl of 0.1% formic acid. LC-MS analysis was conducted for eluates using Q-TOF Premier (Waters-MicroMass) according to the protocols attached to the instrument.

As a result, the polypeptide of SEQ ID NO: 136 was identified as a partial sequence of CAPRIN-1, which was recognized by all of the monoclonal antibodies #1 to #11 against CAPRIN-1. Furthermore, the peptide of SEQ ID NO: 137 was identified as a partial sequence in the polypeptide of SEQ ID NO: 136 above, which peptide was recognized by the monoclonal antibodies #2 to #5, #6 to #8, and #10. It was further revealed that the monoclonal antibodies #2 to #5 recognized the peptide of SEQ ID NO: 138 that was a partial sequence peptide of the peptide of SEQ IS NO: 137.

INDUSTRIAL APPLICABILITY

The antibodies of the present invention are useful for treatment and/or prevention of cancers.

This description includes all or part of the contents as disclosed in the description and/or drawings of Japanese Patent Application No. 2009-087285, to which the present application claims the priority. In addition, all publications, patents, and patent applications cited herein are incorporated herein by reference in their entirety.

FREE TEXT OF SEQUENCE LISTING

Primers: SEQ ID NOS: 31 to 39 and 130 to 135

The invention claimed is:

1. An antibody that binds a polypeptide consisting of the amino acid sequence shown in SEQ ID NO: 37 or SEQ ID NO: 136, wherein the antibody binds a human CAPRIN-1 protein expressing on the surface of cancer cells.

2. The antibody according to claim 1, which is a human antibody, a humanized antibody, a chimeric antibody, a single-chain antibody, or a bispecific antibody.

3. A pharmaceutical composition for treatment of CAPRIN-1 expressing cancer, which comprises, as an active ingredient, the antibody according to claim 1 or a fragment thereof that binds a CAPRIN-1 protein expressing on the surface of cancer cells.

4. The antibody according to claim 1, comprising:

a) a heavy chain variable region comprising a CDR1 of SEQ ID NO: 40, a CDR2 of SEQ ID NO: 41, and a CDR3 of SEQ ID NO: 42; and b) a light chain variable region comprising a CDR1 of SEQ ID NO: 44, a CDR2 of SEQ ID NO: 45 and a CDR3 of SEQ ID NO: 46.

5. The antibody according to claim 1, comprising:

a) a heavy chain variable region comprising a CDR1 of SEQ ID NO: 40, a CDR2 of SEQ ID NO: 41, and a CDR3 of SEQ ID NO: 42; and b) a light chain variable region comprising a CDR 1 of SEQ ID NO: 50, a CDR2 of SEQ ID NO: 51, and a CDR3 of SEQ ID NO: 52.

6. The antibody according to claim 1, comprising:

a) a heavy chain variable region comprising a CDR1 of SEQ ID NO: 40, a CDR2 of SEQ ID NO: 41, and a CDR3 of SEQ ID NO: 42; and b) a light chain variable region comprising a CDR1 of SEQ ID NO: 55, a CDR2 of SEQ ID NO: 56, and a CDR3 of SEQ ID NO: 57.

7. The antibody according to claim 1, comprising, a) a heavy chain variable region comprising a CDR1 of SEQ ID NO: 40, a CDR2 of SEQ ID NO: 41, and a CDR3 of SEQ ID NO: 42; and b) a light chain variable region comprising a CDR1 of SEQ ID NO: 60, a CDR2 of SEQ ID NO: 61, and a CDR3 of SEQ ID NO: 62.

8. The antibody according to claim 1, comprising, a) a heavy chain variable region comprising a CDR1 of SEQ ID NO: 40, a CDR2 of SEQ ID NO: 41, and a CDR3 of SEQ ID NO: 42; and b) a light chain variable region comprising a CDR1 of SEQ ID NO: 65, a CDR2 of SEQ ID NO: 66, and a CDR3 of SEQ ID NO: 67.

9. The antibody according to claim 1, comprising:

a) a heavy chain variable region comprising a CDR1 of SEQ ID NO: 70, a CDR2 of SEQ ID NO: 71, and a CDR3 of SEQ ID NO: 72, and b) a light chain variable region comprising a CDR1 of SEQ ID NO: 74, a CDR2 of SEQ ID NO: 75, and a CDR3 of SEQ ID NO: 76.

10. The antibody according to claim 1, comprising:

a) a heavy chain variable region comprising a CDR1 of SEQ ID NO: 80, a CDR2 of SEQ ID NO: 81, and a CDR3 of SEQ ID NO: 82; and b) a light chain variable region comprising a CDR1 of SEQ ID NO: 84, a CDR2 of SEQ ID NO: 85, and a CDR3 of SEQ ID NO: 86.

11. The antibody according to claim 1, comprising:

a) a heavy chain variable region comprising a CDR1 of SEQ ID NO: 90, a CDR2 of SEQ ID NO: 91, and a CDR3 of SEQ ID NO: 92; and b) a light chain variable region comprising a CDR1 of SEQ ID NO: 94, CDR2 of SEQ ID NO: 95, and a CDR3 of SEQ ID NO: 96.

12. The antibody according to claim 1, comprising:

a) a heavy chain variable region comprising a CDR1 of SEQ ID NO: 100, a CDR2 of SEQ ID NO: 101, and a CDR3 of SEQ ID NO: 102; and b) a light chain variable region comprising a CDR1 of SEQ ID NO: 104, a CDR2 of SEQ ID NO: 105, and a CDR3 of SEQ ID NO: 106.

13. The antibody according to claim 1, comprising:

a) a heavy chain variable region comprising a CDR1 of SEQ ID NO: 110, a CDR2 of SEQ ID NO: 111, and a CDR3 of SEQ ID NO: 112, and b) a light chain variable region comprising a CDR1 of SEQ ID NO: 114, a CDR2 of SEQ ID NO: 115, and a CDR3 of SEQ ID NO: 116.

14. The antibody according to claim 1, comprising:

a) a heavy chain variable region comprising a CDR1 of SEQ ID NO: 120, a CDR2 of SEQ ID NO: 121, and a CDR3 of SEQ ID NO: 122; and b) a light chain variable region comprising a CDR1 of SEQ ID NO: 124, a CDR2 of SEQ ID NO: 125, and a CDR3 of SEQ ID NO: 126.

* * * * *

```
                         SEQUENCE LISTING


<160> NUMBER OF SEQ ID NOS: 138

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1

cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac       375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat       471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa       615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa       663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga       711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat       759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag       807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa       855
Tyr Glu His Ala Ser Ile His Leu Trp Asp Leu Leu Glu Gly Lys Glu
            210                 215                 220
```

-continued

```
aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460

cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca     1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt     1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag     1815
Pro Pro Val Asn Glu Pro Glu Thr Leu Lys Gln Gln Asn Gln Tyr Gln
```

```
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                675                 680                 685

cca cga ggt cgt gga ggg ccc cca aga ccc aac aga ggg atg ccg caa      2295
Pro Arg Gly Arg Gly Gly Pro Pro Arg Pro Asn Arg Gly Met Pro Gln
            690                 695                 700

atg aac act cag caa gtg aat taa tctgattcac aggattatgt ttaatcgcca    2349
Met Asn Thr Gln Gln Val Asn
        705

aaaacacact ggccagtgta ccataatatg ttaccagaag agttattatc tatttgttct   2409

ccctttcagg aaacttattg taaagggact gttttcatcc cataaagaca ggactacaat   2469

tgtcagcttt ctattacctg gatatggaag gaaactattt ttactctgca tgttctgtcc   2529

taagcgtcat cttgagcctt gcacatgata ctcagattcc tcacccttgc ttaggagtaa   2589

aacaatatac tttacagggt gataataatc tccatagtta tttgaagtgg cttgaaaaag   2649

gcaagattga cttttatgac attggataaa atctacaaat cagccctcga gttattcaat   2709

gataactgac aaactaaatt atttccctag aaaggaagat gaaaggagtg gagtgtggtt   2769

tggcagaaca actgcatttc acagcttttc cagttaaatt ggagcactga acgttcagat   2829

gcataccaaa ttatgcatgg gtcctaatca cacatataag gctggctacc agctttgaca   2889

cagcactgtt catctggcca aacaactgtg gttaaaaaca catgtaaaat gctttttaac   2949

agctgatact gtataagaca aagccaagat gcaaaattag gctttgattg gcactttttg   3009

aaaaatatgc aacaaatatg ggatgtaatc cggatggccg cttctgtact taatgtgaaa   3069

tatttagata cctttttgaa cacttaacag tttctttgag acaatgactt ttgtaaggat   3129

tggtactatc tatcattcct tatgacatgt acattgtctg tcactaatcc ttggattttg   3189

ctgtattgtc acctaaattg gtacaggtac tgatgaaaat ctctagtgga taatcataac   3249

actctcggtc acatgttttt ccttcagctt gaaagctttt ttttaaaagg aaaagatacc   3309

aaatgcctgc tgctaccacc cttttcaatt gctatctttt gaaaggcacc agtatgtgtt   3369
```

-continued ttagattgat ttccctgttt cagggaaatc acggacagta gtttcagttc tgatggtata 3429 agcaaaacaa ataaaacgtt tataaaagtt gtatcttgaa acactggtgt tcaacagcta 3489 gcagcttatg tgattcaccc catgccacgt tagtgtcaca aattttatgg tttatctcca 3549 gcaacatttc tctagtactt gcacttatta tcttttgtct aatttaacct taactgaatt 3609 ctccgtttct cctggaggca tttatattca gtgataattc cttcccttag atgcataggg 3669 agagtctcta aatttgatgg aaatggacac ttgagtagtg acttagcctt atgtactctg 3729 ttggaatttg tgctagcagt ttgagcacta gttctgtgtg cctaggaagt taatgctgct 3789 tattgtctca ttctgacttc atggagaatt aatcccacct ttaagcaaag gctactaagt 3849 taatggtatt ttctgtgcag aaattaaatt ttattttcag catttagccc aggaattctt 3909 ccagtaggtg ctcagctatt taaaaacaaa actattctca aacattcatc attagacaac 3969 tggagttttt gctggttttg taacctacca aaatggatag gctgttgaac attccacatt 4029 caaaagtttt gtagggtggt gggaaatggg ggatcttcaa tgtttatttt aaaataaaat 4089 aaaataagtt cttgactttt ctcatgtgtg gttgtggtac atcatattgg aagggttaac 4149 ctgttacttt ggcaaatgag tatttttttg ctagcacctc cccttgcgtg ctttaaatga 4209 catctgcctg ggatgtacca caaccatatg ttacctgtat cttaggggaa tggataaaat 4269 atttgtggtt tactgggtaa tccctagatg atgtatgctt gcagtcctat ataaaactaa 4329 atttgctatc tgtgtagaaa ataatttcat gacatttaca atcaggactg aagtaagttc 4389 ttcacacagt gacctctgaa tcagtttcag agaagggatg ggggagaaaa tgccttctag 4449 gttttgaact tctatgcatt agtgcagatg ttgtgaatgt gtaaaggtgt tcatagtttg 4509 actgtttcta tgtatgtttt ttcaaagaat tgttcctttt tttgaactat aatttttctt 4569 tttttggtta ttttaccatc acagtttaaa tgtatatctt ttatgtctct actcagacca 4629 tatttttaaa ggggtgcctc attatggggc agagaacttt tcaataagtc tcattaagat 4689 ctgaatcttg gttctaagca ttctgtataa tatgtgattg cttgtcctag ctgcagaagg 4749 ccttttgttt ggtcaaatgc atatttttagc agagtttcaa ggaaatgatt gtcacacatg 4809 tcactgtagc ctcttggtgt agcaagctca catacaaaat acttttgtat atgcataata 4869 taaatcatct catgtggata tgaaacttct tttttaaaac ttaaaaaggt agaatgttat 4929 tgattacctt gattagggca gttttatttc cagatcctaa taattcctaa aaaatatgga 4989 aaagtttttt ttcaatcatt gtaccttgat attaaaacaa atatccttta agtatttcta 5049 atcagttagc ttctacagtt cttttgtctc cttttatatg cagctcttac gtgggagact 5109 tttccactta aaggagacat agaatgtgtg cttattctca gaaggttcat taactgaggt 5169 gatgagttaa caactagttg agcagtcagc ttcctaagtg ttttaggaca tttgttcatt 5229 atattttccg tcatataact agaggaagtg gaatgcagat aagtgccgaa ttcaaaccct 5289 tcattttatg tttaagctcc tgaatctgca ttccacttgg gttgttttta agcattctaa 5349 attttagttg attataagtt agatttcaca gaatcagtat tgcccttgat cttgtccttt 5409 ttatggagtt aacggggagg aagacccctc aggaaaacga aagtaaattg ttaaggctca 5469 tcttcatacc tttttccatt ttgaatccta caaaaatact gcaaaagact agtgaatgtt 5529 taaaattaca ctagattaaa taatatgaaa gtc 5562

<210> SEQ ID NO 2
<211> LENGTH: 709
<212> TYPE: PRT

<213> ORGANISM: Homo sapiens

<400> SEQUENCE: 2

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400
```

-continued

```
Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705


<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 3

cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
```

-continued 1 5 10 tcc gga ccg cca ccg ccg tcg ggt tcc tcc ggg agt gag gcg gcc gcg 279
Ser Gly Pro Pro Pro Pro Ser Gly Ser Ser Gly Ser Glu Ala Ala Ala
15 20 25 30 gga gcc ggg gcc gcc gcg ccg gct tct cag cac ccc gca acc ggc acc 327
Gly Ala Gly Ala Ala Ala Pro Ala Ser Gln His Pro Ala Thr Gly Thr
35 40 45 ggc gct gtc cag acc gag gcc atg aag cag att ctc ggg gtg atc gac 375
Gly Ala Val Gln Thr Glu Ala Met Lys Gln Ile Leu Gly Val Ile Asp
50 55 60 aag aaa ctt cgg aac ctg gag aag aaa aag ggt aag ctt gat gat tac 423
Lys Lys Leu Arg Asn Leu Glu Lys Lys Lys Gly Lys Leu Asp Asp Tyr
65 70 75 cag gaa cga atg aac aaa ggg gaa agg ctt aat caa gat cag ctg gat 471
Gln Glu Arg Met Asn Lys Gly Glu Arg Leu Asn Gln Asp Gln Leu Asp
80 85 90 gcc gtt tct aag tac cag gaa gtc aca aat aat ttg gag ttt gca aaa 519
Ala Val Ser Lys Tyr Gln Glu Val Thr Asn Asn Leu Glu Phe Ala Lys
95 100 105 110 gaa tta cag agg agt ttc atg gca cta agt caa gat att cag aaa aca 567
Glu Leu Gln Arg Ser Phe Met Ala Leu Ser Gln Asp Ile Gln Lys Thr
115 120 125 ata aag aag aca gca cgt cgg gag cag ctt atg aga gaa gaa gct gaa 615
Ile Lys Lys Thr Ala Arg Arg Glu Gln Leu Met Arg Glu Glu Ala Glu
130 135 140 cag aaa cgt tta aaa act gta ctt gag cta cag tat gtt ttg gac aaa 663
Gln Lys Arg Leu Lys Thr Val Leu Glu Leu Gln Tyr Val Leu Asp Lys
145 150 155 ttg gga gat gat gaa gtg cgg act gac ctg aaa caa ggt ttg aat gga 711
Leu Gly Asp Asp Glu Val Arg Thr Asp Leu Lys Gln Gly Leu Asn Gly
160 165 170 gtg cca ata ttg tcc gaa gag gag ttg tca ttg ttg gat gaa ttc tat 759
Val Pro Ile Leu Ser Glu Glu Glu Leu Ser Leu Leu Asp Glu Phe Tyr
175 180 185 190 aag cta gta gac cct gaa cgg gac atg agc ttg agg ttg aat gaa cag 807
Lys Leu Val Asp Pro Glu Arg Asp Met Ser Leu Arg Leu Asn Glu Gln
195 200 205 tat gaa cat gcc tcc att cac ctg tgg gac ctg ctg gaa ggg aag gaa 855
Tyr Glu His Ala Ser Ile His Leu Trp Asp Leu Leu Glu Gly Lys Glu
210 215 220 aaa cct gta tgt gga acc acc tat aaa gtt cta aag gaa att gtt gag 903
Lys Pro Val Cys Gly Thr Thr Tyr Lys Val Leu Lys Glu Ile Val Glu
225 230 235 cgt gtt ttt cag tca aac tac ttt gac agc acc cac aac cac cag aat 951
Arg Val Phe Gln Ser Asn Tyr Phe Asp Ser Thr His Asn His Gln Asn
240 245 250 ggg ctg tgt gag gaa gaa gag gca gcc tca gca cct gca gtt gaa gac 999
Gly Leu Cys Glu Glu Glu Glu Ala Ala Ser Ala Pro Ala Val Glu Asp
255 260 265 270 cag gta cct gaa gct gaa cct gag cca gca gaa gag tac act gag caa 1047
Gln Val Pro Glu Ala Glu Pro Glu Pro Ala Glu Glu Tyr Thr Glu Gln
275 280 285 agt gaa gtt gaa tca aca gag tat gta aat aga cag ttc atg gca gaa 1095
Ser Glu Val Glu Ser Thr Glu Tyr Val Asn Arg Gln Phe Met Ala Glu
290 295 300 aca cag ttc acc agt ggt gaa aag gag cag gta gat gag tgg aca gtt 1143
Thr Gln Phe Thr Ser Gly Glu Lys Glu Gln Val Asp Glu Trp Thr Val
305 310 315 gaa acg gtt gag gtg gta aat tca ctc cag cag caa cct cag gct gca 1191

-continued

```
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca      1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg      1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat      1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa      1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460

cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635
```

-continued

```
tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat     2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685

cca cga ggt aat att ttg tgg tgg tga tcctagctcc taagtggagc           2294
Pro Arg Gly Asn Ile Leu Trp Trp
            690

ttctgttctg gccttggaag agctgttaat agtctgcatg ttaggaatac atttatcctt   2354

tccagacttg ttgctaggga ttaaatgaaa tgctctgttt ctaaaactta atcttggacc   2414

caaattttaa tttttgaatg atttaatttt ccctgttact atataaactg tcttgaaaac   2474

tagaacatat tctcttctca gaaaaagtgt ttttccaact gaaaattatt tttcaggtcc   2534

taaaacctgc taaatgtttt taggaagtac ttactgaaac atttttgtaa gacatttttg   2594

gaatgagatt gaacatttat ataaatttat tattcctctt tcattttttt gaaacatgcc   2654

tattatattt tagggccaga caccctttaa tggccggata agccatagtt aacatttaga   2714

gaaccattta gaagtgatag aactaatgga atttgcaatg ccttttggac ctctattagt   2774

gatataaata tcaagttatt tctgactttt aaacaaaact cccaaattcc taacttattg   2834

agctatactt aaaaaaaatt acaggtttag agagtttttt gtttttcttt tactgttgga   2894

aaactacttc ccattttggc aggaagttaa cctatttaac aattagagct agcatttcat   2954

gtagtctgaa attctaaatg gttctctgat ttgagggagg ttaaacatca aacaggtttc   3014

ctctattggc cataacatgt ataaaatgtg tgttaaggag gaattacaac gtactttgat   3074

ttgaatacta gtagaaactg gccaggaaaa aggtacattt ttctaaaaat taatggatca   3134

cttgggaatt actgacttga ctagaagtat caaaggatgt ttgcatgtga atgtgggtta   3194

tgttctttcc caccttgtag catattcgat gaaagttgag ttaactgata gctaaaaatc   3254

tgttttaaca gcatgtaaaa agttatttta tctgttaaaa gtcattatac agttttgaat   3314

gttatgtagt ttctttttaa cagtttaggt aataaggtct gttttcattc tggtgctttt   3374

attaattttg atagtatgat gttacttact actgaaatgt aagctagagt gtacactaga   3434

atgtaagctc catgagagca ggtaccttgt ctgtcttctc tgctgtatct attcccaacg   3494

cttgatgatg gtgcctggca catagtaggc actcaataaa tatttgttga atgaatgaa    3553
```

```
<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
```

-continued

```
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495
```

```
Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690


<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5

gtcacaaata acttggagtt tgcaaaagaa ttacagagga gtttc atg gca tta agt      57
                                                  Met Ala Leu Ser
                                                      1

caa gat att cag aaa aca ata aag aag act gca cgt cgg gag cag ctt      105
Gln Asp Ile Gln Lys Thr Ile Lys Lys Thr Ala Arg Arg Glu Gln Leu
5                   10                  15                  20

atg aga gag gaa gcg gaa caa aaa cgt tta aaa act gta ctt gag ctc      153
Met Arg Glu Glu Ala Glu Gln Lys Arg Leu Lys Thr Val Leu Glu Leu
                25                  30                  35

cag tat gtt ttg gac aaa ttg gga gat gat gaa gtg aga act gac ctg      201
Gln Tyr Val Leu Asp Lys Leu Gly Asp Asp Glu Val Arg Thr Asp Leu
            40                  45                  50

aag caa ggt ttg aat gga gtg cca ata ttg tct gaa gaa gaa ttg tcg      249
Lys Gln Gly Leu Asn Gly Val Pro Ile Leu Ser Glu Glu Glu Leu Ser
        55                  60                  65

ttg ttg gat gaa ttc tac aaa tta gca gac cct gaa cgg gac atg agc      297
Leu Leu Asp Glu Phe Tyr Lys Leu Ala Asp Pro Glu Arg Asp Met Ser
    70                  75                  80

ttg agg ttg aat gag cag tat gaa cat gct tcc att cac ctg tgg gac      345
Leu Arg Leu Asn Glu Gln Tyr Glu His Ala Ser Ile His Leu Trp Asp
85                  90                  95                  100
```

-continued

```
ttg ctg gaa gga aag gaa aag tct gta tgt gga aca acc tat aaa gca      393
Leu Leu Glu Gly Lys Glu Lys Ser Val Cys Gly Thr Thr Tyr Lys Ala
                105                 110                 115

cta aag gaa att gtt gag cgt gtt ttc cag tca aat tac ttt gac agc      441
Leu Lys Glu Ile Val Glu Arg Val Phe Gln Ser Asn Tyr Phe Asp Ser
            120                 125                 130

act cac aac cac cag aat ggg cta tgt gag gaa gaa gag gca gcc tca      489
Thr His Asn His Gln Asn Gly Leu Cys Glu Glu Glu Glu Ala Ala Ser
        135                 140                 145

gca cct aca gtt gaa gac cag gta gct gaa gct gag cct gag cca gca      537
Ala Pro Thr Val Glu Asp Gln Val Ala Glu Ala Glu Pro Glu Pro Ala
    150                 155                 160

gaa gaa tac act gaa caa agt gaa gtt gaa tca aca gag tat gta aat      585
Glu Glu Tyr Thr Glu Gln Ser Glu Val Glu Ser Thr Glu Tyr Val Asn
165                 170                 175                 180

aga caa ttt atg gca gaa aca cag ttc agc agt ggt gaa aag gag cag      633
Arg Gln Phe Met Ala Glu Thr Gln Phe Ser Ser Gly Glu Lys Glu Gln
                185                 190                 195

gta gat gag tgg acg gtc gaa aca gtg gag gtg gtg aat tca ctc cag      681
Val Asp Glu Trp Thr Val Glu Thr Val Glu Val Val Asn Ser Leu Gln
            200                 205                 210

cag caa cct cag gct gcg tct cct tca gta cca gag ccc cac tct ttg      729
Gln Gln Pro Gln Ala Ala Ser Pro Ser Val Pro Glu Pro His Ser Leu
        215                 220                 225

act ccg gtg gct cag gca gat ccc ctt gtg aga aga cag cga gtc cag      777
Thr Pro Val Ala Gln Ala Asp Pro Leu Val Arg Arg Gln Arg Val Gln
    230                 235                 240

gac ctt atg gcg cag atg cag ggg ccc tat aat ttc ata cag gat tca      825
Asp Leu Met Ala Gln Met Gln Gly Pro Tyr Asn Phe Ile Gln Asp Ser
245                 250                 255                 260

atg ctg gat ttt gaa aac cag aca ctc gat cct gcc att gta tct gca      873
Met Leu Asp Phe Glu Asn Gln Thr Leu Asp Pro Ala Ile Val Ser Ala
                265                 270                 275

cag cct atg aat ccg aca caa aac atg gac atg ccc cag ctg gtt tgc      921
Gln Pro Met Asn Pro Thr Gln Asn Met Asp Met Pro Gln Leu Val Cys
            280                 285                 290

cct cca gtt cat tct gaa tct aga ctt gct caa cct aat caa gtt cct      969
Pro Pro Val His Ser Glu Ser Arg Leu Ala Gln Pro Asn Gln Val Pro
        295                 300                 305

gta caa cca gaa gct aca cag gtt cct ttg gtt tca tcc aca agt gag     1017
Val Gln Pro Glu Ala Thr Gln Val Pro Leu Val Ser Ser Thr Ser Glu
    310                 315                 320

ggg tat aca gca tct caa ccc ttg tac cag cct tct cat gct aca gag     1065
Gly Tyr Thr Ala Ser Gln Pro Leu Tyr Gln Pro Ser His Ala Thr Glu
325                 330                 335                 340

caa cga cca caa aag gaa cca att gac cag att cag gca aca atc tct     1113
Gln Arg Pro Gln Lys Glu Pro Ile Asp Gln Ile Gln Ala Thr Ile Ser
                345                 350                 355

tta aat aca gac cag act aca gcg tca tca tcc ctt ccg gct gct tct     1161
Leu Asn Thr Asp Gln Thr Thr Ala Ser Ser Ser Leu Pro Ala Ala Ser
            360                 365                 370

cag cct cag gta ttc cag gct ggg aca agc aaa cca tta cat agc agt     1209
Gln Pro Gln Val Phe Gln Ala Gly Thr Ser Lys Pro Leu His Ser Ser
        375                 380                 385

gga atc aat gta aat gca gct cca ttc caa tcc atg caa acg gtg ttc     1257
Gly Ile Asn Val Asn Ala Ala Pro Phe Gln Ser Met Gln Thr Val Phe
    390                 395                 400

aat atg aat gcc cca gtt cct cct gtt aat gaa cca gaa act ttg aaa     1305
Asn Met Asn Ala Pro Val Pro Pro Val Asn Glu Pro Glu Thr Leu Lys
405                 410                 415                 420
```

-continued

```
caa caa aat cag tac cag gcc agt tat aac cag agc ttt tct agt cag     1353
Gln Gln Asn Gln Tyr Gln Ala Ser Tyr Asn Gln Ser Phe Ser Ser Gln
                425                 430                 435

cct cac caa gta gaa caa aca gag gga tgc cgc aaa tga acactcagca      1402
Pro His Gln Val Glu Gln Thr Glu Gly Cys Arg Lys
            440                 445

agtgaattaa tctgattcac aggattatgt ttaaacgcca aaaacacact ggccagtgta   1462

ccataatatg ttaccagaag agttattatc tatttgttct ccctttcagg aaacttattg   1522

taaagggact gttttcatcc cataaagaca ggactacaat tgtcagcttt atattacctg   1582

gaaaaaaaaa aaaaaaaaaa aaa                                           1605


<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285
```

```
Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
        435                 440                 445


<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)

<400> SEQUENCE: 7

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
```

-continued

```
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
```

-continued

```
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttgttct ccctttcagg aaacttattg taaagggact   2274

gttttcatcc cataaagaca ggactacaat tgtcagcttt atattacctg gatatggaag   2334

gaaactattt ttattctgca tgttcttcct aagcgtcatc ttgagccttg cacatgatac   2394

tcagattcct cacccttgct taggagtaaa acataataca ctttacaggg tgatatctcc   2454

atagttattt gaagtggctt ggaaaaagca agattaactt ctgacattgg ataaaaatca   2514

acaaatcagc cctagagtta ttcaaatggt aattgacaaa aactaaaata tttcccttcg   2574

agaaggagtg gaatgtggtt tggcagaaca actgcatttc acagcttttc cggttaaatt   2634
```

-continued

```
ggagcactaa acgtttagat gcataccaaa ttatgcatgg gcccttaata taaaaggctg   2694

gctaccagct ttgacacagc actattcatc ctctggccaa acaactgtgg ttaaacaaca   2754

catgtaaatt gctttttaac agctgatact ataataagac aaagccaaaa tgcaaaaatt   2814

gggctttgat tggcactttt tgaaaaatat gcaacaaata tgggatgtaa tctggatggc   2874

cgcttctgta cttaatgtga agtatttaga tacctttttg aacacttaac agtttcttct   2934

gacaatgact tttgtaagga ttggtactat ctatcattcc ttataatgta cattgtctgt   2994

cactaatcct cagatcttgc tgtattgtca cctaaattgg tacaggtact gatgaaaata   3054

tctaatggat aatcataaca ctcttggtca catgtttttc ctgcagcctg aaggttttta   3114

aaagaaaaag atatcaaatg cctgctgcta ccaccctttt aaattgctat cttttgaaaa   3174

gcaccagtat gtgttttaga ttgatttccc tattttaggg aaatgacaga cagtagtttc   3234

agttctgatg gtataagcaa aacaaataaa acatgtttat aaaagttgta tcttgaaaca   3294

ctggtgttca acagctagca gcttatgtgg ttcaccccat gcattgttag tgtttcagat   3354

tttatggtta tctccagcag ctgtttctgt agtacttgca tttatctttt gtctaaccct   3414

aatattctca cggaggcatt tatattcaaa gtggtgatcc cttcacttag acgcataggg   3474

agagtcacaa gtttgatgaa gaggacagtg tagtaattta tatgctgttg gaatttgtgc   3534

tagcagtttg agcactagtt ctgtgtgcct atgaacttaa tgctgcttgt catattccac   3594

tttgacttca tggagaatta atcccatcta ctcagcaaag gctatactaa tactaagtta   3654

atggtatttt ctgtgcagaa attgaatttt gttttattag catttagcta aggaattttt   3714

ccagtaggtg ctcagctact aaagaaaaac aaaaacaaga cacaaaacta ttctcaaaca   3774

ttcattgtta gacaactgga gtttttgctg gttttgtaac ctactaaaat ggataggctg   3834

ttgaacattc cacattcaaa agttttttgt agggtggtgg ggaagggggg gtgtcttcaa   3894

tgtttatttt aaaataaaat aagttcttga cttttctcat gtgtggttgt ggtacatcat   3954

attggaaggg ttatctgttt acttttgcaa atgagtattt ctcttgctag cacctcccgt   4014

tgtgcgcttt aaatgacatc tgcctgggat gtaccacaac catatgttag ctgtatttta   4074

tggggaatag ataaaatatt cgtggtttat tgggtaatcc ctagatgtgt atgcttacaa   4134

tcctatatat aaaactaaat                                               4154
```

<210> SEQ ID NO 8
<211> LENGTH: 717
<212> TYPE: PRT
<213> ORGANISM: Canis familiaris

<400> SEQUENCE: 8

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
```

-continued

```
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525
```

```
Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125
```

-continued

```
caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
```

-continued

```
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685

agt gga cca cgg gga gcc cca cga ggt aat att ttg tgg tgg tga          2109
Ser Gly Pro Arg Gly Ala Pro Arg Gly Asn Ile Leu Trp Trp
    690                 695                 700

tcctagctcc taagtggagc ttctgttctg gccttggaag agctgttcca tagtctgcat   2169

gtaggttaca tgttaggaat acatttatca ttaccagact tgttgctagg gattaaatga   2229

aatgctctgt ttctaaaact tctcttgaac ccaaatttaa tttttgaat gactttccct    2289

gttactatat aaattgtctt gaaaactaga acatttctcc tcctcagaaa aagtgttttt   2349

ccaactgcaa attatttttc aggtcctaaa acctgctaaa tgtttttagg aagtacttac   2409

tgaaacattt ttgtaagaca tttttggaat gagattgaac atttatataa atttattatt   2469

attcctcttt catttttgaa catgcatatt atattttagg gtcagaaatc ctttaatggc   2529
```

```
caaataagcc atagttacat ttagagaacc atttagaagt gatagaacta actgaaattt   2589
caatgccttt ggatcattaa tagcgatata aatttcaaat tgtttctgac ttttaaataa   2649
aacatccaaa atcctaacta acttcctgaa ctatatttaa aaattacagg tttaaggagt   2709
ttctggtttt ttttctctta ccataggaaa actgtttcct gtttggccag gaagtcaacc   2769
tgtgtaataa ttagaagtag catttcatat gatctgaagt tctaaatggt tctctgattt   2829
aagggaagtt aaattgaata ggtttcctct agttattggc cataacatgt ataaaatgta   2889
tattaaggag gaatacaaag tactttgatt tcaatgctag tagaaactgg ccagcaaaaa   2949
ggtgcatttt atttttaaat taatggatca cttgggaatt actgacttga agtatcaaag   3009
gatatttgca tgtgaatgtg ggttatgttc tttctcacct tgtagcatat tctatgaaag   3069
ttgagttgac tggtagctaa aaatctgttt taacagcatg taaaaagtta ttttatctgt   3129
tacaagtcat tatacaattt tgaatgttat gtagtttctt tttaacagtt taggtaacaa   3189
ggtctgtttt tcattctggt gcttttatta attttgatag tatgatgtta cttactactg   3249
aaatgtaagc tagagtgtac actagaatgt aagctccatg agagcaggta ccttgtctgt   3309
cttcactgct gtatctattt ccaacgcctg atgacagtgc ctgacacata gtaggcactc   3369
aataaatact tgttgaatga atgaatgaat gagtactggt ggaatactcc attagctcta   3429
ctcttctttt agctagagaa catgagcaaa tttgcgcatg acaacttcca ggacaggtga   3489
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact atttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttggaaaa agcaagatta   4029
acttctgaca ttggataaaa atcaacaaat cagccctaga gttattcaaa tggtaattga   4089
caaaaactaa aatatttccc ttcgagaagg agtggaatgt ggtttggcag aacaactgca   4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagatacctt   4449
tttgaacact taacagtttc ttctgacaat gacttttgta aggattggta ctatctatca   4509
ttccttataa tgtacattgt ctgtcactaa tcctcagatc ttgctgtatt gtcacctaaa   4569
ttggtacagg tactgatgaa aatatctaat ggataatcat aacactcttg gtcacatgtt   4629
tttcctgcag cctgaaggtt tttaaaagaa aaagatatca aatgcctgct gctaccaccc   4689
ttttaaattg ctatcttttg aaaagcacca gtatgtgttt tagattgatt tccctatttt   4749
agggaaatga cagacagtag tttcagttct gatggtataa gcaaaacaaa taaaacatgt   4809
ttataaaagt tgtatcttga aacactggtg ttcaacagct agcagcttat gtggttcacc   4869
```

-continued

```
ccatgcattg ttagtgtttc agattttatg gttatctcca gcagctgttt ctgtagtact   4929

tgcatttatc                                                          4939


<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
```

-continued

```
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
    690                 695                 700


<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)

<400> SEQUENCE: 11

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15
```

```
ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
```

-continued

```
                325                 330                 335

cag caa cct cag gct gcg tct cct tca gta cca gag ccc cac tct ttg      1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag      1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca      1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca      1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc      1248
Gln Pro Met Asn Pro Thr Gln Asn Met Asp Met Pro Gln Leu Val Cys
            405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
            485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
            565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
```

-continued

```
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gga tgc cgc aaa tga acactcagca agtgaattaa tctgattcac    2070
Tyr Gln Arg Gly Cys Arg Lys
        675

aggattatgt ttaaacgcca aaaacacact ggccagtgta ccataatatg ttaccagaag   2130

agttattatc tatttgttct ccctttcagg aaacttattg taaagggact gttttcatcc   2190

cataaagaca ggactacaat tgtcagcttt atattacctg gatatggaag gaaactattt   2250

ttattctgca tgttcttcct aagcgtcatc ttgagccttg cacatgatac tcagattcct   2310

caccccttgct taggagtaaa acataataca ctttacaggg tgatatctcc atagttattt  2370

gaagtggctt ggaaaaagca agattaactt ctgacattgg ataaaaatca acaaatcagc   2430

cctagagtta ttcaaatggt aattgacaaa aactaaaata tttcccttcg agaaggagtg   2490

gaatgtggtt tggcagaaca actgcatttc acagcttttc cggttaaatt ggagcactaa   2550

acgtttagat gcataccaaa ttatgcatgg gcccttaata taaaaggctg gctaccagct   2610

ttgacacagc actattcatc ctctggccaa acaactgtgg ttaaacaaca catgtaaatt   2670

gctttttaac agctgatact ataataagac aaagccaaaa tgcaaaaatt gggctttgat   2730

tggcactttt tgaaaaatat gcaacaaata tgggatgtaa tctggatggc cgcttctgta   2790

cttaatgtga agtatttaga taccttttttg aacacttaac agtttcttct gacaatgact  2850

tttgtaagga ttggtactat ctatcattcc ttataatgta cattgtctgt cactaatcct   2910

cagatcttgc tgtattgtca cctaaattgg tacaggtact gatgaaaata tctaatggat   2970

aatcataaca ctcttggtca catgtttttc ctgcagcctg aaggttttta aaagaaaaag   3030

atatcaaatg cctgctgcta ccacccttttt aaattgctat cttttgaaaa gcaccagtat  3090

gtgttttaga ttgatttccc tattttaggg aaatgacaga cagtagtttc agttctgatg   3150

gtataagcaa aacaaataaa acatgtttat aaaagttgta tcttgaaaca ctggtgttca   3210

acagctagca gcttatgtgg ttcaccccat gcattgttag tgtttcagat tttatggtta   3270

tctccagcag ctgtttctgt agtacttgca tttatc                             3306


<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95
```

```
Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
```

-continued

```
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675


<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140
```

-continued atg aga gag gaa gcg gaa caa aaa cgt tta aaa act gta ctt gag ctc 480
Met Arg Glu Glu Ala Glu Gln Lys Arg Leu Lys Thr Val Leu Glu Leu
145 150 155 160 cag tat gtt ttg gac aaa ttg gga gat gat gaa gtg aga act gac ctg 528
Gln Tyr Val Leu Asp Lys Leu Gly Asp Asp Glu Val Arg Thr Asp Leu
165 170 175 aag caa ggt ttg aat gga gtg cca ata ttg tct gaa gaa gaa ttg tcg 576
Lys Gln Gly Leu Asn Gly Val Pro Ile Leu Ser Glu Glu Glu Leu Ser
180 185 190 ttg ttg gat gaa ttc tac aaa tta gca gac cct gaa cgg gac atg agc 624
Leu Leu Asp Glu Phe Tyr Lys Leu Ala Asp Pro Glu Arg Asp Met Ser
195 200 205 ttg agg ttg aat gag cag tat gaa cat gct tcc att cac ctg tgg gac 672
Leu Arg Leu Asn Glu Gln Tyr Glu His Ala Ser Ile His Leu Trp Asp
210 215 220 ttg ctg gaa gga aag gaa aag tct gta tgt gga aca acc tat aaa gca 720
Leu Leu Glu Gly Lys Glu Lys Ser Val Cys Gly Thr Thr Tyr Lys Ala
225 230 235 240 cta aag gaa att gtt gag cgt gtt ttc cag tca aat tac ttt gac agc 768
Leu Lys Glu Ile Val Glu Arg Val Phe Gln Ser Asn Tyr Phe Asp Ser
245 250 255 act cac aac cac cag aat ggg cta tgt gag gaa gaa gag gca gcc tca 816
Thr His Asn His Gln Asn Gly Leu Cys Glu Glu Glu Glu Ala Ala Ser
260 265 270 gca cct aca gtt gaa gac cag gta gct gaa gct gag cct gag cca gca 864
Ala Pro Thr Val Glu Asp Gln Val Ala Glu Ala Glu Pro Glu Pro Ala
275 280 285 gaa gaa tac act gaa caa agt gaa gtt gaa tca aca gag tat gta aat 912
Glu Glu Tyr Thr Glu Gln Ser Glu Val Glu Ser Thr Glu Tyr Val Asn
290 295 300 aga caa ttt atg gca gaa aca cag ttc agc agt ggt gaa aag gag cag 960
Arg Gln Phe Met Ala Glu Thr Gln Phe Ser Ser Gly Glu Lys Glu Gln
305 310 315 320 gta gat gag tgg acg gtc gaa aca gtg gag gtg gtg aat tca ctc cag 1008
Val Asp Glu Trp Thr Val Glu Thr Val Glu Val Val Asn Ser Leu Gln
325 330 335 cag caa cct cag gct gcg tct cct tca gta cca gag ccc cac tct ttg 1056
Gln Gln Pro Gln Ala Ala Ser Pro Ser Val Pro Glu Pro His Ser Leu
340 345 350 act ccg gtg gct cag gca gat ccc ctt gtg aga aga cag cga gtc cag 1104
Thr Pro Val Ala Gln Ala Asp Pro Leu Val Arg Arg Gln Arg Val Gln
355 360 365 gac ctt atg gcg cag atg cag ggg ccc tat aat ttc ata cag gat tca 1152
Asp Leu Met Ala Gln Met Gln Gly Pro Tyr Asn Phe Ile Gln Asp Ser
370 375 380 atg ctg gat ttt gaa aac cag aca ctc gat cct gcc att gta tct gca 1200
Met Leu Asp Phe Glu Asn Gln Thr Leu Asp Pro Ala Ile Val Ser Ala
385 390 395 400 cag cct atg aat ccg aca caa aac atg gac atg ccc cag ctg gtt tgc 1248
Gln Pro Met Asn Pro Thr Gln Asn Met Asp Met Pro Gln Leu Val Cys
405 410 415 cct cca gtt cat tct gaa tct aga ctt gct caa cct aat caa gtt cct 1296
Pro Pro Val His Ser Glu Ser Arg Leu Ala Gln Pro Asn Gln Val Pro
420 425 430 gta caa cca gaa gct aca cag gtt cct ttg gtt tca tcc aca agt gag 1344
Val Gln Pro Glu Ala Thr Gln Val Pro Leu Val Ser Ser Thr Ser Glu
435 440 445 ggg tat aca gca tct caa ccc ttg tac cag cct tct cat gct aca gag 1392
Gly Tyr Thr Ala Ser Gln Pro Leu Tyr Gln Pro Ser His Ala Thr Glu
450 455 460

-continued

```
caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttggact gttttcatcc cataaagaca ggactacaat   2274

tgtcagc                                                             2281
```

<210> SEQ ID NO 14
<211> LENGTH: 717
<212> TYPE: PRT
<213> ORGANISM: Canis familiaris

<400> SEQUENCE: 14

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
```

```
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)

<400> SEQUENCE: 15

cgcgtctcgc cccgtccacc gattgactcg ccgctcttgt ccttcctccc gctctttctt      60

ctctcccctt acggtttcaa g atg cct tcg gcc acc agc cac agc gga agc      111
                        Met Pro Ser Ala Thr Ser His Ser Gly Ser
                        1               5                   10

ggc agc aag tcg tcc gga ccg cca ccg ccg tcg ggt tcc tcc ggg aat      159
Gly Ser Lys Ser Ser Gly Pro Pro Pro Pro Ser Gly Ser Ser Gly Asn
                15                  20                  25

gag gcg ggg gcc ggg gcc gcc gcg ccg gct tcc caa cac ccc atg acc      207
Glu Ala Gly Ala Gly Ala Ala Ala Pro Ala Ser Gln His Pro Met Thr
```

```
            30                  35                  40

ggc acc ggg gct gtc cag acc gag gcc atg aag cag att ctc ggg gtg      255
Gly Thr Gly Ala Val Gln Thr Glu Ala Met Lys Gln Ile Leu Gly Val
        45                  50                  55

atc gac aag aaa ctt cgg aac ctg gag aag aaa aag ggc aag ctt gat      303
Ile Asp Lys Lys Leu Arg Asn Leu Glu Lys Lys Lys Gly Lys Leu Asp
    60                  65                  70

gat tat cag gaa cga atg aac aaa ggg gaa agg ctt aat caa gat cag      351
Asp Tyr Gln Glu Arg Met Asn Lys Gly Glu Arg Leu Asn Gln Asp Gln
75                  80                  85                  90

ctg gat gcc gtg tct aag tac cag gaa gtc aca aat aac ttg gag ttt      399
Leu Asp Ala Val Ser Lys Tyr Gln Glu Val Thr Asn Asn Leu Glu Phe
                95                  100                 105

gca aaa gaa tta cag agg agt ttc atg gca tta agc caa gat att cag      447
Ala Lys Glu Leu Gln Arg Ser Phe Met Ala Leu Ser Gln Asp Ile Gln
            110                 115                 120

aaa aca ata aag aag aca gca cgt cgg gag cag ctt atg aga gag gaa      495
Lys Thr Ile Lys Lys Thr Ala Arg Arg Glu Gln Leu Met Arg Glu Glu
        125                 130                 135

gct gaa cag aaa cgt tta aaa aca gta ctt gag ctg cag tat gtt ttg      543
Ala Glu Gln Lys Arg Leu Lys Thr Val Leu Glu Leu Gln Tyr Val Leu
    140                 145                 150

gac aaa cta gga gat gat gaa gtg aga act gac ctg aag caa ggt ttg      591
Asp Lys Leu Gly Asp Asp Glu Val Arg Thr Asp Leu Lys Gln Gly Leu
155                 160                 165                 170

aat gga gtg cca ata ttg tct gaa gag gag ttg tcg ttg tta gat gag      639
Asn Gly Val Pro Ile Leu Ser Glu Glu Glu Leu Ser Leu Leu Asp Glu
                175                 180                 185

ttc tac aaa tta gca gac cct gaa cga gac atg agc ttg agg ttg aat      687
Phe Tyr Lys Leu Ala Asp Pro Glu Arg Asp Met Ser Leu Arg Leu Asn
            190                 195                 200

gag cag tat gaa cat gcc tcc att cac ctg tgg gac ttg ctg gaa gga      735
Glu Gln Tyr Glu His Ala Ser Ile His Leu Trp Asp Leu Leu Glu Gly
        205                 210                 215

aag gaa aaa cct gta tgt gga aca act tat aaa gct cta aag gaa att      783
Lys Glu Lys Pro Val Cys Gly Thr Thr Tyr Lys Ala Leu Lys Glu Ile
    220                 225                 230

gtt gag cgt gtt ttc cag tca aac tac ttt gac agc acc cac aac cac      831
Val Glu Arg Val Phe Gln Ser Asn Tyr Phe Asp Ser Thr His Asn His
235                 240                 245                 250

cag aat ggt ctg tgt gag gaa gag gag gca gcc tca gca cct aca gtt      879
Gln Asn Gly Leu Cys Glu Glu Glu Glu Ala Ala Ser Ala Pro Thr Val
                255                 260                 265

gaa gac cag gca gct gaa gct gaa cct gag cca gtg gaa gaa tat act      927
Glu Asp Gln Ala Ala Glu Ala Glu Pro Glu Pro Val Glu Glu Tyr Thr
            270                 275                 280

gaa caa aat gag gtt gaa tca aca gag tat gta aat aga caa ttt atg      975
Glu Gln Asn Glu Val Glu Ser Thr Glu Tyr Val Asn Arg Gln Phe Met
        285                 290                 295

gca gaa aca cag ttc agc agt ggt gaa aag gag cag gta gat gat tgg     1023
Ala Glu Thr Gln Phe Ser Ser Gly Glu Lys Glu Gln Val Asp Asp Trp
    300                 305                 310

aca gtt gaa aca gtt gag gtg gta aat tca ctc cag cag caa cct cag     1071
Thr Val Glu Thr Val Glu Val Val Asn Ser Leu Gln Gln Gln Pro Gln
315                 320                 325                 330

gct gca tct cct tca gta cca gaa ccc cac tct ttg acc cca gtg gct     1119
Ala Ala Ser Pro Ser Val Pro Glu Pro His Ser Leu Thr Pro Val Ala
                335                 340                 345

caa gcc gat ccc ctc gtg aga aga cag cga gta cag gac ctt atg gca     1167
```

-continued

```
Gln Ala Asp Pro Leu Val Arg Arg Gln Arg Val Gln Asp Leu Met Ala
            350                 355                 360

caa atg cag ggg ccc tat aat ttc ata cag gat tca atg ttg gat ttt      1215
Gln Met Gln Gly Pro Tyr Asn Phe Ile Gln Asp Ser Met Leu Asp Phe
        365                 370                 375

gaa aac cag aca ctt gat cct gcc att gta tct gca cag ccg atg aat      1263
Glu Asn Gln Thr Leu Asp Pro Ala Ile Val Ser Ala Gln Pro Met Asn
    380                 385                 390

cca gca cag aac atg gac ata ccc cag ctg gtt tgc cct cca gtt cat      1311
Pro Ala Gln Asn Met Asp Ile Pro Gln Leu Val Cys Pro Pro Val His
395                 400                 405                 410

tct gaa tct aga ctt gct caa cct aat caa gtt tct gta cag cca gaa      1359
Ser Glu Ser Arg Leu Ala Gln Pro Asn Gln Val Ser Val Gln Pro Glu
                415                 420                 425

gct aca cag gtt cct ttg gtt tca tcc aca agt gag gga tat aca gca      1407
Ala Thr Gln Val Pro Leu Val Ser Ser Thr Ser Glu Gly Tyr Thr Ala
            430                 435                 440

tct caa ccc ttg tac caa cct tct cat gct act gac caa cga cca caa      1455
Ser Gln Pro Leu Tyr Gln Pro Ser His Ala Thr Asp Gln Arg Pro Gln
        445                 450                 455

aag gaa ccg att gat cag att cag gcg acg atc tct tta aat aca gac      1503
Lys Glu Pro Ile Asp Gln Ile Gln Ala Thr Ile Ser Leu Asn Thr Asp
    460                 465                 470

cag act aca gca tca tca tcc ctt cct gct gct tct cag cct caa gtg      1551
Gln Thr Thr Ala Ser Ser Ser Leu Pro Ala Ala Ser Gln Pro Gln Val
475                 480                 485                 490

ttc cag gct ggg aca agc aaa cct tta cat agc agt gga atc aat gta      1599
Phe Gln Ala Gly Thr Ser Lys Pro Leu His Ser Ser Gly Ile Asn Val
                495                 500                 505

aat gca gct cca ttc caa tcc atg caa acg gta ttc aat atg aat gcc      1647
Asn Ala Ala Pro Phe Gln Ser Met Gln Thr Val Phe Asn Met Asn Ala
            510                 515                 520

cca gtt cct cct gtt aat gaa cca gaa act tta aaa cag caa aat cag      1695
Pro Val Pro Pro Val Asn Glu Pro Glu Thr Leu Lys Gln Gln Asn Gln
        525                 530                 535

tac cag gcc agt tac aac cag agc ttt tcc agt cag cct cac caa gta      1743
Tyr Gln Ala Ser Tyr Asn Gln Ser Phe Ser Ser Gln Pro His Gln Val
    540                 545                 550

gaa caa aca gag ctt cag caa gaa cag ctt caa aca gtg gtt ggc act      1791
Glu Gln Thr Glu Leu Gln Gln Glu Gln Leu Gln Thr Val Val Gly Thr
555                 560                 565                 570

tat cat ggt tct cag gac cag ccc cat caa gtg act ggt aac cac cag      1839
Tyr His Gly Ser Gln Asp Gln Pro His Gln Val Thr Gly Asn His Gln
                575                 580                 585

cag cct cct cag cag aac act gga ttt cca cgt agc aat cag ccc tat      1887
Gln Pro Pro Gln Gln Asn Thr Gly Phe Pro Arg Ser Asn Gln Pro Tyr
            590                 595                 600

tac aac agt cgt ggt gtg tct cgt gga ggt tcc cgt ggt gct aga ggc      1935
Tyr Asn Ser Arg Gly Val Ser Arg Gly Gly Ser Arg Gly Ala Arg Gly
        605                 610                 615

ttg atg aat gga tac aga gga cct gct aat gga ttc aga gga gga tat      1983
Leu Met Asn Gly Tyr Arg Gly Pro Ala Asn Gly Phe Arg Gly Gly Tyr
    620                 625                 630

gat ggt tac cgc cct tca ttc tct act aac act cca aac agt ggt tat      2031
Asp Gly Tyr Arg Pro Ser Phe Ser Thr Asn Thr Pro Asn Ser Gly Tyr
635                 640                 645                 650

aca caa tct caa ttc agt gct ccc cgg gac tac tct ggc tat cag cgg      2079
Thr Gln Ser Gln Phe Ser Ala Pro Arg Asp Tyr Ser Gly Tyr Gln Arg
                655                 660                 665
```

-continued

```
gat gga tat cag cag aat ttc aag cga ggc tct ggg cag agt gga cca      2127
Asp Gly Tyr Gln Gln Asn Phe Lys Arg Gly Ser Gly Gln Ser Gly Pro
            670                 675                 680

cgg gga gcc cca cga ggt cgt gga ggg ccc cca aga ccc aac aga ggg      2175
Arg Gly Ala Pro Arg Gly Arg Gly Gly Pro Pro Arg Pro Asn Arg Gly
        685                 690                 695

atg ccg caa atg aac act cag caa gtg aat taa tctgattcac aggattatgt   2228
Met Pro Gln Met Asn Thr Gln Gln Val Asn
    700                 705

ttaatcgcca aaaacacact ggccagtgta ccataatatg ttaccagaag agttattatc   2288

tatttgttct ccctttcagg aaacttattg taaagggact gttttcatcc cataaagaca   2348

ggactacaat tgtcagcttt atattacctg gatatggaag gaaactattt ttactctgca   2408

tgttctgtcc taagcgtcat cttgagcctt gcacatgata ctcagattcc tcacccttgc   2468

ttaggagtaa aacataatat actttaatgg ggtgatatct ccatagttat ttgaagtggc   2528

ttggataaag caagactgac ttctgacatt ggataaaatc tacaaatcag ccctagagtc   2588

attcagtggt aactgacaaa actaaaatat ttcccttgaa aggaagatgg aaggagtgga   2648

gtgtggtttg gcagaacaac tgcatttcac agcttttcca cttaaattgg agcactgaac   2708

atttagatgc ataccgaatt atgcatgggc cctaatcaca cagacaaggc tggtgccagc   2768

cttaggcttg acacggcagt gttcaccctc tggccagacg actgtggttc aagacacatg   2828

taaattgctt tttaacagct gatactgtat aagacaaagc caaaatgcaa aattaggctt   2888

tgattggcac ttttcgaaaa atatgcaaca attaagggat ataatctgga tggccgcttc   2948

tgtacttaat gtgaaatatt tagatacctt tcaaacactt aacagtttct ttgacaatga   3008

gttttgtaag gattggtagt aaatatcatt ccttatgacg tacattgtct gtcactaatc   3068

cttggatctt gctgtattgt cacctaaatt ggtacaggta ctgatgaaaa tctaatggat   3128

aatcataaca ctcttggtta catgtttttc ctgcagcctg aaagttttta taagaaaaag   3188

acatcaaatg cctgctgctg ccaccctttt aaattgctat cttttgaaaa gcaccagtat   3248

gtgttttaga ttgatttccc tattttaggg aaatgacagt cagtagtttc acttctgatg   3308

gtataagcaa acaaataaaa catgtttata aaaaaaaaaa aaaaaaaaaa aaaaaaaaaa   3368

aaaaaaaaaa aaaaaaaa                                                  3386
```

<210> SEQ ID NO 16
<211> LENGTH: 708
<212> TYPE: PRT
<213> ORGANISM: Bos taurus

<400> SEQUENCE: 16

```
Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
```

-continued

```
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525
```

-continued

Glu Pro Glu Thr Leu Lys Gln Gln Asn Gln Tyr Gln Ala Ser Tyr Asn
530 535 540

Gln Ser Phe Ser Ser Gln Pro His Gln Val Glu Gln Thr Glu Leu Gln
545 550 555 560

Gln Glu Gln Leu Gln Thr Val Val Gly Thr Tyr His Gly Ser Gln Asp
565 570 575

Gln Pro His Gln Val Thr Gly Asn His Gln Gln Pro Pro Gln Gln Asn
580 585 590

Thr Gly Phe Pro Arg Ser Asn Gln Pro Tyr Tyr Asn Ser Arg Gly Val
595 600 605

Ser Arg Gly Gly Ser Arg Gly Ala Arg Gly Leu Met Asn Gly Tyr Arg
610 615 620

Gly Pro Ala Asn Gly Phe Arg Gly Gly Tyr Asp Gly Tyr Arg Pro Ser
625 630 635 640

Phe Ser Thr Asn Thr Pro Asn Ser Gly Tyr Thr Gln Ser Gln Phe Ser
645 650 655

Ala Pro Arg Asp Tyr Ser Gly Tyr Gln Arg Asp Gly Tyr Gln Gln Asn
660 665 670

Phe Lys Arg Gly Ser Gly Gln Ser Gly Pro Arg Gly Ala Pro Arg Gly
675 680 685

Arg Gly Gly Pro Pro Arg Pro Asn Arg Gly Met Pro Gln Met Asn Thr
690 695 700

Gln Gln Val Asn
705

<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17 atg gag ggc aag ctc gat gat tac caa gag cga atg aac aaa gga gaa 48
Met Glu Gly Lys Leu Asp Asp Tyr Gln Glu Arg Met Asn Lys Gly Glu
1 5 10 15 agg ctt aat cag gat cag ctg gat gct gtg tct aag tac cag gaa gtc 96
Arg Leu Asn Gln Asp Gln Leu Asp Ala Val Ser Lys Tyr Gln Glu Val
20 25 30 aca aat aac ttg gag ttt gcg aaa gaa ttg cag agg agt ttc atg gcg 144
Thr Asn Asn Leu Glu Phe Ala Lys Glu Leu Gln Arg Ser Phe Met Ala
35 40 45 ttg agt cag gat att cag aaa aca ata aag aag acg gca cgt cgg gag 192
Leu Ser Gln Asp Ile Gln Lys Thr Ile Lys Lys Thr Ala Arg Arg Glu
50 55 60 cag ctt atg aga gaa gaa gct gaa cag aaa cgt tta aaa act gta ctt 240
Gln Leu Met Arg Glu Glu Ala Glu Gln Lys Arg Leu Lys Thr Val Leu
65 70 75 80 gag ctg cag tat gtt ttg gac aaa ttg gga gat gaa gaa gtg cga act 288
Glu Leu Gln Tyr Val Leu Asp Lys Leu Gly Asp Glu Glu Val Arg Thr
85 90 95 gac ctg aaa caa ggt ttg aat gga gtg cca ata ctc tct gaa gaa gag 336
Asp Leu Lys Gln Gly Leu Asn Gly Val Pro Ile Leu Ser Glu Glu Glu
100 105 110 ttg tcg ctg ttg gat gag ttc tac aag tta gca gac cct gta cgg gac 384
Leu Ser Leu Leu Asp Glu Phe Tyr Lys Leu Ala Asp Pro Val Arg Asp
115 120 125

-continued

```
atg agc ttg agg ttg aat gag cag tat gag cat gcc tcc att cac ctg      432
Met Ser Leu Arg Leu Asn Glu Gln Tyr Glu His Ala Ser Ile His Leu
    130                 135                 140

tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160

aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175

gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190

acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205

cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220

gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240

cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255

cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270

ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285

cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300

tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320

gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335

tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350

cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365

gag ggg tat aca gca tct cag ccc ttg tac cag cct tct cat gct aca     1152
Glu Gly Tyr Thr Ala Ser Gln Pro Leu Tyr Gln Pro Ser His Ala Thr
    370                 375                 380

gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400

tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415

tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430

agt ggg atc aat gta aat gca gcg cca ttc cag tcc atg caa acg gtg     1344
Ser Gly Ile Asn Val Asn Ala Ala Pro Phe Gln Ser Met Gln Thr Val
```

```
        435                 440                 445

ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460

aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480

ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495

acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510

acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525

agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
    530                 535                 540

cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560

ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575

aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590

ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605

cag agt gga ccc cgg gga gcc cca cga ggt cgt gga ggg ccc cca aga     1872
Gln Ser Gly Pro Arg Gly Ala Pro Arg Gly Arg Gly Gly Pro Pro Arg
    610                 615                 620

ccc aac aga ggg atg ccg caa atg aac act cag caa gtg aat taa         1917
Pro Asn Arg Gly Met Pro Gln Met Asn Thr Gln Gln Val Asn
625                 630                 635

tctgattcac aggattatct ttaatcgcca aaacacactg gccagtgtac cataatatgt   1977

taccagaaga gttattatct atttgttctc cctttcagga aacttattgt aaagggactg   2037

ttttcatccc ataaagacag gactacagtt gtcagcttta tattacctgg atatggaagg   2097

aaactatttt tactctgcat gttctgtcct aagcgtcatc ttgagccttg cacatgatac   2157

tcagattcct ttcccttgct taggagtaaa acataatata ctttatgggg tgataatatc   2217

tccatagtta tttgaagtgg cttggaaaaa gcaagattga cttttgacat tggataaaat   2277

ctacaaatca gccctagagt ttcatggtca ttcacaaaac taaaatattt cccttgaaag   2337

gaagatggaa ggactggagt gtggtttggc agaacaactg catttcacag cttttcctat   2397

taaattggag cactgaatgt taaatgcata ccaaattatg catgggccct taatcacaca   2457

tacatggcta ccagctttga cacagcacta ttcatcctct ggccaaacga ctgtggttaa   2517

aaacacgtgt aaattgcttt ttaacagctg atactgtaaa agacaaagct aaaatgcaaa   2577

attaggcttt cattggcact tttcgaaaaa tatgcaacaa atttgggatg taatctggat   2637

ggccacttct gtacttaatg tgaagtattt agataccttt ttgaacactt aacagtttct   2697

tcgacaatga cttttgtaag gattggtagt atatatcatt ccttatgaca tacattgtct   2757

gttgctaatc cttggatctt gctgtattgt cacctaaatt ggtacaggta ctgatgaaaa   2817
```

-continued tctctcatgg ataaacctaa cactcttcgt cacatgtttt tcctgcagcc tgaaggtttt 2877 taaaaggaaa agatatcaaa tgcctgctgc taccaccctt ttaaattgct atcttttgaa 2937 aagcaccagt atgtgttttt agattgattt ccctatttta gggaaatgac agtcagtagt 2997 ttcagttctg atggtataag caaagcaaat aaaacgtgtt tataaaagtt gtatcttgaa 3057 acactggtgt tcaacagcta gcagcttctg tggttcaccc cctgccttgt tagtgttacc 3117 catttatggt tatctccagc agcaatttct cta 3150

<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1 5 10 15

Arg Leu Asn Gln Asp Gln Leu Asp Ala Val Ser Lys Tyr Gln Glu Val
20 25 30

Thr Asn Asn Leu Glu Phe Ala Lys Glu Leu Gln Arg Ser Phe Met Ala
35 40 45

Leu Ser Gln Asp Ile Gln Lys Thr Ile Lys Lys Thr Ala Arg Arg Glu
50 55 60

Gln Leu Met Arg Glu Glu Ala Glu Gln Lys Arg Leu Lys Thr Val Leu
65 70 75 80

Glu Leu Gln Tyr Val Leu Asp Lys Leu Gly Asp Glu Glu Val Arg Thr
85 90 95

Asp Leu Lys Gln Gly Leu Asn Gly Val Pro Ile Leu Ser Glu Glu Glu
100 105 110

Leu Ser Leu Leu Asp Glu Phe Tyr Lys Leu Ala Asp Pro Val Arg Asp
115 120 125

Met Ser Leu Arg Leu Asn Glu Gln Tyr Glu His Ala Ser Ile His Leu
130 135 140

Trp Asp Leu Leu Glu Gly Lys Glu Lys Ser Val Cys Gly Thr Thr Tyr
145 150 155 160

Lys Ala Leu Arg Glu Ile Val Glu Arg Val Phe Gln Ser Asn Tyr Phe
165 170 175

Asp Ser Thr His Asn His Gln Asn Gly Leu Cys Glu Glu Glu Ala
180 185 190

Thr Ser Ala Pro Thr Ala Glu Asp Gln Gly Ala Glu Ala Glu Pro Glu
195 200 205

Pro Ala Glu Glu Tyr Thr Glu Gln Ser Glu Val Glu Ser Thr Glu Tyr
210 215 220

Val Asn Arg Gln Phe Met Ala Glu Ala Gln Phe Ser Gly Glu Lys Glu
225 230 235 240

Gln Val Asp Glu Trp Thr Val Glu Thr Val Glu Val Val Asn Ser Leu
245 250 255

Gln Gln Gln Pro Gln Ala Ala Ser Pro Ser Val Pro Glu Pro His Ser
260 265 270

Leu Thr Pro Val Ala Gln Ala Asp Pro Leu Val Arg Arg Gln Arg Val
275 280 285

Gln Asp Leu Met Ala Gln Met Gln Gly Pro Tyr Asn Phe Ile Gln Asp
290 295 300

Ser Met Leu Asp Phe Glu Asn Gln Thr Leu Asp Pro Ala Ile Val Ser

```
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635


<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178
```

```
atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca      274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg      370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320
```

-continued

```
gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
```

-continued

```
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt cgt     2242
Lys Arg Gly Ser Gly Gln Ser Gly Pro Arg Gly Ala Pro Arg Gly Arg
        675                 680                 685

gga ggg ccc cca aga ccc aac aga ggg atg ccg caa atg aac act cag     2290
Gly Gly Pro Pro Arg Pro Asn Arg Gly Met Pro Gln Met Asn Thr Gln
    690                 695                 700

caa gtg aat taa tgtgatacac aggattatgt ttaatcgcca aaaacacact         2342
Gln Val Asn
705

ggccagtgta ccataatatg ttaccagaag agttattatc tatttgttct ccctttcagg   2402

aaacttattg taaagggact gttttcatcc cataaagaca ggactgcaat tgtcagcttt   2462

acattacctg gatatggaag gaaactattt ttattctgca tgttctgtcc taagcgtcat   2522

cttgagcctt gcacacaata caatactcag attcctcacc cttgcttagg agtaaaacat   2582

tatatactta tggggtgata atatctccat agttagttga agtggcttgg aaaaaaaatg   2642

caagattgaa tttttgacct tggataaaat ctacaatcag ccctagaact attcagtggt   2702

aattgacaaa gttaaagcat ttctttgaa aggaagatgg aaggagtgga gtgtggttta    2762

gcaaaactgc atttcatagc tttcccatta aattggagca ccgacagatt aaaagcatac   2822

caaattatgc atgggtcctt actcacacaa gtgaggctgg ctaccagcct tgacatagca   2882

ctcactagtc ttctggccaa acgactgtga ttaaaacaca tgtaaattgc tctttagtag   2942

tggatactgt gtaagacaaa gccaaattgc aaatcaggct ttgattggct cttctggaaa   3002

atatgcatca aatatggggg ataatctgga tgggctgctg ctgtgctcaa tgtgaactat   3062

ttagatacct ttggaacact taacagtttc tctgaacaat gacttacatg gggattggtc   3122

ctgtttgtca ttcctcacca taattgcatt gtcatcacta atccttggat cttgctgtat   3182

tgttactcaa attggtaata ggtactgatg gaaatcgcta atggatggat aatcataaca   3242

cttttggtca catgttttct cctgcagcct gaaagttctt aaagaaaaag atatcaaatg   3302

cctgctgcta ccaccctttt aaattgctat ctttagaaaa gcaccggtat gtgttttaga   3362

ttcatttccc tgttttaggg aaatgacagg cagtagtttc agttctgatg gcaaaacaaa   3422

taaaaacatg tttctaaaag ttgtatcttg aaacactggt gttcaacagc tagcagctaa   3482

agtaattcaa cccatgcatt gctagtgtca cagcctttgg ttatgtctag tagctgtttc   3542

tgaagtattt tcatttatct tttgtcaaat ttaaccctgt ttgaattctc tcctttcctc   3602

aaggagacac ttatgttcaa agtgttgatt ctttgcctta ggtgcataga gagtagacag   3662

tttggagatg gaaaggttag cagtgactta gccatatgtt ctgtgttgga atttgtgcta   3722

gcagtttgag cactagctct gcgtgcctat gaactgaatg ctgcttgtcc cattccattt   3782

tatgtcatgg agaaataatt ccacttggta acacaaaggc taagttaatg ttattttctg   3842

tacagaaatt aaattttact tttagccttt tgtaaacttt tttttttttt ttccaagccg   3902

gtatcagcta ctcaaaacaa ttctcagata ttcatcatta gacaactgga gtttttgctg   3962

gttttgtagc ctactaaaac tgctgaggct gttgaacatt ccacattcaa aagttttgta   4022

gggtggtgga taatggggaa gcttcaatgt ttattttaaa ataaataaaa taagttcttg   4082
```

```
acttttctca tgtgtggtta tggtacatca tattggaagg gttatctgtt tacttttgcc   4142
aagactattt tgccagcacc tacacttgtg tgctttaaaa gacaactacc tgggatgtac   4202
cacaaccata tgttaattgt attttattgg gatggataaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg atttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
tgcttattct caggttcatt cactaaggtg cttggcagac aaccagtttc taagtgcaga   5102
atgtagttaa gcagcttcat atatgtgcca ggcaatttgt tttgttaaat tttcatctac   5162
ttaaggaaat agggtattgt agcttaggct gatcataccc ttcatttcaa ccttaagctc   5222
tcaacctgca tccatccgac ttgagctatt aagtacttta gttttatcga gtataagtta   5282
acagaaaaag taaattaagc tttgccttta ctattttgaa tttatataca ttctggaaaa   5342
acttagaaac tgttgtatat ttcattagat taaattatat gaaaatgtga ttgtttatag   5402
caaagcctgt gagttgcata caccctaagg aaaactcctt aagtgctcct tgaagagaga   5462
agaaacaatt ctgggtctgg tctttttaag aacaaagcta gactactgta tgttagcact   5522
gtacattaat agtctgttgt gaagcttgag cagtttcctg catagccttg atccttcacc   5582
gttggcattg aaaatagcag tatccctgat gtacttaaaa cttaaagtca ggttttggta   5642
tatttatttg taagtcttaa tttcctctaa atactatatc tctttagcga gacaacctga   5702
aatttattag cacatttggg tatctcttgc ttggcattat ggccagtgtt aactattcag   5762
tggtgaaaaa attacccctc aagacactgg agtgacccca gatgtgtgta gtaagtggca   5822
tggttcaact gtgtggttaa tgataaatat atgacttagt cggtatgatc tggaaagact   5882
tgattgaaag ataattcagc tgacataagg atgagtgagg agtggcaaac tggataaaag   5942
agtcaagaga cctgtattcc agtgactcct gttttgttta agcattagca agatctgtct   6002
ggggaaactg gatagggcag ttttcttcca tgtttagttt ttgtctcaac atttggaagc   6062
tattgaaggt tttaaaatgg tgtgtattgt tttttttgg gggggggtg gccagaatag   6122
tgggtcatct aataaaactg ccatttaaaa gatcaaaaaa aaaaaaaaaa aaaaaaaaa    6181
```

<210> SEQ ID NO 20
<211> LENGTH: 707
<212> TYPE: PRT
<213> ORGANISM: Mus musculus

<400> SEQUENCE: 20

-continued

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
```

```
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)

<400> SEQUENCE: 21

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                        1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25
```

-continued

```
gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345
```

```
tca gat cca ctt gtg aga agg cag cgt gta caa gat ctt atg gca caa      1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
```

-continued

```
            655                 660                 665

tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680

gcc cca cga ggt cgt gga ggg ccc cca aga ccc aac aga ggg atg ccg     2235
Ala Pro Arg Gly Arg Gly Gly Pro Pro Arg Pro Asn Arg Gly Met Pro
    685                 690                 695

caa atg aac act cag caa gtg aat taa tgtgatacac aggattatgt           2282
Gln Met Asn Thr Gln Gln Val Asn
700                 705

ttaatcgcca aaaacacact ggccagtgta ccataatatg ttaccagaag agttattatc   2342

tatttgttct ccctttcagg aaacttattg taaagggact gttttcatcc cataaagaca   2402

ggactgcaat tgtcagcttt acattacctg gatatggaag gaaactattt ttattctgca   2462

tgttctgtcc taagcgtcat cttgagcctt gcacacaata caatactcag attcctcacc   2522

cttgcttagg agtaaaacat tatatactta tggggtgata atatctccat agttagttga   2582

agtggcttgg aaaaaaaatg caagattgaa tttttgacct tggataaaat ctacaatcag   2642

ccctagaact attcagtggt aattgacaaa gttaaagcat ttctttgaa aggaagatgg   2702

aaggagtgga gtgtggttta gcaaaactgc atttcatagc tttcccatta aattggagca   2762

ccgacagatt aaaagcatac caaattatgc atgggtcctt actcacacaa gtgaggctgg   2822

ctaccagcct tgacatagca ctcactagtc ttctggccaa acgactgtga ttaaaacaca   2882

tgtaaattgc tctttagtag tggatactgt gtaagacaaa gccaaattgc aaatcaggct   2942

ttgattggct cttctggaaa atatgcatca aatatggggg ataatctgga tgggctgctg   3002

ctgtgctcaa tgtgaactat ttagatacct ttggaacact taacagtttc tctgaacaat   3062

gacttacatg gggattggtc ctgtttgtca ttcctcacca taattgcatt gtcatcacta   3122

atccttggat cttgctgtat tgttactcaa attggtaata ggtactgatg gaaatcgcta   3182

atggatggat aatcataaca cttttggtca catgttttct cctgcagcct gaaagttctt   3242

aaagaaaaag atatcaaatg cctgctgcta ccaccctttt aaattgctat ctttagaaaa   3302

gcaccggtat gtgttttaga ttcatttccc tgttttaggg aaatgacagg cagtagtttc   3362

agttctgatg gcaaaacaaa taaaaacatg tttctaaaag ttgtatcttg aaacactggt   3422

gttcaacagc tagcagctaa agtaattcaa cccatgcatt gctagtgtca cagcctttgg   3482

ttatgtctag tagctgtttc tgaagtattt tcatttatct tttgtcaaat ttaaccctgt   3542

ttgaattctc tcctttcctc aaggagacac ttatgttcaa agtgttgatt ctttgcctta   3602

ggtgcataga gagtagacag tttggagatg gaaaggttag cagtgactta gccatatgtt   3662

ctgtgttgga atttgtgcta gcagtttgag cactagctct gcgtgcctat gaactgaatg   3722

ctgcttgtcc cattccattt tatgtcatgg agaaataatt ccacttggta acacaaaggc   3782

taagttaatg ttattttctg tacagaaatt aaattttact tttagccttt tgtaaacttt   3842

tttttttttt ttccaagccg gtatcagcta ctcaaaacaa ttctcagata ttcatcatta   3902

gacaactgga gtttttgctg gttttgtagc ctactaaaac tgctgaggct gttgaacatt   3962

ccacattcaa aagttttgta gggtggtgga taatggggaa gcttcaatgt ttattttaaa   4022

ataaataaaa taagttcttg acttttctca tgtgtggtta tggtacatca tattggaagg   4082

gttatctgtt tacttttgcc aagactattt tgccagcacc tacacttgtg tgctttaaaa   4142

gacaactacc tgggatgtac cacaaccata tgttaattgt attttattgg gatggataaa   4202

atgtttgtgg tttattggat aatccctaga tggtgtgtta cgtgtgtaga atataatttt   4262
```

```
atgatagtaa gaaagcaaaa ttgaagaaaa taagtttagt attgaatttg agttctgaag   4322
tgaattcagg gaatgtctca cgtttcgggc ttctacccaa agtgtagggc agaaggtgta   4382
aaagttgttt gtagtttgac ttgtttattt tttaagttgc ttattccttt caacagcaac   4442
atatcattag ctgtcattct accattgcag ttctagtgag ttttaacgtc tgcattcaag   4502
actgttttaa aagcaacctc actggacaga gaactgctaa agtcttttcc ttaagatctg   4562
agtctttgtt actcagtatc ttctataata tgcaaatgct tgtctagagg cagaagacct   4622
tttgtttggt caagtgtgta ttttaccaga gtacagggaa ctgatggtcc tacatgtctc   4682
ttagtgtagt aagactataa aatcttttgt acatgcacaa ttcacagtat gtttagatac   4742
cacgtgtata atgccccccc ctcccccagg tagcatgcca ttgatgactt tttgcttagg   4802
gccattttat taccagggcc ttaatattcc taaaaagatg atttttttc atcctttctc   4862
ctcttttgat cattgtatct tgatattaaa aacatgacct tccaatgatt gtagtaaatt   4922
aacttctata gttcttttgt ctctatatgt attcatatat atgctattgt atagagactt   4982
caaggagaca tggagatgca tgcttattct caggttcatt cactaaggtg cttggcagac   5042
aaccagtttc taagtgcaga atgtagttaa gcagcttcat atatgtgcca ggcaatttgt   5102
tttgttaaat tttcatctac ttaaggaaat agggtattgt agcttaggct gatcataccc   5162
ttcatttcaa ccttaagctc tcaacctgca tccatccgac ttgagctatt aagtacttta   5222
gttttatcga gtataagtta acagaaaaag taaattaagc tttgccttta ctattttgaa   5282
tttatataca ttctggaaaa acttagaaac tgttgtatat ttcattagat taaattatat   5342
gaaaatgtga ttgtttatag caaagcctgt gagttgcata caccctaagg aaaactcctt   5402
aagtgctcct tgaagagaga agaaacaatt ctgggtctgg tctttttaag aacaaagcta   5462
gactactgta tgttagcact gtacattaat agtctgttgt gaagcttgag cagtttcctg   5522
catagccttg atccttcacc gttggcattg aaaatagcag tatccctgat gtacttaaaa   5582
cttaaagtca ggttttggta tatttatttg taagtcttaa tttcctctaa atactatatc   5642
tctttagcga gacaacctga aatttattag cacatttggg tatctcttgc ttggcattat   5702
ggccagtgtt aactattcag tggtgaaaaa attacccctc aagacactgg agtgacccca   5762
gatgtgtgta gtaagtggca tggttcaact gtgtggttaa tgataaatat atgacttagt   5822
cggtatgatc tggaaagact tgattgaaag ataattcagc tgacataagg atgagtgagg   5882
agtggcaaac tggataaaag agtcaagaga cctgtattcc agtgactcct gttttgttta   5942
agcattagca agatctgtct ggggaaactg gatagggcag ttttcttcca tgtttagttt   6002
ttgtctcaac atttggaagc tattgaaggt tttaaaatgg tgtgtattgt tttttttggg   6062
gggggggtg gccagaatag tgggtcatct aataaaactg ccatttaaaa gatcaaaaaa   6122
aaaaaaaaa aaaaaaaaa                                                 6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30
```

-continued

```
Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
```

```
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc      171
                    Met Pro Ser Ala Thr Ser His Ser Gly Ser Gly
                    1               5                   10

agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc      315
Thr Gly Ala Val Gln Thr Glu Ala Met Lys Gln Ile Leu Gly Val Ile
```

-continued

```
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag acg ctt gat cct gcc att gta     1275
```

-continued

```
Met Gln Gly Pro Tyr Asn Phe Ile Gln Thr Leu Asp Pro Ala Ile Val
    365                 370                 375

tcc gca cag cct atg aac cct acc cag aac atg gat atg cct cag ctg     1323
Ser Ala Gln Pro Met Asn Pro Thr Gln Asn Met Asp Met Pro Gln Leu
380                 385                 390                 395

gtt tgc cct cag gtt cat tct gaa tct aga ctt gcc caa tct aat caa     1371
Val Cys Pro Gln Val His Ser Glu Ser Arg Leu Ala Gln Ser Asn Gln
                400                 405                 410

gtt cct gta caa cca gaa gcc aca cag gtt cct ttg gtt tca tcc aca     1419
Val Pro Val Gln Pro Glu Ala Thr Gln Val Pro Leu Val Ser Ser Thr
            415                 420                 425

agt gag ggg tat aca gca tct cag ccc ttg tac cag cca tct cat gct     1467
Ser Glu Gly Tyr Thr Ala Ser Gln Pro Leu Tyr Gln Pro Ser His Ala
        430                 435                 440

acg gag cag cgg ccg cag aaa gag cca atg gat cag att cag gca aca     1515
Thr Glu Gln Arg Pro Gln Lys Glu Pro Met Asp Gln Ile Gln Ala Thr
    445                 450                 455

ata tct ttg aat aca gac cag act aca gca tcc tca tcc ctt cct gct     1563
Ile Ser Leu Asn Thr Asp Gln Thr Thr Ala Ser Ser Ser Leu Pro Ala
460                 465                 470                 475

gct tct cag cct caa gtg ttc cag gct ggg aca agt aaa cct ttg cac     1611
Ala Ser Gln Pro Gln Val Phe Gln Ala Gly Thr Ser Lys Pro Leu His
                480                 485                 490

agc agt gga atc aat gta aat gca gct cca ttc cag tcc atg caa acg     1659
Ser Ser Gly Ile Asn Val Asn Ala Ala Pro Phe Gln Ser Met Gln Thr
            495                 500                 505

gtg ttc aat atg aat gct cca gtc cct cct gct aat gaa cca gaa acg     1707
Val Phe Asn Met Asn Ala Pro Val Pro Pro Ala Asn Glu Pro Glu Thr
        510                 515                 520

tta aaa caa cag agt cag tac cag gcc act tat aac cag agt ttt tcc     1755
Leu Lys Gln Gln Ser Gln Tyr Gln Ala Thr Tyr Asn Gln Ser Phe Ser
    525                 530                 535

agt cag cct cac caa gtg gaa caa aca gag ctt caa caa gac caa ctg     1803
Ser Gln Pro His Gln Val Glu Gln Thr Glu Leu Gln Gln Asp Gln Leu
540                 545                 550                 555

caa acg gtg gtt ggc act tac cat gga tcc cag gac cag cct cat caa     1851
Gln Thr Val Val Gly Thr Tyr His Gly Ser Gln Asp Gln Pro His Gln
                560                 565                 570

gtg cct ggt aac cac cag caa ccc cca cag cag aac act ggc ttt cca     1899
Val Pro Gly Asn His Gln Gln Pro Pro Gln Gln Asn Thr Gly Phe Pro
            575                 580                 585

cgt agc agt cag cct tat tac aac agt cgt ggg gta tct cga gga ggg     1947
Arg Ser Ser Gln Pro Tyr Tyr Asn Ser Arg Gly Val Ser Arg Gly Gly
        590                 595                 600

tct cgt ggt gcc aga ggc ttg atg aat gga tac agg ggc cct gcc aat     1995
Ser Arg Gly Ala Arg Gly Leu Met Asn Gly Tyr Arg Gly Pro Ala Asn
    605                 610                 615

gga ttt aga gga gga tat gat ggt tac cgc cct tca ttc tcg aac act     2043
Gly Phe Arg Gly Gly Tyr Asp Gly Tyr Arg Pro Ser Phe Ser Asn Thr
620                 625                 630                 635

cca aac agt ggt tat tca cag tct cag ttc act gct ccc cgg gac tac     2091
Pro Asn Ser Gly Tyr Ser Gln Ser Gln Phe Thr Ala Pro Arg Asp Tyr
                640                 645                 650

tct ggt tac cag cgg gat gga tat cag cag aat ttc aag cga ggc tct     2139
Ser Gly Tyr Gln Arg Asp Gly Tyr Gln Gln Asn Phe Lys Arg Gly Ser
            655                 660                 665

ggg cag agt gga cca cgg gga gcc cca cga ggt cgt gga ggg ccc cca     2187
Gly Gln Ser Gly Pro Arg Gly Ala Pro Arg Gly Arg Gly Gly Pro Pro
        670                 675                 680
```

-continued

```
aga ccc aac aga ggg atg ccg caa atg aac act cag caa gtg aat taa     2235
Arg Pro Asn Arg Gly Met Pro Gln Met Asn Thr Gln Gln Val Asn
    685                 690                 695

tgtgatacac aggattatgt ttaatcgcca aaaacacact ggccagtgta ccataatatg   2295

ttaccagaag agttattatc tatttgttct ccctttcagg aaacttattg taaagggact   2355

gttttcatcc cataaagaca ggactgcaat tgtcagcttt acattacctg gatatggaag   2415

gaaactattt ttattctgca tgttctgtcc taagcgtcat cttgagcctt gcacacaata   2475

caatactcag attcctcacc cttgcttagg agtaaaacat tatatactta tggggtgata   2535

atatctccat agttagttga agtggcttgg aaaaaaaatg caagattgaa tttttgacct   2595

tggataaaat ctacaatcag ccctagaact attcagtggt aattgacaaa gttaaagcat   2655

tttctttgaa aggaagatgg aaggagtgga gtgtggttta gcaaaactgc atttcatagc   2715

tttcccatta aattggagca ccgacagatt aaaagcatac caaattatgc atgggtcctt   2775

actcacacaa gtgaggctgg ctaccagcct tgacatagca ctcactagtc ttctggccaa   2835

acgactgtga ttaaaacaca tgtaaattgc tctttagtag tggatactgt gtaagacaaa   2895

gccaaattgc aaatcaggct ttgattggct cttctggaaa atatgcatca aatatggggg   2955

ataatctgga tgggctgctg ctgtgctcaa tgtgaactat ttagatacct ttggaacact   3015

taacagtttc tctgaacaat gacttacatg ggattggtc ctgtttgtca ttcctcacca    3075

taattgcatt gtcatcacta atccttggat cttgctgtat tgttactcaa attggtaata   3135

ggtactgatg gaaatcgcta atggatggat aatcataaca cttttggtca catgttttct   3195

cctgcagcct gaaagttctt aaagaaaaag atatcaaatg cctgctgcta ccaccctttt   3255

aaattgctat ctttagaaaa gcaccggtat gtgttttaga ttcatttccc tgttttaggg   3315

aaatgacagg cagtagtttc agttctgatg gcaaaacaaa taaaaacatg tttctaaaag   3375

ttgtatcttg aaacactggt gttcaacagc tagcagctaa agtaattcaa cccatgcatt   3435

gctagtgtca cagcctttgg ttatgtctag tagctgtttc tgaagtattt tcatttatct   3495

tttgtcaaat ttaaccctgt ttgaattctc tcctttcctc aaggagacac ttatgttcaa   3555

agtgttgatt ctttgcctta ggtgcataga gagtagacag tttggagatg gaaaggttag   3615

cagtgactta gccatatgtt ctgtgttgga atttgtgcta gcagtttgag cactagctct   3675

gcgtgcctat gaactgaatg ctgcttgtcc cattccattt tatgtcatgg agaaataatt   3735

ccacttggta acacaaaggc taagttaatg ttattttctg tacagaaatt aaattttact   3795

tttagccttt tgtaaacttt tttttttttt ttccaagccg gtatcagcta ctcaaaacaa   3855

ttctcagata ttcatcatta gacaactgga gtttttgctg gttttgtagc ctactaaaac   3915

tgctgaggct gttgaacatt ccacattcaa aagttttgta gggtggtgga taatggggaa   3975

gcttcaatgt ttattttaaa ataaataaaa taagttcttg acttttctca tgtgtggtta   4035

tggtacatca tattggaagg gttatctgtt tacttttgcc aagactattt tgccagcacc   4095

tacacttgtg tgctttaaaa gacaactacc tgggatgtac cacaaccata tgttaattgt   4155

attttattgg gatggataaa atgtttgtgg tttattggat aatccctaga tggtgtgtta   4215

cgtgtgtaga atataatttt atgatagtaa gaaagcaaaa ttgaagaaaa taagtttagt   4275

attgaatttg agttctgaag tgaattcagg gaatgtctca cgtttcgggc ttctacccaa   4335

agtgtagggc agaaggtgta aaagttgttt gtagtttgac ttgtttattt tttaagttgc   4395

ttattccttt caacagcaac atatcattag ctgtcattct accattgcag ttctagtgag   4455

ttttaacgtc tgcattcaag actgttttaa aagcaacctc actggacaga gaactgctaa   4515
```

```
agtcttttcc ttaagatctg agtctttgtt actcagtatc ttctataata tgcaaatgct   4575

tgtctagagg cagaagacct tttgtttggt caagtgtgta ttttaccaga gtacagggaa   4635

ctgatggtcc tacatgtctc ttagtgtagt aagactataa aatcttttgt acatgcacaa   4695

ttcacagtat gtttagatac cacgtgtata atgccccccc ctcccccagg tagcatgcca   4755

ttgatgactt tttgcttagg gccattttat taccagggcc ttaatattcc taaaaagatg   4815

atttttttc atcctttctc ctcttttgat cattgtatct tgatattaaa aacatgacct   4875

tccaatgatt gtagtaaatt aacttctata gttcttttgt ctctatatgt attcatatat   4935

atgctattgt atagagactt caaggagaca tggagatgca tgcttattct caggttcatt   4995

cactaaggtg cttggcagac aaccagtttc taagtgcaga atgtagttaa gcagcttcat   5055

atatgtgcca ggcaatttgt tttgttaaat tttcatctac ttaaggaaat agggtattgt   5115

agcttaggct gatcataccc ttcatttcaa ccttaagctc tcaacctgca tccatccgac   5175

ttgagctatt aagtacttta gttttatcga gtataagtta acagaaaaag taaattaagc   5235

tttgccttta ctattttgaa tttatataca ttctggaaaa acttagaaac tgttgtatat   5295

ttcattagat taaattatat gaaaatgtga ttgtttatag caaagcctgt gagttgcata   5355

caccctaagg aaaactcctt aagtgctcct tgaagagaga agaaacaatt ctgggtctgg   5415

tctttttaag aacaaagcta gactactgta tgttagcact gtacattaat agtctgttgt   5475

gaagcttgag cagtttcctg catagccttg atccttcacc gttggcattg aaaatagcag   5535

tatccctgat gtacttaaaa cttaaagtca ggttttggta tatttatttg taagtcttaa   5595

tttcctctaa atactatatc tctttagcga gacaacctga aatttattag cacatttggg   5655

tatctcttgc ttggcattat ggccagtgtt aactattcag tggtgaaaaa attacccctc   5715

aagacactgg agtgacccca gatgtgtgta gtaagtggca tggttcaact gtgtggttaa   5775

tgataaatat atgacttagt cggtatgatc tggaaagact tgattgaaag ataattcagc   5835

tgacataagg atgagtgagg agtggcaaac tggataaaag agtcaagaga cctgtattcc   5895

agtgactcct gttttgttta agcattagca agatctgtct ggggaaactg gatagggcag   5955

ttttcttcca tgtttagttt ttgtctcaac atttggaagc tattgaaggt tttaaaatgg   6015

tgtgtattgt tttttttgg gggggggtg gccagaatag tgggtcatct aataaaactg   6075

ccatttaaaa gatcaaaaaa aaaaaaaaaa aaaaaaaaa                        6114

<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
```

-continued

```
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510
```

```
Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685

Met Pro Gln Met Asn Thr Gln Gln Val Asn
    690                 695


<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
```

-continued

```
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415
```

-continued

```
caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
            485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
            565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
            645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt aat     2242
Lys Arg Gly Ser Gly Gln Ser Gly Pro Arg Gly Ala Pro Arg Gly Asn
        675                 680                 685

ata ttg tgg tgg tga tcctagctcc tatgtggagc ttctgttctg gccttggaag     2297
Ile Leu Trp Trp
    690

aactgttcat agtccgcatg taggttacat gttaggaata catttatctt ttccagactt   2357

gttgctaaag attaaatgaa atgctctgtt tctaaaattt catcttgaat ccaaatttta   2417

atttttgaat gactttccct gctgttgtct tcaaaatcag aacattttct ctgcctcaga   2477

aaagcgtttt tccaactgga aatttatttt tcaggtctta aaacctgcta aatgttttta   2537
```

```
ggaagtacct actgaaactt tttgtaagac atttttggaa cgagcttgaa catttatata   2597

aatttattac cctctttgat ttttgaaaca tgcatattat atttaggctg agaagcccctt  2657

caaatggcca gataagccac agttttagct agagaaccat ttagaattga cataactaat   2717

ctaaacttga acacttttag gaccaatgtt agtgttctaa ataccaacat atttctgatg   2777

tttaaacaga tctcccaaat tcttaggacc ttgatgtcat taaaatttag aatgacaagc   2837

ttaagaggct ttagtttcat ttgtttttca agtaatgaaa aataatttct tacatgggca   2897

gatagttaat ttgttgaaca attacaggta gcatttcatg taatctgatg ttctaaatgg   2957

ttctcttatt gaaggaggtt aaagaattag gtttcttaca gtttttggct ggccatgaca   3017

tgtataaaat gtatattaag gaggaattat aaagtacttt aatttgaatg ctagtggcaa   3077

ttgatcatta agaaagtact ttaaagcaaa aggttaatgg gtcatctggg aaaaatactg   3137

aagtatcaaa ggtatttgca tgtgaatgtg ggttatgttc ttctatccca ccttgtagca   3197

tattctatga aagttgagtt aaatgatagc taaaatatct gtttcaacag catgtaaaaa   3257

gttattttaa ctgttacaag tcattataca attttgaatg ttctgtagtt tctttttaac   3317

agtttaggta caaaggtctg ttttcattct ggtgcttttt attaattttg atagtatgat   3377

gtcacttcct attgaaatgt aagctagcgt gtaccttaga atgtgagctc catgagagca   3437

ggtaccttgt ttgtcttcac tgctgtatct attcccaacg cctcatgaca gtgcctggca   3497

catagtaggc actcaataaa tacttgttga atgaatgaaa aaaaaaaaaa a            3548
```

```
<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190
```

-continued

```
Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
```

```
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185
```

-continued

```
tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc     1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct     1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa     1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag     1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc     1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat     1659
Gln Ala Gly Thr Ser Lys Pro Leu His Ser Ser Gly Ile Asn Val Asn
```

-continued

```
            495                 500                 505

gca gct cca ttc cag tcc atg caa acg gtg ttc aat atg aat gct cca     1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac     1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa     1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac     1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa     1899
His Gly Ser Gln Asp Gln Pro His Gln Val Pro Gly Asn His Gln Gln
            575                 580                 585

ccc cca cag cag aac act ggc ttt cca cgt agc agt cag cct tat tac     1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg     1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat     2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag     2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga     2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680

gcc cca cga ggt aat ata ttg tgg tgg tga tcctagctcc tatgtggagc       2237
Ala Pro Arg Gly Asn Ile Leu Trp Trp
    685                 690

ttctgttctg gccttggaag aactgttcat agtccgcatg taggttacat gttaggaata   2297

catttatctt ttccagactt gttgctaaag attaaatgaa atgctctgtt tctaaaattt   2357

catcttgaat ccaaatttta atttttgaat gactttccct gctgttgtct tcaaaatcag   2417

aacattttct ctgcctcaga aaagcgtttt tccaactgga aatttatttt tcaggtctta   2477

aaacctgcta aatgttttta ggaagtacct actgaaactt tttgtaagac atttttggaa   2537

cgagcttgaa catttatata aatttattac cctctttgat ttttgaaaca tgcatattat   2597

atttaggctg agaagccctt caaatggcca gataagccac agttttagct agagaaccat   2657

ttagaattga cataactaat ctaaacttga acacttttag gaccaatgtt agtgttctaa   2717

ataccaacat atttctgatg tttaaacaga tctcccaaat tcttaggacc ttgatgtcat   2777

taaaatttag aatgacaagc ttaagaggct ttagtttcat ttgtttttca agtaatgaaa   2837

aataatttct tacatgggca gatagttaat ttgttgaaca attacaggta gcatttcatg   2897

taatctgatg ttctaaatgg ttctcttatt gaaggaggtt aaagaattag gtttcttaca   2957

gtttttggct ggccatgaca tgtataaaat gtatattaag gaggaattat aaagtacttt   3017

aatttgaatg ctagtggcaa ttgatcatta agaaagtact ttaaagcaaa aggttaatgg   3077

gtcatctggg aaaaatactg aagtatcaaa ggtatttgca tgtgaatgtg ggttatgttc   3137
```

-continued

```
ttctatccca ccttgtagca tattctatga aagttgagtt aaatgatagc taaaatatct   3197

gtttcaacag catgtaaaaa gttattttaa ctgttacaag tcattataca attttgaatg   3257

ttctgtagtt tctttttaac agtttaggta caaaggtctg ttttcattct ggtgcttttt   3317

attaattttg atagtatgat gtcacttcct attgaaatgt aagctagcgt gtaccttaga   3377

atgtgagctc catgagagca ggtaccttgt ttgtcttcac tgctgtatct attcccaacg   3437

cctcatgaca gtgcctggca catagtaggc actcaataaa tacttgttga atgaatgaaa   3497

aaaaaaaaaa a                                                        3508
```

<210> SEQ ID NO 28
<211> LENGTH: 692
<212> TYPE: PRT
<213> ORGANISM: Mus musculus

<400> SEQUENCE: 28

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300
```

```
Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690
```

<210> SEQ ID NO 29
<211> LENGTH: 2109

<212> TYPE: DNA
<213> ORGANISM: Gallus gallus
<220> FEATURE:
<221> NAME/KEY: CDS
<222> LOCATION: (1)..(2109)

<400> SEQUENCE: 29 atg ccc tcg gct acc aac ggc acc atg gcg agc agc agc ggg aag gcg 48
Met Pro Ser Ala Thr Asn Gly Thr Met Ala Ser Ser Ser Gly Lys Ala
1 5 10 15 ggc ccg ggc ggc aac gag cag gcc ccg gcg gcg gca gcg gcg gcc ccg 96
Gly Pro Gly Gly Asn Glu Gln Ala Pro Ala Ala Ala Ala Ala Ala Pro
20 25 30 cag gcg tcg ggc ggc agc atc acc tcg gtt cag acc gag gcc atg aag 144
Gln Ala Ser Gly Gly Ser Ile Thr Ser Val Gln Thr Glu Ala Met Lys
35 40 45 cag atc ttg gga gtg atc gac aaa aag ctc cgc aac ctc gag aag aaa 192
Gln Ile Leu Gly Val Ile Asp Lys Lys Leu Arg Asn Leu Glu Lys Lys
50 55 60 aag agc aaa ctt gac gat tac cag gaa cga atg aac aag ggg gaa cgt 240
Lys Ser Lys Leu Asp Asp Tyr Gln Glu Arg Met Asn Lys Gly Glu Arg
65 70 75 80 cta aat caa gat caa ctg gat gca gtg tca aaa tac cag gaa gtg aca 288
Leu Asn Gln Asp Gln Leu Asp Ala Val Ser Lys Tyr Gln Glu Val Thr
85 90 95 aat aac ctg gaa ttc gct aaa gaa ctg cag agg agc ttt atg gca ctg 336
Asn Asn Leu Glu Phe Ala Lys Glu Leu Gln Arg Ser Phe Met Ala Leu
100 105 110 agc caa gat atc cag aaa aca ata aaa aag acg gct cgc agg gag cag 384
Ser Gln Asp Ile Gln Lys Thr Ile Lys Lys Thr Ala Arg Arg Glu Gln
115 120 125 ctg atg aga gaa gag gct gag cag aag cgt tta aag act gtg cta gag 432
Leu Met Arg Glu Glu Ala Glu Gln Lys Arg Leu Lys Thr Val Leu Glu
130 135 140 ctg cag ttc att ttg gac aag ttg ggt gac gat gaa gtg cgc agt gac 480
Leu Gln Phe Ile Leu Asp Lys Leu Gly Asp Asp Glu Val Arg Ser Asp
145 150 155 160 ttg aaa caa gga tca aat gga gta ccg gta ctg aca gag gag gaa ctg 528
Leu Lys Gln Gly Ser Asn Gly Val Pro Val Leu Thr Glu Glu Glu Leu
165 170 175 aca atg ctg gat gaa ttt tac aag cta gtt tac cct gaa agg gac atg 576
Thr Met Leu Asp Glu Phe Tyr Lys Leu Val Tyr Pro Glu Arg Asp Met
180 185 190 aac atg agg ttg aat gag cag tat gag caa gca tct gtt cac ctg tgg 624
Asn Met Arg Leu Asn Glu Gln Tyr Glu Gln Ala Ser Val His Leu Trp
195 200 205 gac tta ctg gaa ggg aag gaa aaa ccc gtt tgt gga aca acc tat aaa 672
Asp Leu Leu Glu Gly Lys Glu Lys Pro Val Cys Gly Thr Thr Tyr Lys
210 215 220 gcc ctg aag gag gtt gtt gaa cgt att ctt caa act agt tac ttt gat 720
Ala Leu Lys Glu Val Val Glu Arg Ile Leu Gln Thr Ser Tyr Phe Asp
225 230 235 240 agc acc cat aac cat cag aac ggg tta tgt gag gaa gaa gag gca gca 768
Ser Thr His Asn His Gln Asn Gly Leu Cys Glu Glu Glu Glu Ala Ala
245 250 255 ccc aca cct gca gta gaa gac act gta gca gaa gct gag cct gat cca 816
Pro Thr Pro Ala Val Glu Asp Thr Val Ala Glu Ala Glu Pro Asp Pro
260 265 270 gca gaa gaa ttt act gaa cct act gaa gtt gaa tcg act gag tat gta 864
Ala Glu Glu Phe Thr Glu Pro Thr Glu Val Glu Ser Thr Glu Tyr Val
275 280 285

-continued

```
aac aga caa ttc atg gca gag act cag ttc agc agt agt gag aag gaa      912
Asn Arg Gln Phe Met Ala Glu Thr Gln Phe Ser Ser Ser Glu Lys Glu
    290                 295                 300

cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320

cag caa caa aca caa gct aca tct cct cca gtt cct gaa cct cat aca     1008
Gln Gln Gln Thr Gln Ala Thr Ser Pro Pro Val Pro Glu Pro His Thr
                325                 330                 335

ctc act act gtg gct caa gca gat cct ctt gtt aga aga cag aga gta     1056
Leu Thr Thr Val Ala Gln Ala Asp Pro Leu Val Arg Arg Gln Arg Val
            340                 345                 350

cag gac ctt atg gcc cag atg cag ggt cca tat aac ttc atg cag gac     1104
Gln Asp Leu Met Ala Gln Met Gln Gly Pro Tyr Asn Phe Met Gln Asp
        355                 360                 365

tct atg ctg gag ttt gag aac cag aca ctt gat cct gcc att gta tct     1152
Ser Met Leu Glu Phe Glu Asn Gln Thr Leu Asp Pro Ala Ile Val Ser
    370                 375                 380

gca cag ccc atg aat cca gca cag aat ttg gac atg ccg caa atg gtc     1200
Ala Gln Pro Met Asn Pro Ala Gln Asn Leu Asp Met Pro Gln Met Val
385                 390                 395                 400

tgc cct cca gtt cat act gag tca aga ctt gcc cag cct aat caa gtt     1248
Cys Pro Pro Val His Thr Glu Ser Arg Leu Ala Gln Pro Asn Gln Val
                405                 410                 415

cct gtg caa cca gaa gct acg cag gtt ccc ttg gtt tca tct aca agt     1296
Pro Val Gln Pro Glu Ala Thr Gln Val Pro Leu Val Ser Ser Thr Ser
            420                 425                 430

gag gga tat aca gcc tcc cag ccc atg tat cag cct tct cat acc aca     1344
Glu Gly Tyr Thr Ala Ser Gln Pro Met Tyr Gln Pro Ser His Thr Thr
        435                 440                 445

gag caa cgg cca cag aag gaa tcc att gac cag att cag gct tca atg     1392
Glu Gln Arg Pro Gln Lys Glu Ser Ile Asp Gln Ile Gln Ala Ser Met
    450                 455                 460

tca ctg aat gca gac cag acc ccg tca tca tca tca ctt ccc act gca     1440
Ser Leu Asn Ala Asp Gln Thr Pro Ser Ser Ser Ser Leu Pro Thr Ala
465                 470                 475                 480

tcc cag ccg caa gtt ttc caa gct gga tct agc aaa cct ttg cat agc     1488
Ser Gln Pro Gln Val Phe Gln Ala Gly Ser Ser Lys Pro Leu His Ser
                485                 490                 495

agc gga atc aat gtt aat gca gct cca ttc caa tcc atg caa aca gta     1536
Ser Gly Ile Asn Val Asn Ala Ala Pro Phe Gln Ser Met Gln Thr Val
            500                 505                 510

ttc aac atg aat gca cct gtt cct cct gtt aat gag cca gaa gcc ctt     1584
Phe Asn Met Asn Ala Pro Val Pro Pro Val Asn Glu Pro Glu Ala Leu
        515                 520                 525

aag caa caa aat cag tac cag gcc agt tac aac cag agt ttc tcc aat     1632
Lys Gln Gln Asn Gln Tyr Gln Ala Ser Tyr Asn Gln Ser Phe Ser Asn
    530                 535                 540

cag cca cac caa gta gaa caa tca gat ctt cag caa gaa cag ctc cag     1680
Gln Pro His Gln Val Glu Gln Ser Asp Leu Gln Gln Glu Gln Leu Gln
545                 550                 555                 560

aca gtg gtt ggt act tac cat ggt tct ccg gac cag acc cat caa gtg     1728
Thr Val Val Gly Thr Tyr His Gly Ser Pro Asp Gln Thr His Gln Val
                565                 570                 575

gca gga aac cac cag caa cct ccc cag cag aat act gga ttt cca cgc     1776
Ala Gly Asn His Gln Gln Pro Pro Gln Gln Asn Thr Gly Phe Pro Arg
            580                 585                 590

aac agt cag cct tat tac aac agt cgg gga gtg tct cgt ggt gga tca     1824
Asn Ser Gln Pro Tyr Tyr Asn Ser Arg Gly Val Ser Arg Gly Gly Ser
```

```
        595                 600                 605

cgt ggg act cgt gga ttg atg aat ggt tac agg gga cct gca aat gga     1872
Arg Gly Thr Arg Gly Leu Met Asn Gly Tyr Arg Gly Pro Ala Asn Gly
    610                 615                 620

ttt aga gga gga tat gat ggc tac cgt cct tca ttt tcc aac act ccg     1920
Phe Arg Gly Gly Tyr Asp Gly Tyr Arg Pro Ser Phe Ser Asn Thr Pro
625                 630                 635                 640

aac agt ggt tac acg cag ccc caa ttt aat gct cct cga gat tat tca     1968
Asn Ser Gly Tyr Thr Gln Pro Gln Phe Asn Ala Pro Arg Asp Tyr Ser
                645                 650                 655

aac tac cag cgg gat gga tat cag cag aac ttc aaa cgt ggt tct gga     2016
Asn Tyr Gln Arg Asp Gly Tyr Gln Gln Asn Phe Lys Arg Gly Ser Gly
            660                 665                 670

caa agt ggg cct cgg gga gct cct cga ggt cgt gga ggg ccc cca aga     2064
Gln Ser Gly Pro Arg Gly Ala Pro Arg Gly Arg Gly Gly Pro Pro Arg
        675                 680                 685

cca aac aga ggg atg cct caa atg aac gct cag caa gtg aat taa         2109
Pro Asn Arg Gly Met Pro Gln Met Asn Ala Gln Gln Val Asn
    690                 695                 700


<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240
```

-continued

```
Ser Thr His Asn His Gln Asn Gly Leu Cys Glu Glu Glu Glu Ala Ala
            245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
    290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
            325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
            405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Ser Leu Pro Thr Ala
465                 470                 475                 480

Ser Gln Pro Gln Val Phe Gln Ala Gly Ser Ser Lys Pro Leu His Ser
            485                 490                 495

Ser Gly Ile Asn Val Asn Ala Ala Pro Phe Gln Ser Met Gln Thr Val
            500                 505                 510

Phe Asn Met Asn Ala Pro Val Pro Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
            565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605

Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
            645                 650                 655

Asn Tyr Gln Arg Asp Gly Tyr Gln Gln Asn Phe Lys Arg Gly Ser Gly
```

```
        660                 665                 670

Gln Ser Gly Pro Arg Gly Ala Pro Arg Gly Arg Gly Gly Pro Pro Arg
        675                 680                 685

Pro Asn Arg Gly Met Pro Gln Met Asn Ala Gln Gln Val Asn
    690                 695                 700


<210> SEQ ID NO 31
<211> LENGTH: 20
<212> TYPE: DNA
<213> ORGANISM: Artificial Sequence
<220> FEATURE:
<223> OTHER INFORMATION: Synthetic T3 primer

<400> SEQUENCE: 31

aattaaccct cactaaaggg                                                20


<210> SEQ ID NO 32
<211> LENGTH: 19
<212> TYPE: DNA
<213> ORGANISM: Artificial Sequence
<220> FEATURE:
<223> OTHER INFORMATION: Synthetic T7 primer

<400> SEQUENCE: 32

taatacgact cactatagg                                                 19


<210> SEQ ID NO 33
<211> LENGTH: 18
<212> TYPE: DNA
<213> ORGANISM: Artificial Sequence
<220> FEATURE:
<223> OTHER INFORMATION: Synthetic primer

<400> SEQUENCE: 33

aaggtttgaa tggagtgc                                                  18


<210> SEQ ID NO 34
<211> LENGTH: 18
<212> TYPE: DNA
<213> ORGANISM: Artificial Sequence
<220> FEATURE:
<223> OTHER INFORMATION: Synthetic primer

<400> SEQUENCE: 34

tgctcctttt caccactg                                                  18


<210> SEQ ID NO 35
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 35

gggctgcttt taactctg                                                  18


<210> SEQ ID NO 36
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 36

ccaggaaatg agcttgac                                                  18
```

<210> SEQ ID NO 37
<211> LENGTH: 14
<212> TYPE: PRT
<213> ORGANISM: Artificial Sequence
<220> FEATURE:
<223> OTHER INFORMATION: Synthetic peptide

<400> SEQUENCE: 37

Arg Asn Leu Glu Lys Lys Lys Gly Lys Leu Asp Asp Tyr Gln
1 5 10

<210> SEQ ID NO 38
<211> LENGTH: 22
<212> TYPE: DNA
<213> ORGANISM: Artificial Sequence
<220> FEATURE:
<223> OTHER INFORMATION: Synthetic primer

<400> SEQUENCE: 38
aggtsharct gcagsagtcw gg 22

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
ctcgagttaa ttcacttgct gag 23

<210> SEQ ID NO 40
<211> LENGTH: 5
<212> TYPE: PRT
<213> ORGANISM: Mus musculus

<400> SEQUENCE: 40

Asp Tyr Asn Met Asp
1 5

<210> SEQ ID NO 41
<211> LENGTH: 17
<212> TYPE: PRT
<213> ORGANISM: Mus musculus

<400> SEQUENCE: 41

Asp Ile Asn Pro Asn Tyr Asp Ser Thr Ser Tyr Asn Gln Lys Phe Lys
1 5 10 15

Gly

<210> SEQ ID NO 42
<211> LENGTH: 11
<212> TYPE: PRT
<213> ORGANISM: Mus musculus

<400> SEQUENCE: 42

Ser Arg Ser Tyr Asp Tyr Glu Gly Phe Ala Tyr
1 5 10

<210> SEQ ID NO 43
<211> LENGTH: 148
<212> TYPE: PRT
<213> ORGANISM: Mus musculus

<400> SEQUENCE: 43

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 44
<211> LENGTH: 11
<212> TYPE: PRT
<213> ORGANISM: Mus musculus

<400> SEQUENCE: 44

Arg Ala Ser Gly Asn Ile His Asn Tyr Leu Ala
1               5                   10

<210> SEQ ID NO 45
<211> LENGTH: 7
<212> TYPE: PRT
<213> ORGANISM: Mus musculus

<400> SEQUENCE: 45

Asn Ala Lys Thr Leu Ala Asp
1               5

<210> SEQ ID NO 46
<211> LENGTH: 8
<212> TYPE: PRT
<213> ORGANISM: Mus musculus

<400> SEQUENCE: 46

Gln His Phe Trp Ser Thr Leu Thr
1               5

<210> SEQ ID NO 47
<211> LENGTH: 139
<212> TYPE: PRT
<213> ORGANISM: Mus musculus

<400> SEQUENCE: 47

Met Ser Val Leu Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

```
Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Leu Thr Phe Gly Ala Gly Thr Lys Leu Glu Leu Lys Arg Ala
        115                 120                 125

Asp Ala Ala Pro Thr Val Ser Asn Pro Tyr Asp
    130                 135
```

<210> SEQ ID NO 48
<211> LENGTH: 444
<212> TYPE: DNA
<213> ORGANISM: Mus musculus

<400> SEQUENCE: 48

```
atggaatgga gcggggtctt tatctttctc ctgtcaggaa ctgcaggtgt cctctctgag     60

gtccagctgc atcagtttgg agctgagctg gtgaagcctg gggcttcagt gaagatatcc    120

tgcaaggctt ctggctacac attcactgac tacaacatgg actgggtgaa gcagagccat    180

ggaaagagcc ttgagtggat tggagatatt aatcctaact atgatagtac tagctacaac    240

cagaagttca agggaaaggc cacattgact gtagacaagt cctccagcac agcctacatg    300

gagctccgca gcctgacatc tgaggacact gcagtctatt actgtgcaag atcgaggagc    360

tatgattacg aaggatttgc ttactggggc caagggactc tggtcactgt ctctgcagcc    420

aaaacaacac ccccatcagt ctat                                           444
```

<210> SEQ ID NO 49
<211> LENGTH: 444
<212> TYPE: DNA
<213> ORGANISM: Mus musculus

<400> SEQUENCE: 49

```
atggaatgga gcggggtctt tatctttctc ctgtcaggaa ctgcaggtgt cctctctgag     60

gtccagctgc atcagtttgg agctgagctg gtgaagcctg gggcttcagt gaagatatcc    120

tgcaaggctt ctggctacac attcactgac tacaacatgg actgggtgaa gcagagccat    180

ggaaagagcc ttgagtggat tggagatatt aatcctaact atgatagtac tagctacaac    240

cagaagttca agggaaaggc cacattgact gtagacaagt cctccagcac agcctacatg    300

gagctccgca gcctgacatc tgaggacact gcagtctatt actgtgcaag atcgaggagc    360

tatgattacg aaggatttgc ttactggggc caagggactc tggtcactgt ctctgcagcc    420

aaaacaacac ccccatcagt ctat                                           444
```

<210> SEQ ID NO 50
<211> LENGTH: 11
<212> TYPE: PRT
<213> ORGANISM: Mus musculus

<400> SEQUENCE: 50

```
Leu Trp Ser Val Asn Gln Lys Asn Tyr Leu Ser
1               5                   10
```

<210> SEQ ID NO 51
<211> LENGTH: 7
<212> TYPE: PRT
<213> ORGANISM: Mus musculus

<400> SEQUENCE: 51

```
Gly Ala Ser Ile Arg Glu Ser
1               5
```

<210> SEQ ID NO 52
<211> LENGTH: 9
<212> TYPE: PRT
<213> ORGANISM: Mus musculus

<400> SEQUENCE: 52

```
Gln His Asn His Gly Ser Phe Leu Pro
1               5
```

<210> SEQ ID NO 53
<211> LENGTH: 132
<212> TYPE: PRT
<213> ORGANISM: Mus musculus

<400> SEQUENCE: 53

```
Ala Val Leu Arg Cys Ser Arg Gly Leu Leu Val Ile Trp Ile Ser Asp
1               5                   10                  15

Ile Gln Leu Thr Gln Ser Pro Ser Ser Leu Ala Val Thr Ala Gly Glu
            20                  25                  30

Lys Val Thr Met Ser Cys Lys Ser Ser Gln Ser Leu Leu Trp Ser Val
        35                  40                  45

Asn Gln Lys Asn Tyr Leu Ser Trp Tyr Gln Gln Lys Gln Arg Gln Pro
    50                  55                  60

Pro Lys Leu Leu Ile Tyr Gly Ala Ser Ile Arg Glu Ser Trp Val Pro
65                  70                  75                  80

Asp Arg Phe Thr Gly Ser Gly Ser Gly Thr Asp Phe Thr Leu Thr Ile
                85                  90                  95

Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
    130
```

<210> SEQ ID NO 54
<211> LENGTH: 398
<212> TYPE: DNA
<213> ORGANISM: Mus musculus

<400> SEQUENCE: 54

```
gcggtcctgc ggtgctctag aggactacta gtcatatgga tttccgatat ccagctgacc     60

cagtctccat cctccctggc tgtgacagca ggagagaagg tcactatgag ctgcaagtcc    120

agtcagagtc ttttgtggag tgtaaaccag aagaactact tgtcctggta ccagcagaaa    180

caaaggcagc ctcctaaact gcttatctat ggggcatcca ttagagaatc ttgggtccct    240

gatcggttca caggaagtgg atctgggaca gacttcactc tcaccattag caatgtgcat    300

gctgaagacc tagcagttta ttactgtcaa cacaatcatg gcagctttct cccctcacgt    360

tcggagcagg taccaagctg gagatcaaac aatcggat                            398
```

<210> SEQ ID NO 55
<211> LENGTH: 11
<212> TYPE: PRT
<213> ORGANISM: Mus musculus

<400> SEQUENCE: 55

Arg Ala Ser Gly Asn Ile His Asn Tyr Leu Ala
1 5 10

<210> SEQ ID NO 56
<211> LENGTH: 7
<212> TYPE: PRT
<213> ORGANISM: Mus musculus

<400> SEQUENCE: 56

Asn Ala Lys Thr Leu Ala Asp
1 5

<210> SEQ ID NO 57
<211> LENGTH: 9
<212> TYPE: PRT
<213> ORGANISM: Mus musculus

<400> SEQUENCE: 57

Gln His Phe Trp Ser Thr Leu Thr Phe
1 5

<210> SEQ ID NO 58
<211> LENGTH: 117
<212> TYPE: PRT
<213> ORGANISM: Mus musculus

<400> SEQUENCE: 58

Arg Thr Thr Ser His Met Asp Ser Asp Ile Gln Leu Thr Gln Ser Pro
1 5 10 15

Ala Ser Leu Ser Ala Ser Val Gly Glu Thr Val Thr Ile Thr Cys Arg
20 25 30

Ala Ser Gly Asn Ile His Asn Tyr Leu Ala Trp Tyr Gln Gln Lys Gln
35 40 45

Gly Lys Ser Pro Gln Leu Leu Val Tyr Asn Ala Lys Thr Leu Ala Asp
50 55 60

Gly Val Pro Ser Arg Phe Ser Gly Ser Gly Ser Gly Thr Gln Tyr Ser
65 70 75 80

Leu Lys Ile Asn Ser Leu Gln Pro Glu Asp Phe Gly Ser Tyr Tyr Cys
85 90 95

Gln His Phe Trp Ser Thr Leu Thr Phe Gly Gly Gly Thr Lys Leu Glu
100 105 110

Ile Lys Gln Ser Asp
115

<210> SEQ ID NO 59
<211> LENGTH: 353
<212> TYPE: DNA
<213> ORGANISM: Mus musculus

<400> SEQUENCE: 59
gaggactact agtcatatgg attccgatat ccagctgacc cagtctccag cctccctatc 60
tgcatctgtg ggagaaactg tcaccatcac atgtcgagca agtgggaata ttcacaatta 120
tttagcatgg tatcagcaga aacagggaaa atctcctcag ctcctggtct ataatgcaaa 180
aaccttagca gatggtgtgc catcaaggtt cagtggcagt ggatcaggaa cacaatattc 240
tctcaagatc aacagcctgc agcctgaaga ttttgggagt tattactgtc aacatttttg 300
gagtacgctc acgttcggag gtggtaccaa gctggagatc aaacaatcgg atc 353

<210> SEQ ID NO 60
<211> LENGTH: 11
<212> TYPE: PRT
<213> ORGANISM: Mus musculus

<400> SEQUENCE: 60

Arg Ala Ser Gln Ser Ile Ser Asn Tyr Leu His
1 5 10

<210> SEQ ID NO 61
<211> LENGTH: 7
<212> TYPE: PRT
<213> ORGANISM: Mus musculus

<400> SEQUENCE: 61

Tyr Ala Ser Gln Ser Ile Ser
1 5

<210> SEQ ID NO 62
<211> LENGTH: 9
<212> TYPE: PRT
<213> ORGANISM: Mus musculus

<400> SEQUENCE: 62

Gln Gln Ser Asn Ser Trp Pro Tyr Thr
1 5

<210> SEQ ID NO 63
<211> LENGTH: 94
<212> TYPE: PRT
<213> ORGANISM: Mus musculus

<400> SEQUENCE: 63

Ser Gly Asp Arg Val Ser Leu Ser Cys Arg Ala Ser Gln Ser Ile Ser
1 5 10 15

Asn Tyr Leu His Trp Tyr Gln Gln Lys Ser His Glu Ser Pro Arg Leu
20 25 30

Leu Ile Lys Tyr Ala Ser Gln Ser Ile Ser Gly Ile Pro Ser Arg Phe
35 40 45

Ser Gly Ser Gly Ser Gly Thr Asp Phe Thr Leu Ser Ile Asn Ser Val
50 55 60

Glu Thr Glu Asp Phe Gly Met Tyr Phe Cys Gln Gln Ser Asn Ser Trp
65 70 75 80

Pro Tyr Thr Phe Gly Ala Gly Thr Lys Leu Glu Ile Lys Gln
85 90

<210> SEQ ID NO 64
<211> LENGTH: 283
<212> TYPE: DNA
<213> ORGANISM: Mus musculus

<400> SEQUENCE: 64
tcaggagata gagtcagtct ttcctgcagg gccagtcaaa gtattagcaa ctacctacac 60
tggtatcaac aaaaatcaca tgagtctcca aggcttctca tcaagtatgc ttcccagtcc 120
atctctggga tcccctccag gttcagtggc agtggatcag ggacagattt cactctcagt 180
atcaacagtg tggagactga agattttgga atgtatttct gtcaacagag taacagctgg 240
ccgtacacgt tcggtgcagg taccaagctg gagatcaaac aga 283

<210> SEQ ID NO 65
<211> LENGTH: 11
<212> TYPE: PRT
<213> ORGANISM: Mus musculus

<400> SEQUENCE: 65

Leu Ser Ile Val Asn Arg Tyr His Tyr Met Ser
1               5                   10

<210> SEQ ID NO 66
<211> LENGTH: 6
<212> TYPE: PRT
<213> ORGANISM: Mus musculus

<400> SEQUENCE: 66

Glu Ala Ser Ile Thr Lys
1               5

<210> SEQ ID NO 67
<211> LENGTH: 9
<212> TYPE: PRT
<213> ORGANISM: Mus musculus

<400> SEQUENCE: 67

Gln His Asn Arg Gly Ser Phe Leu Pro
1               5

<210> SEQ ID NO 68
<211> LENGTH: 105
<212> TYPE: PRT
<213> ORGANISM: Mus musculus

<400> SEQUENCE: 68

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Arg Ser Asn
            100                 105

<210> SEQ ID NO 69
<211> LENGTH: 317
<212> TYPE: DNA
<213> ORGANISM: Mus musculus

<400> SEQUENCE: 69
ggactcttct gctctgtgga gagatgtcac tatcaactgc aatccagtca gaatcttttg 60
agtattgtaa accggtatca ctacatgtcc ggaaaccctc ctaaactcct ggtctatcct 120

```
gcactgctta tctatgaggc atccattaca aaatcctgtg tccctgatcg gttcacacga    180

agtggatctg ggacaaactt cactctcacc attaattttg tgcatgctga tgacctaatt    240

ttttattact gtcaacacaa tcgtggcagc tttctcccct caagttcggt gcaggtacca    300

agaaggagat caaacaa                                                   317
```

```
<210> SEQ ID NO 70
<211> LENGTH: 5
<212> TYPE: PRT
<213> ORGANISM: Mus musculus

<400> SEQUENCE: 70

Gly Tyr Thr Met Asn
1               5


<210> SEQ ID NO 71
<211> LENGTH: 16
<212> TYPE: PRT
<213> ORGANISM: Mus musculus

<400> SEQUENCE: 71

Asn Pro Tyr Asn Gly Gly Thr Ser Tyr Asn Gln Lys Phe Lys Gly Lys
1               5                   10                  15


<210> SEQ ID NO 72
<211> LENGTH: 9
<212> TYPE: PRT
<213> ORGANISM: Mus musculus

<400> SEQUENCE: 72

Trp Gly Val Trp Ser Ala Met Asp Tyr
1               5


<210> SEQ ID NO 73
<211> LENGTH: 100
<212> TYPE: PRT
<213> ORGANISM: Mus musculus

<400> SEQUENCE: 73

Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100


<210> SEQ ID NO 74
<211> LENGTH: 11
<212> TYPE: PRT
<213> ORGANISM: Mus musculus

<400> SEQUENCE: 74

Lys Ala Ser Gln Asn Val Arg Thr Ala Val Ala
```

1 5 10

<210> SEQ ID NO 75
<211> LENGTH: 7
<212> TYPE: PRT
<213> ORGANISM: Mus musculus

<400> SEQUENCE: 75

Leu Ala Ser Asn Arg Asp Thr
1 5

<210> SEQ ID NO 76
<211> LENGTH: 9
<212> TYPE: PRT
<213> ORGANISM: Mus musculus

<400> SEQUENCE: 76

Leu Gln His Cys Asn Tyr Pro Asn Glu
1 5

<210> SEQ ID NO 77
<211> LENGTH: 90
<212> TYPE: PRT
<213> ORGANISM: Mus musculus

<400> SEQUENCE: 77

Asp Arg Val Ser Ile Thr Cys Lys Ala Ser Gln Asn Val Arg Thr Ala
1 5 10 15

Val Ala Trp Tyr Gln Gln Lys Pro Arg Gln Ser Pro Lys Ala Leu Ile
20 25 30

Tyr Leu Ala Ser Asn Arg Asp Thr Gly Leu Pro Asp Arg Phe Pro Gly
35 40 45

Arg Gly Ser Gly Thr Asp Phe Thr Leu Asn Ile Thr Asn Val Gln Ser
50 55 60

Glu Asp Leu Glu Asp Tyr Phe Cys Leu Gln His Cys Asn Tyr Pro Asn
65 70 75 80

Glu Phe Arg Gly Cys Thr Lys Val Pro Ile
85 90

<210> SEQ ID NO 78
<211> LENGTH: 301
<212> TYPE: DNA
<213> ORGANISM: Mus musculus

<400> SEQUENCE: 78
gatatcctgc aggcttctgg ttactcattc actggctaca ccatgaactg ggtgaagcag 60
agccatggaa agaaccttga gtggattgga cttattaatc cttacaatgg tggtactagc 120
tacaaccaga agttcaaggg caaggccaca ttaactgtag acaagtcatc cagcacagcc 180
tacatggagc tcctcagtct gacatctgag gactctgcag tctattactg tgcaagatgg 240
ggggtatggt cggctatgga ctactggggc caagggacca cggtcaccgt ctcctcaaaa 300
a 301

<210> SEQ ID NO 79
<211> LENGTH: 290
<212> TYPE: DNA
<213> ORGANISM: Mus musculus

<400> SEQUENCE: 79
gacagggtca gcatcacctg caaggccagt caaaatgttc gtactgctgt agcctggtat 60

```
caacagaaac cacggcagtc tcctaaagca ctgatttact tggcatccaa ccgggacact    120

ggactccctg atcgcttccc aggcagggga tctgggacag atttcactct caacattacc    180

aatgtgcaat ctgaagacct ggaagattat ttctgtctgc aacattgtaa ttatcctaac    240

gagttcagag gttgtaccaa ggtgccaatc taaagaacaa acaccccctg               290


<210> SEQ ID NO 80
<211> LENGTH: 5
<212> TYPE: PRT
<213> ORGANISM: Mus musculus

<400> SEQUENCE: 80

Ser Tyr Trp Met Gln
1               5


<210> SEQ ID NO 81
<211> LENGTH: 17
<212> TYPE: PRT
<213> ORGANISM: Mus musculus

<400> SEQUENCE: 81

Ala Ile Tyr Pro Gly Asp Gly Asp Thr Arg Tyr Thr Gln Lys Phe Lys
1               5                   10                  15

Gly


<210> SEQ ID NO 82
<211> LENGTH: 11
<212> TYPE: PRT
<213> ORGANISM: Mus musculus

<400> SEQUENCE: 82

Ala Arg Gly Glu Tyr Gly Asn Tyr Phe Ala Tyr
1               5                   10


<210> SEQ ID NO 83
<211> LENGTH: 116
<212> TYPE: PRT
<213> ORGANISM: Mus musculus

<400> SEQUENCE: 83

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
        35                  40                  45

Tyr Pro Gly Asp Gly Asp Thr Arg Tyr Thr Gln Lys Phe Lys Gly Lys
    50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115


<210> SEQ ID NO 84
<211> LENGTH: 11
```

<212> TYPE: PRT
<213> ORGANISM: Mus musculus

<400> SEQUENCE: 84

```
Lys Ala Ser Gln Asp Ile Asn Ser Tyr Leu Ser
1               5                   10
```

<210> SEQ ID NO 85
<211> LENGTH: 7
<212> TYPE: PRT
<213> ORGANISM: Mus musculus

<400> SEQUENCE: 85

```
Arg Ala Asn Arg Leu Val Asp
1               5
```

<210> SEQ ID NO 86
<211> LENGTH: 9
<212> TYPE: PRT
<213> ORGANISM: Mus musculus

<400> SEQUENCE: 86

```
Leu Gln Tyr Asp Glu Phe Pro Leu Thr
1               5
```

<210> SEQ ID NO 87
<211> LENGTH: 100
<212> TYPE: PRT
<213> ORGANISM: Mus musculus

<400> SEQUENCE: 87

```
Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45

Val Pro Ser Arg Phe Ser Gly Ser Gly Ser Gly Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
            100
```

<210> SEQ ID NO 88
<211> LENGTH: 352
<212> TYPE: DNA
<213> ORGANISM: Mus musculus

<400> SEQUENCE: 88

```
aactgcagga gtctggggct gagctggcaa gacctggggc ttcagtgaag ttgtcctgca      60

aggcttctgg ctacaccttt actagctact ggatgcagtg ggtaaaacag aggcctggac     120

agggtctgga atggattggg gctatttatc ctggagatgg tgatactagg tacactcaga     180

agttcaaggg caaggccaca ttgactgcag ataaatcctc cagcacagcc tacatgcaac     240

tcagcagctt ggcatctgag gactctgcgg tctattactg tgcaagaggg gagtatggta     300

actattttgc ttactggggc caagggacca cggtcaccgt ctcctcaaat cg             352
```

<210> SEQ ID NO 89
<211> LENGTH: 302
<212> TYPE: DNA
<213> ORGANISM: Mus musculus

<400> SEQUENCE: 89
ggacatcgga tgcatctcta ggagagagag tcactatcac ttgcaaggcg agtcaggaca 60
ttaatagcta tttaagctgg ttccagcaga aaccagggaa atctcctaag accctgatct 120
atcgtgcaaa cagattggta gatggggtcc catcaaggtt cagtggcagt ggatctgggc 180
aagattattc tctcaccatc agcagcctgg agtatgaaga tatgggaatt tattattgtc 240
tacagtatga tgagtttccg ctcacgttcg gaggaggtac caagctggag atcaaacaaa 300
aa 302

<210> SEQ ID NO 90
<211> LENGTH: 5
<212> TYPE: PRT
<213> ORGANISM: Mus musculus

<400> SEQUENCE: 90

Asp Thr Tyr Met His
1 5

<210> SEQ ID NO 91
<211> LENGTH: 17
<212> TYPE: PRT
<213> ORGANISM: Mus musculus

<400> SEQUENCE: 91

Arg Ile Asp Pro Ala Asn Gly Asn Thr Lys Tyr Asp Pro Lys Phe Gln
1 5 10 15

Gly

<210> SEQ ID NO 92
<211> LENGTH: 14
<212> TYPE: PRT
<213> ORGANISM: Mus musculus

<400> SEQUENCE: 92

Ala Arg Pro Ile His Tyr Tyr Tyr Gly Ser Ser Leu Ala Tyr
1 5 10

<210> SEQ ID NO 93
<211> LENGTH: 108
<212> TYPE: PRT
<213> ORGANISM: Mus musculus

<400> SEQUENCE: 93

Ala Trp Leu Ser Gln Leu Ser Cys Thr Ala Ser Gly Phe Asn Ile Lys
1 5 10 15

Asp Thr Tyr Met His Trp Val Lys Gln Arg Pro Glu Gln Gly Leu Glu
20 25 30

Trp Ile Gly Arg Ile Asp Pro Ala Asn Gly Asn Thr Lys Tyr Asp Pro
35 40 45

Lys Phe Gln Gly Lys Ala Thr Ile Thr Ala Asp Thr Ser Ser Asn Thr
50 55 60

Ala Tyr Leu Gln Leu Ser Ser Leu Thr Ser Glu Asp Thr Ala Val Tyr
65 70 75 80

Tyr Cys Ala Arg Pro Ile His Tyr Tyr Tyr Gly Ser Ser Leu Ala Tyr

```
                85                  90                  95

Trp Gly Gln Gly Thr Thr Val Thr Val Ser Ser Lys
            100                 105


<210> SEQ ID NO 94
<211> LENGTH: 11
<212> TYPE: PRT
<213> ORGANISM: Mus musculus

<400> SEQUENCE: 94

Ser Val Asp Ser Tyr Gly Asn Ser Phe Met His
1               5                   10


<210> SEQ ID NO 95
<211> LENGTH: 7
<212> TYPE: PRT
<213> ORGANISM: Mus musculus

<400> SEQUENCE: 95

Arg Ala Ser Asn Leu Glu Ser
1               5


<210> SEQ ID NO 96
<211> LENGTH: 9
<212> TYPE: PRT
<213> ORGANISM: Mus musculus

<400> SEQUENCE: 96

Gln Gln Ser Asn Glu Asp Pro Gly Arg
1               5


<210> SEQ ID NO 97
<211> LENGTH: 104
<212> TYPE: PRT
<213> ORGANISM: Mus musculus

<400> SEQUENCE: 97

Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100


<210> SEQ ID NO 98
<211> LENGTH: 326
<212> TYPE: DNA
<213> ORGANISM: Mus musculus

<400> SEQUENCE: 98

gcatggctca gtcagttgtc ctgcacagct tctggcttca acattaaaga cacctatatg      60

cactgggtga agcagaggcc tgaacagggc ctggagtgga ttggaaggat tgatcctgcg     120
```

aatggtaata ctaaatatga cccgaagttc cagggcaagg ccactataac agcagacaca 180
tcctccaaca cagcctacct gcagctcagc agcctgacat ctgaggacac tgccgtctat 240
tactgtgcta gaccgattca ttattactac ggtagtagcc ttgcttactg gggccaaggg 300
accacggtca ccgtctcctc aaaaaa 326

<210> SEQ ID NO 99
<211> LENGTH: 313
<212> TYPE: DNA
<213> ORGANISM: Mus musculus

<400> SEQUENCE: 99
gagtttcatg ctgtgtctct agggcagagg gccaccatat cctgcagagc cagtgaaagt 60
gttgatagtt atggcaatag ttttatgcac tggtaccagc agaaaccagg acagccaccc 120
aaactcctca tctatcgtgc atccaaccta gaatctggga tccctgccag gttcagtggc 180
agtgggtcta ggacagactt caccctcacc attaatcctg tggaggctga tgatgttgca 240
acctattact gtcagcaaag taatgaggat cctggacgtt cggaggtggt accaagctgg 300
agatcaaaca aaa 313

<210> SEQ ID NO 100
<211> LENGTH: 5
<212> TYPE: PRT
<213> ORGANISM: Mus musculus

<400> SEQUENCE: 100

Asp Tyr Tyr Met Ser
1 5

<210> SEQ ID NO 101
<211> LENGTH: 17
<212> TYPE: PRT
<213> ORGANISM: Mus musculus

<400> SEQUENCE: 101

Arg Asn Lys Ala Asn Gly Tyr Thr Thr Glu Tyr Ser Ala Ser Val Lys
1 5 10 15

Gly

<210> SEQ ID NO 102
<211> LENGTH: 9
<212> TYPE: PRT
<213> ORGANISM: Mus musculus

<400> SEQUENCE: 102

Ala Arg Ala Asn Trp Ala Phe Asp Tyr
1 5

<210> SEQ ID NO 103
<211> LENGTH: 109
<212> TYPE: PRT
<213> ORGANISM: Mus musculus

<400> SEQUENCE: 103

Pro Arg Ala Ser Leu Gly Val Ser Glu Thr Leu Leu Cys Thr Ser Gly
1 5 10 15

Phe Thr Phe Thr Asp Tyr Tyr Met Ser Trp Val Arg Gln Pro Pro Gly
20 25 30

Lys Ala Leu Glu Trp Leu Gly Phe Ile Arg Asn Lys Ala Asn Gly Tyr
35 40 45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 104
<211> LENGTH: 11
<212> TYPE: PRT
<213> ORGANISM: Mus musculus

<400> SEQUENCE: 104

Arg Ala Ser Gln Ser Ile Ser Asn Tyr Leu His
1               5                   10

<210> SEQ ID NO 105
<211> LENGTH: 7
<212> TYPE: PRT
<213> ORGANISM: Mus musculus

<400> SEQUENCE: 105

Tyr Ala Ser Gln Ser Ile Ser
1               5

<210> SEQ ID NO 106
<211> LENGTH: 9
<212> TYPE: PRT
<213> ORGANISM: Mus musculus

<400> SEQUENCE: 106

Gln Gln Ser Asn Ser Trp Pro Tyr Thr
1               5

<210> SEQ ID NO 107
<211> LENGTH: 94
<212> TYPE: PRT
<213> ORGANISM: Mus musculus

<400> SEQUENCE: 107

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90

<210> SEQ ID NO 108
<211> LENGTH: 329
<212> TYPE: DNA
<213> ORGANISM: Mus musculus

<400> SEQUENCE: 108

```
ggccgcgtgc tagcctgggg gtctctgaga ctctcctgtg cacttctggg ttcaccttca     60

ctgattacta catgagctgg gtccgccagc ctccaggaaa ggcacttgag tggttgggtt    120

ttattagaaa caaagctaat ggttacacaa cagagtacag tgcatctgtg aagggtcggt    180

tcaccatctc cagagataat tcccaaagca tcctctatct tcaaatgaac accctgagag    240

ctgaggacag tgccacttat tactgtgcaa gggctaactg ggcctttgac tactggggcc    300

aagggaccac ggtcaccgtc tcctcaaaa                                      329
```

<210> SEQ ID NO 109
<211> LENGTH: 284
<212> TYPE: DNA
<213> ORGANISM: Mus musculus

<400> SEQUENCE: 109

```
tcaggagata gagtcagtct ttcctgcagg gccagtcaaa gtattagcaa ctacctacac     60

tggtatcaac aaaaatcaca tgagtctcca aggcttctca tcaagtatgc ttcccagtcc    120

atctctggga tcccctccag gttcagtggc agtggatcag ggacagattt cactctcagt    180

atcaacagtg tggagactga agattttgga atgtatttct gtcaacagag taacagctgg    240

ccgtacacgt tcggaggagg taccaagctg gagatcaaac agaa                     284
```

<210> SEQ ID NO 110
<211> LENGTH: 5
<212> TYPE: PRT
<213> ORGANISM: Mus musculus

<400> SEQUENCE: 110

```
Asp Tyr Tyr Met Ser
1               5
```

<210> SEQ ID NO 111
<211> LENGTH: 17
<212> TYPE: PRT
<213> ORGANISM: Mus musculus

<400> SEQUENCE: 111

```
Arg Asn Lys Ala Asn Gly Tyr Thr Thr Glu Tyr Ser Ala Ser Val Lys
1               5                   10                  15

Gly
```

<210> SEQ ID NO 112
<211> LENGTH: 12
<212> TYPE: PRT
<213> ORGANISM: Mus musculus

<400> SEQUENCE: 112

```
Ala Arg Ala Pro Leu Leu Tyr Tyr Ala Met Asp Tyr
1               5                   10
```

<210> SEQ ID NO 113
<211> LENGTH: 111
<212> TYPE: PRT
<213> ORGANISM: Mus musculus

<400> SEQUENCE: 113

```
Pro Ala Cys Leu Pro Gly Gly Ser Leu Arg Leu Ser Cys Ala Thr Ser
1               5                   10                  15

Gly Phe Thr Phe Thr Asp Tyr Tyr Met Ser Trp Val Arg Gln Pro Pro
            20                  25                  30
```

```
Gly Lys Ala Leu Glu Trp Leu Gly Phe Ile Arg Asn Lys Ala Asn Gly
        35                  40                  45

Tyr Thr Thr Glu Tyr Ser Ala Ser Val Lys Gly Arg Phe Thr Ile Ser
    50                  55                  60

Arg Asp Asn Ser Gln Ser Ile Leu Tyr Leu Gln Met Asn Thr Leu Arg
65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
            100                 105                 110


<210> SEQ ID NO 114
<211> LENGTH: 11
<212> TYPE: PRT
<213> ORGANISM: Mus musculus

<400> SEQUENCE: 114

Asn Val Ser Thr Ser Gly Tyr Ser Tyr Met His
1               5                   10


<210> SEQ ID NO 115
<211> LENGTH: 7
<212> TYPE: PRT
<213> ORGANISM: Mus musculus

<400> SEQUENCE: 115

Leu Val Ser Asn Leu Glu Ser
1               5


<210> SEQ ID NO 116
<211> LENGTH: 8
<212> TYPE: PRT
<213> ORGANISM: Mus musculus

<400> SEQUENCE: 116

Gln His Ile Arg Glu Leu Thr Arg
1               5


<210> SEQ ID NO 117
<211> LENGTH: 102
<212> TYPE: PRT
<213> ORGANISM: Mus musculus

<400> SEQUENCE: 117

Arg Leu Pro Phe Tyr Ser Leu Glu Gln Arg Ala Thr Ile Ser Tyr Arg
1               5                   10                  15

Ala Ser Lys Asn Val Ser Thr Ser Gly Tyr Ser Tyr Met His Trp Asn
            20                  25                  30

Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
            100
```

<210> SEQ ID NO 118
<211> LENGTH: 340
<212> TYPE: DNA
<213> ORGANISM: Mus musculus

<400> SEQUENCE: 118
ccggcctgct tgcctggtgg ttctctgaga ctctcctgtg caacttctgg gttcaccttc 60
actgattact acatgagctg ggtccgccag cctccaggaa aggcacttga gtggttgggt 120
tttattagaa acaaagctaa tggttacaca acagagtaca gtgcatctgt gaagggtcgg 180
ttcaccatct ccagagataa ttcccaaagc atcctctatc ttcaaatgaa caccctgaga 240
gctgaggaca gtgccactta ttactgtgca agagcccctc tactttacta tgctatggac 300
tactggggcc aagggaccac ggtcaccgtc tcctaaatta 340

<210> SEQ ID NO 119
<211> LENGTH: 306
<212> TYPE: DNA
<213> ORGANISM: Mus musculus

<400> SEQUENCE: 119
cgccttcctt tctattctct ggagcagagg gccaccatct catacagggc cagcaaaaat 60
gtcagtacat ctggctatag ttatatgcac tggaaccaac agaaaccagg acagccaccc 120
aaactcctca tctatcttgt atccaaccta gaatctgggg tccctgccag gttcagtggc 180
agtgggtctg ggacagactt caccctcaac atccatcctg tggaggagga ggatgctgca 240
acctattact gtcagcacat tagggagctt acacgttcgg agctggtacc aagctggaaa 300
tcaaac 306

<210> SEQ ID NO 120
<211> LENGTH: 5
<212> TYPE: PRT
<213> ORGANISM: Mus musculus

<400> SEQUENCE: 120

Ser Tyr Trp Met His
1 5

<210> SEQ ID NO 121
<211> LENGTH: 17
<212> TYPE: PRT
<213> ORGANISM: Mus musculus

<400> SEQUENCE: 121

Met Ile Asp Pro Ser Asn Ser Glu Thr Arg Leu Asn Gln Lys Phe Lys
1 5 10 15

Asp

<210> SEQ ID NO 122
<211> LENGTH: 12
<212> TYPE: PRT
<213> ORGANISM: Mus musculus

<400> SEQUENCE: 122

Ala Arg Gly Leu Arg His Tyr Trp Tyr Phe Asp Val
1 5 10

<210> SEQ ID NO 123
<211> LENGTH: 101
<212> TYPE: PRT
<213> ORGANISM: Mus musculus

<400> SEQUENCE: 123

```
Val Ser Cys Lys Ala Ser Gly Tyr Thr Phe Thr Ser Tyr Trp Met His
1               5                   10                  15

Trp Val Lys Gln Arg Pro Gly Gln Gly Leu Glu Trp Ile Gly Met Ile
            20                  25                  30

Asp Pro Ser Asn Ser Glu Thr Arg Leu Asn Gln Lys Phe Lys Asp Lys
        35                  40                  45

Ala Thr Leu Asn Val Asp Lys Ser Ser Asn Thr Ala Tyr Met Gln Leu
    50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
                85                  90                  95

Thr Val Ser Ser Lys
            100
```

<210> SEQ ID NO 124
<211> LENGTH: 11
<212> TYPE: PRT
<213> ORGANISM: Mus musculus

<400> SEQUENCE: 124

```
Ser Val Ser Thr Ser Gly Tyr Ser Tyr Met His
1               5                   10
```

<210> SEQ ID NO 125
<211> LENGTH: 7
<212> TYPE: PRT
<213> ORGANISM: Mus musculus

<400> SEQUENCE: 125

```
Leu Val Ser Asn Leu Glu Ser
1               5
```

<210> SEQ ID NO 126
<211> LENGTH: 9
<212> TYPE: PRT
<213> ORGANISM: Mus musculus

<400> SEQUENCE: 126

```
Gln His Ile Arg Glu Leu Thr Arg Ser
1               5
```

<210> SEQ ID NO 127
<211> LENGTH: 99
<212> TYPE: PRT
<213> ORGANISM: Mus musculus

<400> SEQUENCE: 127

```
Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
            20                  25                  30

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Glu Asp Ala Ala Thr Tyr Tyr Cys
65                  70                  75                  80
```

```
Gln His Ile Arg Glu Leu Thr Arg Ser Glu Glu Val Pro Ser Trp Arg
                85                  90                  95

Ser Asn Lys


<210> SEQ ID NO 128
<211> LENGTH: 304
<212> TYPE: DNA
<213> ORGANISM: Mus musculus

<400> SEQUENCE: 128

gtgtcctgca aggcttcagg ctataccttc accagctact ggatgcactg ggtgaaacag      60

aggcctggac aaggccttga gtggattggc atgattgatc cttccaatag tgaaactagg     120

ttaaatcaga agttcaagga caaggccaca ttgaatgtag acaaatcctc caacacagcc     180

tacatgcagc tcagcagcct gacatctgag gactctgcag tctattactg tgcaagaggg     240

ttacgccact actggtactt cgatgtctgg ggccaaggga ccacggtcac cgtctcctca     300

aaaa                                                                  304


<210> SEQ ID NO 129
<211> LENGTH: 298
<212> TYPE: DNA
<213> ORGANISM: Mus musculus

<400> SEQUENCE: 129

actattctct ggagagaggg ccccttctca tacagggcca gcaaaagtgt cagtacatct      60

ggctatagtt atatgcactg gaaccaacag aaaccaggac agccacccag actcctcatc     120

tatcttgtat ccaacctaga atctggggtc cctgccaggt tcagtggcag tgggtctggg     180

acagacttca ccctcaacat ccatcctgtg gaggaggagg atgctgcaac ctattactgt     240

cagcacatta gggagcttac acgttcggag gaggtaccaa gctggagatc aaacaaaa       298


<210> SEQ ID NO 130
<211> LENGTH: 22
<212> TYPE: DNA
<213> ORGANISM: Artificial Sequence
<220> FEATURE:
<223> OTHER INFORMATION: Synthetic primer

<400> SEQUENCE: 130

aggtsharct gcagsagtcw gg                                               22


<210> SEQ ID NO 131
<211> LENGTH: 34
<212> TYPE: DNA
<213> ORGANISM: Artificial Sequence
<220> FEATURE:
<223> OTHER INFORMATION: Synthetic primer

<400> SEQUENCE: 131

tgaggagacg gtgaccgtgg tcccttggcc ccag                                  34


<210> SEQ ID NO 132
<211> LENGTH: 27
<212> TYPE: DNA
<213> ORGANISM: Artificial Sequence
<220> FEATURE:
<223> OTHER INFORMATION: Synthetic primer

<400> SEQUENCE: 132

tccgatatcc agctgaccca gtctcca                                          27
```

<210> SEQ ID NO 133
<211> LENGTH: 31
<212> TYPE: DNA
<213> ORGANISM: Artificial Sequence
<220> FEATURE:
<223> OTHER INFORMATION: Synthetic primer

<400> SEQUENCE: 133
gtttgatctc cagcttggta cchscdccga a 31

<210> SEQ ID NO 134
<211> LENGTH: 15
<212> TYPE: DNA
<213> ORGANISM: Artificial Sequence
<220> FEATURE:
<223> OTHER INFORMATION: Synthetic primer

<400> SEQUENCE: 134
agtcacgacg ttgta 15

<210> SEQ ID NO 135
<211> LENGTH: 17
<212> TYPE: DNA
<213> ORGANISM: Artificial Sequence
<220> FEATURE:
<223> OTHER INFORMATION: Synthetic primer

<400> SEQUENCE: 135
caggaaacag ctatgac 17

<210> SEQ ID NO 136
<211> LENGTH: 58
<212> TYPE: PRT
<213> ORGANISM: Homo sapiens

<400> SEQUENCE: 136

```
Val Phe Gln Ser Asn Tyr Phe Asp Ser Thr His Asn His Gln Asn Gly
1               5                   10                  15

Leu Cys Glu Glu Glu Glu Ala Ala Ser Ala Pro Ala Val Glu Asp Gln
            20                  25                  30

Val Pro Glu Ala Glu Pro Glu Pro Ala Glu Glu Tyr Thr Glu Gln Ser
        35                  40                  45

Glu Val Glu Ser Thr Glu Tyr Val Asn Arg
    50                  55
```

<210> SEQ ID NO 137
<211> LENGTH: 15
<212> TYPE: PRT
<213> ORGANISM: Homo sapiens

<400> SEQUENCE: 137

```
Tyr Thr Glu Gln Ser Glu Val Glu Ser Thr Glu Tyr Val Asn Arg
1               5                   10                  15
```

<210> SEQ ID NO 138
<211> LENGTH: 11
<212> TYPE: PRT
<213> ORGANISM: Homo sapiens

<400> SEQUENCE: 138

```
Ser Glu Val Glu Ser Thr Glu Tyr Val Asn Arg
1               5                   10
```